United States Patent (10) Patent No.: US 11,143,962 B2
Toida et al. (45) Date of Patent: *Oct. 12, 2021

(54) MATERIAL FOR FORMING UNDERLAYER FILM FOR LITHOGRAPHY, COMPOSITION FOR FORMING UNDERLAYER FILM FOR LITHOGRAPHY, UNDERLAYER FILM FOR LITHOGRAPHY AND PRODUCTION METHOD THEREOF, PATTERN FORMING METHOD, RESIN, AND PURIFICATION METHOD

(71) Applicant: Mitsubishi Gas Chemical Company, Inc., Tokyo (JP)

(72) Inventors: Takumi Toida, Hiratsuka (JP); Takashi Makinoshima, Hiratsuka (JP); Takashi Sato, Hiratsuka (JP); Masatoshi Echigo, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/755,972

(22) PCT Filed: Aug. 25, 2016

(86) PCT No.: PCT/JP2016/074867
§ 371 (c)(1),
(2) Date: Feb. 27, 2018

(87) PCT Pub. No.: WO2017/038645
PCT Pub. Date: Mar. 9, 2017

(65) Prior Publication Data
US 2019/0041750 A1 Feb. 7, 2019

(30) Foreign Application Priority Data

Aug. 31, 2015 (JP) ................................. 2015-170191

(51) Int. Cl.
*G03F 7/16* (2006.01)
*G03F 7/11* (2006.01)
(Continued)

(52) U.S. Cl.
CPC ............... *G03F 7/30* (2013.01); *C07C 37/72* (2013.01); *C07C 39/12* (2013.01); *C07C 39/14* (2013.01);
(Continued)

(58) Field of Classification Search
CPC . G03F 7/11; G03F 7/0392; G03F 7/30; G03F 7/16; G03F 7/168; C07C 69/616;
(Continued)

(56) References Cited

U.S. PATENT DOCUMENTS 2,100,798 A 11/1937 Dilthey
2,546,872 A 3/1951 Schmid
(Continued)

FOREIGN PATENT DOCUMENTS

CN 1414031 4/2003
CN 1853141 10/2006
(Continued)

OTHER PUBLICATIONS

International Search Report for PCT/JP2014/051775, dated Feb. 25, 2014, and English translation (4 pages).
(Continued)

*Primary Examiner* — John S Chu
(74) *Attorney, Agent, or Firm* — Fitch, Even, Tabin & Flannery LLP

(57) ABSTRACT

The present embodiment provides a material for forming an underlayer film for lithography, containing at least any of a compound represented by following formula (1) or a resin including a structural unit derived from a compound represented by the following formula (1),

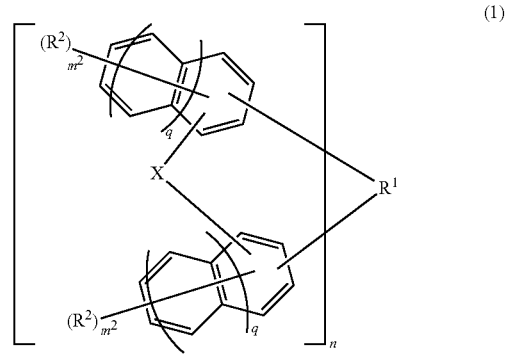

wherein $R^1$ represents a 2n-valent group having 1 to 60 carbon atoms, or a single bond, each $R^2$ independently represents a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, a thiol group, a hydroxyl group, or a group where a hydrogen atom of a hydroxyl group is substituted with an acid-dissociable group, and may be the same or different in the same naphthalene ring or benzene ring, in which at least one $R^2$ represents a group where a hydrogen atom of a hydroxyl group is substituted with an acid-dissociable group, n is an integer of 1 to 4, and structural formulae of n structural units in square brackets [ ] may be the same or different when n is an integer of 2 or more, X represents an oxygen atom, a sulfur atom, or a non-bridging group, each $m^2$ is independently an integer of 0 to 7, provided that at least one $m^2$ is an integer of 1 to 7, and each q is independently 0 or 1.

17 Claims, No Drawings

(51) Int. Cl.

| | | |
|---|---|---|
| C08G 61/00 | (2006.01) | |
| C07C 37/72 | (2006.01) | |
| C07C 39/12 | (2006.01) | |
| C07C 39/14 | (2006.01) | |
| G03F 7/30 | (2006.01) | |
| G03F 7/36 | (2006.01) | |
| C07C 69/96 | (2006.01) | |
| C07D 311/78 | (2006.01) | |
| H01L 21/027 | (2006.01) | |
| G03F 7/09 | (2006.01) | |
| G03F 7/039 | (2006.01) | |
| C07D 405/04 | (2006.01) | |
| C08G 61/12 | (2006.01) | |
| C09D 165/00 | (2006.01) | |
| G03F 7/20 | (2006.01) | |
| G03F 7/32 | (2006.01) | |
| G03F 7/38 | (2006.01) | |
| H01L 21/311 | (2006.01) | |
| H01L 21/3213 | (2006.01) | |
| H01L 21/768 | (2006.01) | |
| C08G 8/14 | (2006.01) | |
| C08G 8/18 | (2006.01) | |
| C08G 8/08 | (2006.01) | |

(52) U.S. Cl.
CPC ............ *C07C 69/96* (2013.01); *C07D 311/78* (2013.01); *C07D 405/04* (2013.01); *C08G 61/00* (2013.01); *C08G 61/122* (2013.01); *C09D 165/00* (2013.01); *G03F 7/0392* (2013.01); *G03F 7/094* (2013.01); *G03F 7/11* (2013.01); *G03F 7/16* (2013.01); *G03F 7/168* (2013.01); *G03F 7/2037* (2013.01); *G03F 7/322* (2013.01); *G03F 7/36* (2013.01); *G03F 7/38* (2013.01); *H01L 21/027* (2013.01); *H01L 21/0276* (2013.01); *H01L 21/31116* (2013.01); *H01L 21/31144* (2013.01); *H01L 21/32135* (2013.01); *H01L 21/32139* (2013.01); *H01L 21/76816* (2013.01); *H01L 21/76877* (2013.01); *C08G 8/08* (2013.01); *C08G 8/14* (2013.01); *C08G 8/18* (2013.01); *C08G 2261/11* (2013.01); *C08G 2261/148* (2013.01); *C08G 2261/228* (2013.01); *C08G 2261/3242* (2013.01); *C08G 2261/71* (2013.01)

(58) Field of Classification Search
CPC ......... C07C 37/72; C07C 39/12; C07C 39/14; C07C 69/96; C08G 61/00; C08G 8/08; C08G 8/14; C08G 8/18
USPC ................. 430/270.1, 271.1, 326; 549/382; 568/719; 560/61, 100
See application file for complete search history.

(56) References Cited

U.S. PATENT DOCUMENTS

| 2,587,437 | A | 2/1952 | Bralley | |
|---|---|---|---|---|
| 3,947,468 | A | 3/1976 | Hall | |
| 4,252,884 | A | 2/1981 | Bennett | |
| 4,289,839 | A | 9/1981 | DiPippo | |
| 4,482,489 | A | 11/1984 | DiPippo | |
| 4,579,758 | A | 4/1986 | Dorsch | |
| 5,332,648 | A | 7/1994 | Kihara | |
| 5,986,094 | A | 11/1999 | Ghoshal | |
| 6,784,228 | B2 * | 8/2004 | Ogura | C07D 311/78 523/466 |
| 6,794,408 | B2 | 9/2004 | Eder | |
| 7,871,751 | B2 | 1/2011 | Echigo | |
| 9,136,121 | B2 | 9/2015 | Hatakeyama | |
| 9,274,426 | B2 | 3/2016 | Rahman | |
| 9,316,913 | B2 | 4/2016 | Echigo | |
| 9,540,339 | B2 | 1/2017 | Echigo | |
| 9,908,831 | B2 | 3/2018 | Echigo | |
| 10,303,055 | B2 | 5/2019 | Sato | |
| 10,377,734 | B2 | 8/2019 | Echigo | |
| 2002/0106909 | A1 | 8/2002 | Kato | |
| 2003/0092852 | A1 | 5/2003 | Ogura | |
| 2004/0197709 | A1 | 10/2004 | Arase | |
| 2005/0074695 | A1 | 4/2005 | Nakamura | |
| 2005/0255712 | A1 | 11/2005 | Kato et al. | |
| 2007/0059632 | A1 | 3/2007 | Oguro et al. | |
| 2007/0172759 | A1 | 7/2007 | Ogihara | |
| 2007/0232839 | A1 | 10/2007 | Yoshitomo | |
| 2007/0275325 | A1 | 11/2007 | Hatakeyama | |
| 2008/0113294 | A1 | 5/2008 | Echigo | |
| 2008/0138744 | A1 | 6/2008 | Hatanaka | |
| 2008/0153031 | A1 * | 6/2008 | Echigo | G03F 7/0382 430/281.1 |
| 2009/0171061 | A1 | 7/2009 | Sue | |
| 2009/0246684 | A1 | 10/2009 | Kim | |
| 2009/0261300 | A1 | 10/2009 | Watanabe | |
| 2010/0047709 | A1 | 2/2010 | Echigo | |
| 2010/0099044 | A1 | 4/2010 | Hatakeyama | |
| 2010/0104977 | A1 | 4/2010 | Hatakeyama | |
| 2010/0136477 | A1 | 6/2010 | Ng | |
| 2010/0190107 | A1 | 7/2010 | Shibata | |
| 2010/0207516 | A1 | 8/2010 | Moriwaki | |
| 2010/0227859 | A1 | 9/2010 | Li | |
| 2010/0285407 | A1 | 11/2010 | Ogihara | |
| 2010/0316950 | A1 | 12/2010 | Oguro et al. | |
| 2011/0177459 | A1 | 7/2011 | Ogihara | |
| 2011/0230058 | A1 | 9/2011 | Sakamoto et al. | |
| 2011/0274713 | A1 | 11/2011 | Burn | |
| 2011/0311920 | A1 | 12/2011 | Kinsho | |
| 2012/0064725 | A1 | 3/2012 | Kinsho | |
| 2012/0171611 | A1 | 7/2012 | Ideno et al. | |
| 2012/0184103 | A1 | 7/2012 | Ogihara | |
| 2012/0220112 | A1 | 8/2012 | Hatakeyama | |
| 2012/0228584 | A1 | 9/2012 | Wigglesworth | |
| 2013/0004896 | A1 | 1/2013 | Echigo et al. | |
| 2013/0056653 | A1 | 3/2013 | Hatakeyama | |
| 2013/0084705 | A1 | 4/2013 | Nakafuji et al. | |
| 2013/0087529 | A1 | 4/2013 | Hatakeyama et al. | |
| 2013/0150627 | A1 | 6/2013 | Okada | |
| 2014/0186776 | A1 | 7/2014 | Uchiyama | |
| 2014/0248556 | A1 | 9/2014 | Kato | |
| 2014/0248561 | A1 * | 9/2014 | Echigo | C07D 311/96 430/281.1 |
| 2014/0308615 | A1 | 10/2014 | Echigo et al. | |
| 2014/0319097 | A1 | 10/2014 | Kim | |
| 2014/0363768 | A1 | 12/2014 | Kinsho | |
| 2014/0363955 | A1 | 12/2014 | Hatakeyama et al. | |
| 2014/0363957 | A1 | 12/2014 | Hatakeyama et al. | |
| 2014/0363958 | A1 | 12/2014 | Hatakeyama et al. | |
| 2015/0030980 | A1 | 1/2015 | Echigo et al. | |
| 2015/0037735 | A1 | 2/2015 | Yang | |
| 2015/0090691 | A1 | 4/2015 | Echigo et al. | |
| 2015/0309403 | A1 | 10/2015 | Rahman | |
| 2015/0368224 | A1 | 12/2015 | Echigo | |
| 2015/0376157 | A1 * | 12/2015 | Echigo | C07C 69/734 430/270.1 |
| 2015/0376158 | A1 | 12/2015 | Echigo | |
| 2015/0376202 | A1 | 12/2015 | Echigo | |
| 2016/0130243 | A1 | 5/2016 | Satou | |
| 2016/0145231 | A1 | 5/2016 | Echigo | |
| 2017/0183279 | A1 | 6/2017 | Echigo | |
| 2017/0349564 | A1 * | 12/2017 | Toida | C07D 311/78 |
| 2018/0074402 | A1 * | 3/2018 | Toida | C07D 311/92 |
| 2018/0074406 | A1 * | 3/2018 | Toida | G03F 7/004 |
| 2018/0208703 | A1 | 7/2018 | Okada et al. | |

FOREIGN PATENT DOCUMENTS

| CN | 101889247 | 11/2010 |
|---|---|---|
| CN | 102070595 | 5/2011 |
| CN | 103304385 A | 9/2013 |
| CN | 103733136 | 4/2014 |

(56) References Cited

FOREIGN PATENT DOCUMENTS

| | | |
|---|---|---|
| CN | 103804196 A | 5/2014 |
| CN | 104557552 A | 4/2015 |
| EP | 1275673 | 1/2003 |
| EP | 1300403 | 4/2003 |
| EP | 1666970 | 6/2006 |
| EP | 2743249 | 6/2014 |
| EP | 2743769 | 6/2014 |
| EP | 2743770 A1 | 6/2014 |
| EP | 3279190 | 2/2018 |
| JP | S48049508 A | 7/1973 |
| JP | 62094841 A | 5/1987 |
| JP | S62191850 A | 8/1987 |
| JP | H01283280 | 11/1989 |
| JP | H04217675 | 8/1992 |
| JP | H05-19463 A | 1/1993 |
| JP | H05034913 A | 2/1993 |
| JP | H05134415 A | 5/1993 |
| JP | H05163290 A | 6/1993 |
| JP | 05216235 A | 8/1993 |
| JP | H06049402 A | 2/1994 |
| JP | H06242607 A | 9/1994 |
| JP | H07215833 | 8/1995 |
| JP | H1025220 | 1/1998 |
| JP | H10045764 A | 2/1998 |
| JP | H11072925 | 3/1999 |
| JP | 2001042525 | 2/2001 |
| JP | 2002214769 | 7/2002 |
| JP | 2002-334869 A | 11/2002 |
| JP | 2002334896 | 11/2002 |
| JP | 2002341542 | 11/2002 |
| JP | 2003201333 | 7/2003 |
| JP | 2004-177668 A | 6/2004 |
| JP | 2004-271838 A | 9/2004 |
| JP | 2005-250434 A | 9/2005 |
| JP | 2005266741 A | 9/2005 |
| JP | 2005326838 A | 11/2005 |
| JP | 2005326868 A | 11/2005 |
| JP | 2005-346024 A | 12/2005 |
| JP | 2006036648 | 2/2006 |
| JP | 2006098869 | 4/2006 |
| JP | 2006113136 | 4/2006 |
| JP | 2006160663 | 6/2006 |
| JP | 2006213634 | 8/2006 |
| JP | 2006259482 A | 9/2006 |
| JP | 2007019294 | 1/2007 |
| JP | 2007199653 | 8/2007 |
| JP | 2007-226170 A | 9/2007 |
| JP | 2007-226204 A | 9/2007 |
| JP | 2007262398 | 10/2007 |
| JP | 2007326847 | 12/2007 |
| JP | 2008065081 | 3/2008 |
| JP | 2008145539 A | 6/2008 |
| JP | 2008201954 A | 9/2008 |
| JP | 2008239868 | 10/2008 |
| JP | 2009073738 A | 4/2009 |
| JP | 2009098155 A | 5/2009 |
| JP | 2009108313 | 5/2009 |
| JP | 2009155256 | 7/2009 |
| JP | 2009173623 A | 8/2009 |
| JP | 2009300978 | 12/2009 |
| JP | 2010160189 | 7/2010 |
| JP | 2010170013 | 8/2010 |
| JP | 2010219295 | 9/2010 |
| JP | 2010235643 | 10/2010 |
| JP | 2011068624 | 4/2011 |
| JP | 2011105887 | 6/2011 |
| JP | 2011150023 | 8/2011 |
| JP | 20121687 | 1/2012 |
| JP | 2012068652 | 4/2012 |
| JP | 2012077295 | 4/2012 |
| JP | 2012083731 A | 4/2012 |
| JP | 2012145897 | 8/2012 |
| JP | 2013064978 A | 4/2013 |
| JP | 2013-083939 A | 5/2013 |
| JP | 2013083833 A | 5/2013 |
| JP | 2013087173 A | 5/2013 |
| JP | 2013137524 A | 7/2013 |
| JP | 2013253161 A | 12/2013 |
| JP | 2014196288 A | 10/2014 |
| JP | 2014205746 | 10/2014 |
| JP | 2015-018220 A | 1/2015 |
| JP | 2015-018221 A | 1/2015 |
| JP | 2015-018223 A | 1/2015 |
| JP | 2015087115 A | 5/2015 |
| JP | 2015514691 A | 5/2015 |
| JP | 2015-127821 A | 7/2015 |
| KR | 1020100095563 | 8/2010 |
| WO | 9736960 | 10/1997 |
| WO | 0214434 | 2/2002 |
| WO | 03017002 | 2/2003 |
| WO | 2004/066377 A1 | 8/2004 |
| WO | 2005/029189 A1 | 3/2005 |
| WO | 2005111724 | 11/2005 |
| WO | 2006/068267 A1 | 6/2006 |
| WO | 2007097457 | 8/2007 |
| WO | 2008/053974 A1 | 5/2008 |
| WO | 2008137816 A2 | 11/2008 |
| WO | 2009/072465 A1 | 6/2009 |
| WO | 2009119201 A1 | 10/2009 |
| WO | 2009145224 | 12/2009 |
| WO | 2011/034062 A1 | 3/2011 |
| WO | 2012165507 A1 | 12/2012 |
| WO | 2013/010102 A2 | 1/2013 |
| WO | 2013/024777 A1 | 2/2013 |
| WO | 2013/024778 A1 | 2/2013 |
| WO | 2013/024779 A1 | 2/2013 |
| WO | 2013066067 | 5/2013 |
| WO | 2013184755 | 12/2013 |
| WO | 2014050690 | 4/2014 |
| WO | 2014/123032 A1 | 8/2014 |
| WO | 2014199660 | 12/2014 |

OTHER PUBLICATIONS

International Search Report for PCT/JP2015/084907, dated Feb. 9, 2016, and English translation (7 pages).
International Search Report for PCT/JP2014/052524, dated Mar. 25, 2014, and English Translation (8 pages).
International Search Report for PCT/JP2014/052530, dated May 13, 2014, and English Translation (8 pages).
International Search Report for PCT/JP2012/070304, dated Oct. 23, 2012, and English translation (9 pages).
International Search Report for PCT/JP2012/070305, dated Sep. 11, 2012, and English Translation (5 pages).
International Search Report for PCT/JP2016/056332, dated May 31, 2016, and English translation (11 pages).
International Search Report for PCT/JP2016/056333, dated May 24, 2016, and English translation (7 pages).
Written Opinion of the International Searching Authority for PCT/JP2012/070304, dated Oct. 23, 2012, and English translation (12 pages).
Luo, Junfei et al., "Salicylic acids as readily available starting materials for the synthesis of meta-substituted biaryls," ChemComm, 2015, vol. 51, pp. 3127-3130.
Ahmed Munir et al., The Direct Bradsher Reaction. Part I. Synthesis of Thiophen Analogues of Linear Polycyclic Hydrocarbons, Journal of the Chemical Society, Perkin Transactions 1,1973, pp. 1099-1103.
Areephong, Jetsuda, et al., "A concise synthesis of functionalized 7-oxa-[5]-helicenes," Tetrahedron Letters, 2004, vol. 45, pp. 3067-3070.
Bentley, K. W., and Robinson, R., "A Synthesis of alpha-Anhydrotrimethylbrazilone," Tetrahedron Letters, 1959, vol. 1, Issue 2, pp. 11-14.
Brecher, Jonathan, Graphical Representation Standards for Chemical Structure Diagrams, Pure Appl. Chem., 2008, pp. 277-410, vol. 80, No. 2, Cambridge, Massachusetts.
Burnett, James C., et al. "Novel small molecule inhibitors of botulinum neurotoxin A metalloprotease activity," Biochemical and Biophysical Research Communications, vol. 310, No. 1, Oct. 2003, pp. 84-93.

(56) References Cited

OTHER PUBLICATIONS

Cameron, Donald W., et al., "Synthesis of a natural polychloro dinaphthofuran quinone," Tetrahedron Letters, 1980, vol. 21(14), pp. 1385-1386.
Chatterjea, J.N., "Experiments on the Syntheses of Furano Compounds. Part XII. Further Transformations of isoCoumaranone," Journal of the Indian Chemical Society, 1957, vol. 34, Issue 4, pp. 299-305.
Clowes, G. A., et al., "Studies of the Scholl reaction: Oxidative Dehydrogenation involving 1-Ethoxynaphthylenen and Related Compounds," J Chem. Soc (C) 2519-2526 (1968).
Dann, von Otto, and Hofmann, Hans, Synthese von ( )-Brasilin, Justus Liebigs Annalen der Chemie, 1963, vol. 667, Issue 1, pp. 116-125.
English Translation of JP H01-283280 A, Nov. 14, 1989.
European Journal of Medicinal Chemistry, published bi-monthly, Ejmcs, 13(4): 381-385 (1978).
Ghodratbeigi Mohsen et al., "Design, modeling and synthesis of molecular tweezers with self-assembly Properties," Journal of Molecular Structure, 2011, vol. 990, No. 1, pp. 140-151.
Hagihara K. et al., "The effect of Ti-addition on plastic deformation and fracture behavior of directionally solidified NiiAl/Cr(Mo) eutetic alloys," Intermetallics, 2006, vol. 14, No. 10, pp. 1326-1331.
Hannuksela, Miska M. et al., "Hook for scalable extensions: video parameter set," Joint Collaborative Team on Video Coding (JCT-VC) of ITU-T SG 16 WP 3 and ISO/IEC JTC 1/SC 29/WG 11, May 2012, pp. 1-6.
Jha Amitabh and Beal Jennifer, "Convenient synthesis of 12H-benzo[a]xanthenes from 2-tetralone," Tetrahedron Letters, 2004, vol. 45, No. 49, pp. 8999-9001.
Journal of the Chemical Society, p. 5336-5341 (Nov. 1963).
Machine English Translation of JP 2008-239868 A, Oct. 9, 2008.
Massif, Cedrik, et al. "New insights into the water-solubilisation of fluorophores by post-synthetic 'click' and Sonogashira reactions," Organic & Biomolecular Chemistry, vol. 10, No. 22, Apr. 2012, pp. 4430-4336.
Nakayama, Tomonari, Nomura, Masayoshi, Haga, Kohji, and Ueda, Mitsuru, A New Three-Component Photoresist Based on Calix[4]resorcinarene Derivative, a Cross-Linker, and a Photo-acid Generator, The Chemical Society of Japan, Bulletin of the Chemical Society of Japan, 1998, vol. 71, No. 12, pp. 2979-2984.
Nature, 161:930-931 (1948).
Nishiyama Tomihiro et al., Antioxidant activities of fused heterocyclic compounds, xanthene-2,7-diols with BHT or Catechol skeleton, Polymer Degradation and Stability, 1998, vol. 62, No. 3, pp. 529-534.
Ohishi Takeshi. Tetrahedron Letters 42 (2001) 2493-2496.
Osman A-M, Reactions Between Chloro-p-benzoquinones and Beta-Naphtol, Journal of Organic Chemistry, 1957, vol. 22, pp. 342-344.
Percec, Virgil, et al., Synthesis of Aromatic Polyethers by Scholl Reaction. I. Poly(1,1'-Dinaphthyl Ether Phenyl Sulfone)s and Poly(1,1'-Dinaphthyl Ether Phenyl Ketone)s, Journal of Polymer Science: Part A: Polymer Chemistry, 1988, vol. 26, pp. 783-805.
Percec, Virgil, et al., "Synthesis of Aromatic Polyethers by Scholl Reaction. VI. Aromatic Polyethers by Cation-Radical Polymerization of 4,4'-, 3,3'-, and 2-2'-Bis(1-naphthoxy)biphenyls and of 1,3-Bis(1-naphthoxy)benzene," Macromolecules, 1992, vol. 25(1), pp. 64-74.
Protiva, Miroslav et al., Potential metabolites of tricyclic neuroleptics: 2,8-dihydroxy and 3,8-dihydroxy derivatives of 10-(4-methylpiperazino)-10,11-dihydrodibenzo[b,f]thiepin, Part CXXXIII in the series Neurotropic and Psychotropic Agents, Collection of Czechoslovak Chemical Communications, 1979, vol. 44, No. 10, pp. 2987-2996.
Protiva, Miroslav, et al., "Potential metabolites or tricyclic neuroleptics" 3,7-dimethoxy and 7,8-dimethoxy derivatives of 10-(4-methylpiperazino )-10,11-dihydrodibenzo[b,f]thiepin, Collection of Czechoslovak Chemical Communications, 1981, vol. 46, pp. 1808-1817.
Shinji Okazaki et al., "New Trends of Photoresists", CMC Publishing Co., Ltd., Sep. 2009, p. 211-259.
Singh Ritesh and Panda Gautam, "Scandium triflate-catalyzed one-pot domino approach towards general and efficient syntheses of unsymmetrical 9-substituted xanthene derivatives," Organic & Biomolecular Chemistry, 2010, vol. 8, No. 5, pp. 1097-1105.
Sirkecioglu Okan et al., A Novel Synthesis of 14-(Hydroxymethylalkyl) Derivatives of Dibenzoxanthenes and 3,3-Dimethyl-4-(2-hydroxy-1-naphthyl)benzo[f]chroman, Journal of Heterocyclic Chemistry, Mar. 1, 1998, vol. 35, No. 2, pp. 457-460.
Sirringhaus Henning et al., Dibenzothienobisbenzothiophene—a novel fused-ring oligomer with high field-effect mobility, Journal of Materials Chemistry, 1999, vol. 9, pp. 2095-2101.
Skandinavisches Archiv fuer Physiologie, 43: 215-243 (1923).
Tian-jun Liu, Ke-shen Zhang, Yong-jun Chen, Dong Wang and Chao-jun Li, "Chiral Conjugated Oligomer Based on 1, 1'-Binol With 3, 3' -Acetylene -Phenylene-Acetylene Spacer", Chinese Journal of Polymer Science, Mar. 8, 2001, vol. 19, No. 5, p. 521-526.

* cited by examiner

MATERIAL FOR FORMING UNDERLAYER FILM FOR LITHOGRAPHY, COMPOSITION FOR FORMING UNDERLAYER FILM FOR LITHOGRAPHY, UNDERLAYER FILM FOR LITHOGRAPHY AND PRODUCTION METHOD THEREOF, PATTERN FORMING METHOD, RESIN, AND PURIFICATION METHOD

CROSS-REFERENCE TO RELATED APPLICATIONS

This application is a U.S. national phase application filed under 35 U.S.C. § 371 of International Application PCT/JP2016/074867, filed on Aug. 25, 2016, designating the United States, which claims priority from Japanese Application Number 2015-170191, filed Aug. 31, 2015.

FIELD OF THE INVENTION

The present embodiment relates to a material for forming an underlayer film for lithography, a composition for forming an underlayer film for lithography, an underlayer film for lithography and a production method thereof, a pattern forming method, a resin, and a purification method.

BACKGROUND OF THE INVENTION

Semiconductor devices are manufactured through microfabrication by lithography using a photoresist material, but are required to be made finer by a pattern rule in accordance with the increase in integration degree and the increase in speed of LSI in recent years. Then, in lithography using exposure to light, which is currently used as a general-purpose technique, the resolution is now approaching the intrinsic limitation associated with the wavelength of the light source.

A light source for lithography, for use in forming a resist pattern, has a shorter wavelength from a KrF excimer laser (248 nm) to an ArF excimer laser (193 nm). However, as the resist pattern is made finer and finer, there arise a problem of resolution and a problem of collapse of the resist pattern after development, and therefore there is demanded for making a resist film thinner. Meanwhile, if the resist film is merely made thinner, it is difficult to achieve the resist pattern having a film thickness sufficient for processing a substrate. Accordingly, there has been increasingly required a process in which not only the resist pattern but also a resist underlayer film is prepared between a resist and a semiconductor substrate to be processed and the resist underlayer film is allowed to have a function as a mask at the time of processing the substrate.

Currently, as the resist underlayer film for such a process, various ones are known. For example, as one for realizing a resist underlayer film for lithography, having a selection ratio of dry etching rate close to the resist, unlike a conventional resist underlayer film having a high etching rate, there has been proposed a material for forming an underlayer film for multilayer resist process, containing a resin component having at least a substituent which releases a terminal group to form a sulfonic acid residue when a predetermined energy is applied, and a solvent (see, for example, Patent Literature 1). In addition, as one for realizing a resist underlayer film for lithography, having a smaller selection ratio of dry etching rate than the resist, there has been proposed a resist underlayer film material including a polymer having a specified repeating unit (see, for example, Patent Literature 2). Furthermore, as one for realizing a resist underlayer film for lithography, having a smaller selection ratio of dry etching rate than the semiconductor substrate, there has been proposed a resist underlayer film material including a polymer formed by co-polymerizing a repeating unit of acenaphthylene, and a substituted or non-substituted repeating unit having a hydroxy group (see, for example, Patent Literature 3).

On the other hand, as a material for allowing such a resist underlayer film to have a high etching resistance, an amorphous carbon underlayer film is well known, which is formed by CVD using methane gas, ethane gas, acetylene gas, or the like as a raw material. However, there is demanded, in terms of process, a resist underlayer film material that can form a resist underlayer film in a wet process such as a spin coating method or screen printing.

In addition, as a material that is excellent in optical characteristics and etching resistance and that is capable of being dissolved in a solvent and being applied to a wet process, a composition for forming an underlayer film for lithography, which contains a naphthalene formaldehyde polymer including a specified constituent unit, and an organic solvent (see Patent Literatures 4 and 5), has been proposed.

Meanwhile, with respect to a forming method of an intermediate layer for use in forming a resist underlayer film in a three-layer process, for example, known are a forming method of a silicon nitride film (see, for example, Patent Literature 6), and a CVD forming method of a silicon nitride film (see, for example, Patent Literature 7). In addition, as an intermediate layer material for a three-layer process, known is a material containing a silsesquioxane-based silicon compound (see, for example, Patent Literatures 8 and 9).

CITATION LIST

Patent Literature

Patent Literature 1: Japanese Patent Laid-Open No. 2004-177668
Patent Literature 2: Japanese Patent Laid-Open No. 2004-271838
Patent Literature 3: Japanese Patent Laid-Open No. 2005-250434
Patent Literature 4: International Publication No. WO 2009/072465
Patent Literature 5: International Publication No. WO 2011/034062
Patent Literature 6: Japanese Patent Laid-Open No. 2002-334869
Patent Literature 7: International Publication No. WO 2004/066377
Patent Literature 8: Japanese Patent Laid-Open No. 2007-226170
Patent Literature 9: Japanese Patent Laid-Open No. 2007-226204

SUMMARY OF INVENTION

As described above, many materials for forming an underlayer film for lithography have been conventionally proposed, but there are no such materials that not only have such a high solvent solubility as to be able to be applied to a wet process such as a spin coating method or screen printing, but also simultaneously satisfy heat resistance and etching resistance at a high level, and thus a new material is required to be developed.

The present invention has been then made in view of the above prior art problem, and an object thereof is to provide a material for forming an underlayer film for lithography, which can be applied to a wet process and which is useful for forming a photoresist underlayer film excellent in heat resistance and etching resistance.

The present inventors have intensively studied to solve the above prior art problem, and as a result, have found that a photoresist underlayer film excellent in heat resistance and etching resistance is obtained by using a compound or a resin having a specified structure, thereby leading to the completion of the present invention. That is, the present invention is as follows.

[1]

A material for forming an underlayer film for lithography, comprising at least any of a compound represented by following formula (1) or a resin including a structural unit derived from a compound represented by the following formula (1),

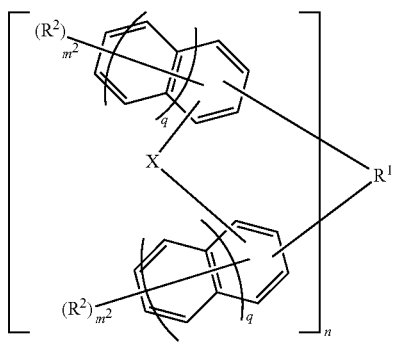

(1)

wherein $R^1$ represents a 2n-valent group having 1 to 60 carbon atoms, or a single bond, each $R^2$ independently represents a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, a thiol group, a hydroxyl group, or a group where a hydrogen atom of a hydroxyl group is substituted with an acid-dissociable group, and may be the same or different in the same naphthalene ring or benzene ring, in which at least one $R^2$ represents a group where a hydrogen atom of a hydroxyl group is substituted with an acid-dissociable group, n is an integer of 1 to 4, and structural formulae of n structural units in square brackets [ ] may be the same or different when n is an integer of 2 or more, X represents an oxygen atom, a sulfur atom, or a non-bridging group, each $m^2$ is independently an integer of 0 to 7, provided that at least one $m^2$ is an integer of 1 to 7, and each q is independently 0 or 1.

[2]

The material for forming the underlayer film for lithography according to [1], wherein the compound represented by the formula (1) is a compound represented by following formula (1-1),

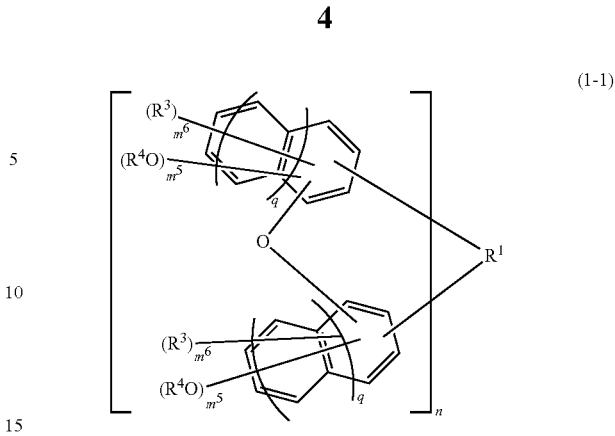

(1-1)

wherein $R^1$, n and q are the same as defined above, each $R^3$ independently represents a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, or a thiol group, and may be the same or different in the same naphthalene ring or benzene ring, each $R^4$ independently represents a hydrogen atom or an acid-dissociable group, in which at least one $R^4$ represents an acid-dissociable group, each $m^5$ is independently an integer of 1 to 6, each $m^6$ is independently an integer of 0 to 5, and $m^3+m^6$ is an integer of 1 to 6.

[3]

The material for forming the underlayer film for lithography according to [2], wherein the compound represented by the formula (1-1) is a compound represented by following formula (1-2),

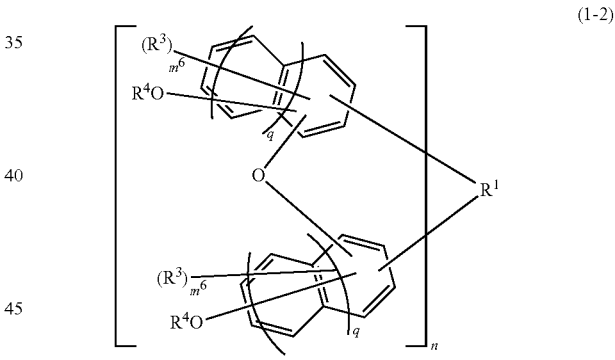

(1-2)

wherein $R^1$, $R^3$, $R^4$, $m^6$, n and q are the same as defined above, provided that at least one $R^4$ represents an acid-dissociable group.

[4]

The material for forming the underlayer film for lithography according to [3], wherein the compound represented by the formula (1) is a compound represented by following formula (1-3),

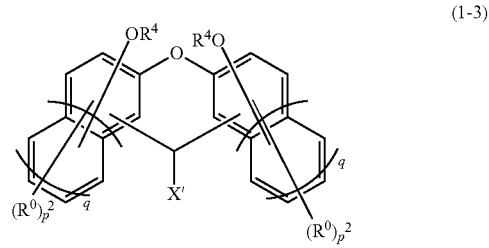

(1-3)

wherein $R^4$ and q are the same as defined above, X' represents a hydrogen atom, a halogen atom, or a monovalent group having 1 to 59 carbon atoms, each $R^0$ independently represents an alkyl group having 1 to 4 carbon atoms, or a halogen atom, and may be the same or different in the same naphthalene ring or benzene ring, and each $p^2$ is independently an integer of 0 to 5, provided that at least one $R^4$ represents an acid-dissociable group.

[5]

The material for forming the underlayer film for lithography according to [4], wherein q in the formula (1-3) is 1.

[6]

The material for forming the underlayer film for lithography according to [5], wherein the compound is represented by following formula (1-5) or following formula (1-6), (1-5)

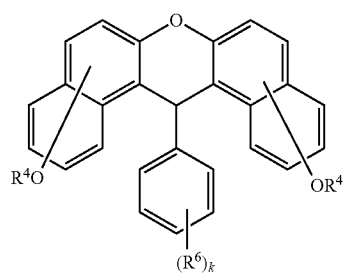

(1-6)

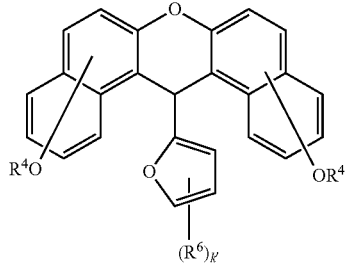

wherein $R^4$ is the same as defined above, $R^6$ represents at least one selected from the group consisting of a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, a thiol group and a hydroxyl group, k is an integer of 1 to 5, and k' is an integer of 1 to 3, provided that at least one $R^4$ represents an acid-dissociable group.

[7]

The material for forming the underlayer film for lithography according to any of [1] to [6], wherein the compound has a group including an iodine atom.

[8]

The material for forming the underlayer film for lithography according to [6], wherein the compound represented by the formula (1-5) or the formula (1-6) is at least one selected from the group consisting of following compounds.

(A-1-BOC)

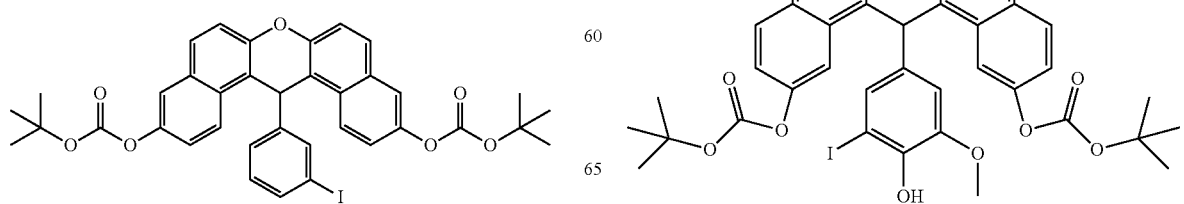

(A-1-MeBOC)

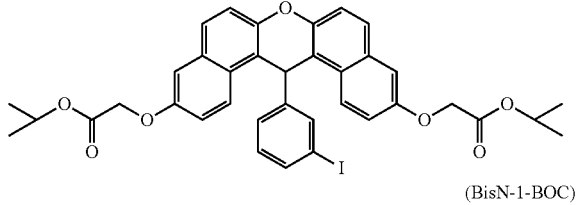

(BisN-1-BOC)

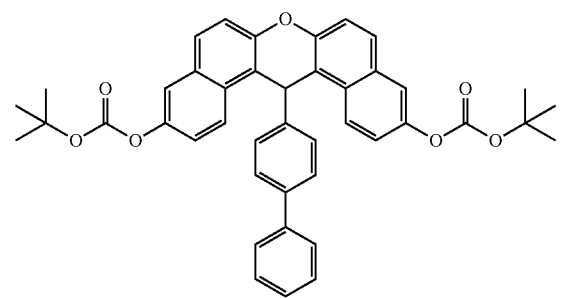

(A-2-BOC)

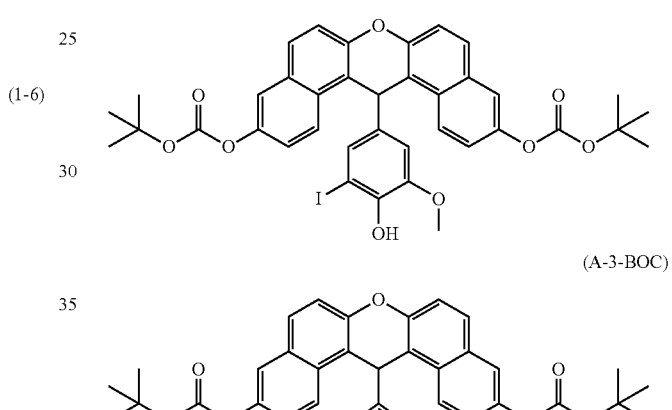

(A-3-BOC)

(B-1-BOC)

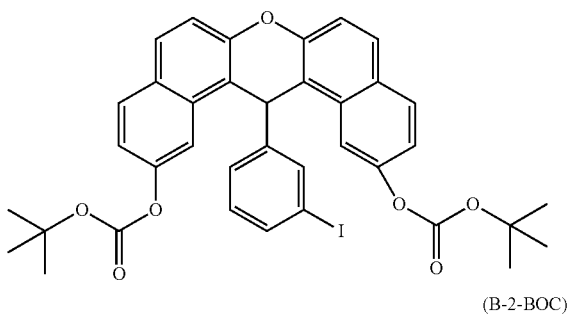

(B-2-BOC)

-continued (B-3-BOC)

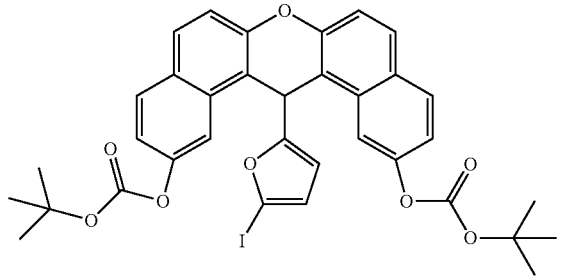

[9]
A composition for forming an underlayer film for lithography, comprising the material for forming the underlayer film for lithography according to any of [1] to [8], and a solvent.

[10]
The composition for forming the underlayer film for lithography according to [9], further comprising an acid generator.

[11]
The composition for forming the underlayer film for lithography according to [9] or [10], further comprising a crosslinking agent.

[12]
An underlayer film for lithography, formed from the composition for forming the underlayer film for lithography according to any of [9] to [11].

[13]
A method for producing an underlayer film for lithography, comprising forming an underlayer film on a substrate by using the composition for forming the underlayer film for lithography according to any of [9] to [11].

[14]
A resist pattern forming method comprising
a step of forming an underlayer film on a substrate by using the composition for forming the underlayer film for lithography according to any of [9] to [11],
a step of forming at least one photoresist layer on the underlayer film, and
a step of irradiating a predetermined region of the photoresist layer with radiation, and developing it.

[15]
A circuit pattern forming method comprising
a step of forming an underlayer film on a substrate by using the composition for forming the underlayer film for lithography according to any of [9] to [11],
a step of forming an intermediate layer film on the underlayer film by using a silicon atom-containing resist intermediate layer film material,
a step of forming at least one photoresist layer on the intermediate layer film,
a step of irradiating a predetermined region of the photoresist layer with radiation, and developing it to form a resist pattern,
a step of etching the intermediate layer film with the resist pattern as a mask, to form an intermediate layer film pattern,
a step of etching the underlayer film with the intermediate layer film pattern as an etching mask, to form an underlayer film pattern, and
a step of etching the substrate with the underlayer film pattern as an etching mask, to form a pattern on the substrate.

[16]
A resin comprising a structural unit derived from a compound represented by following formula (1),

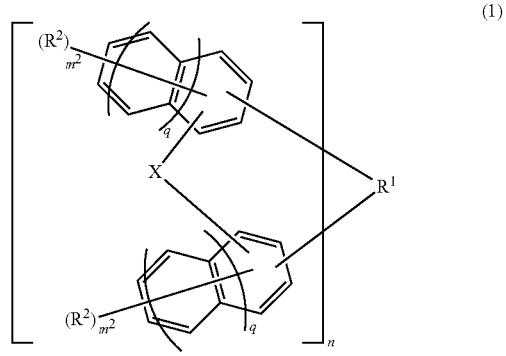

wherein $R^1$ represents a 2n-valent group having 1 to 60 carbon atoms, or a single bond, each $R^2$ independently represents a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, a thiol group, a hydroxyl group, or a group where a hydrogen atom of a hydroxyl group is substituted with an acid-dissociable group, and may be the same or different in the same naphthalene ring or benzene ring, in which at least one $R^2$ represents a group where a hydrogen atom of a hydroxyl group is substituted with an acid-dissociable group, n is an integer of 1 to 4, and structural formulae of n structural units in square brackets [ ] may be the same or different when n is an integer of 2 or more, X represents an oxygen atom, a sulfur atom, or a non-bridging group, each $m^2$ is independently an integer of 0 to 7, provided that at least one $m^2$ is an integer of 1 to 7, and each q is independently 0 or 1.

[17]
A purification method comprising
a step of providing a solution (A) by dissolving a compound represented by following formula (1) or a resin including a structural unit derived from a compound represented by the following formula (1) in a solvent, and
a first extraction step of bringing the resulting solution (A) into contact with an acidic aqueous solution, to extract impurities in the solution (A), wherein
the solvent to be used in the step of providing the solution (A) comprises an organic solvent optionally immiscible with water,

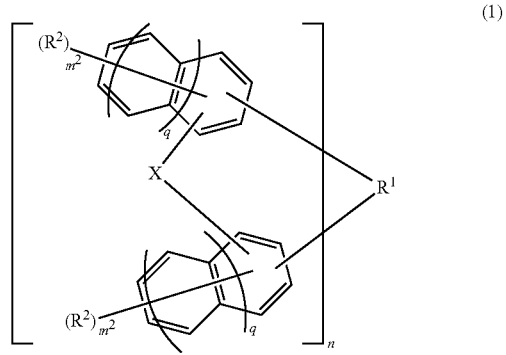

wherein R¹ represents a 2n-valent group having 1 to 60 carbon atoms, or a single bond, each R² independently represents a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, a thiol group, a hydroxyl group, or a group where a hydrogen atom of a hydroxyl group is substituted with an acid-dissociable group, and may be the same or different in the same naphthalene ring or benzene ring, in which at least one R² represents a group where a hydrogen atom of a hydroxyl group is substituted with an acid-dissociable group, n is an integer of 1 to 4, and structural formulae of n structural units in square brackets [ ] may be the same or different when n is an integer of 2 or more, X represents an oxygen atom, a sulfur atom, or a non-bridging group, each m² is independently an integer of 0 to 7, provided that at least one m² is an integer of 1 to 7, and each q is independently 0 or 1.

[18]

The purification method according to [17], wherein
the acidic aqueous solution is an aqueous mineral acid solution or an aqueous organic acid solution,
the aqueous mineral acid solution is an aqueous solution of at least one mineral acid selected from the group consisting of hydrochloric acid, sulfuric acid, nitric acid and phosphoric acid, and
the aqueous organic acid solution is an aqueous solution of at least one organic acid selected from the group consisting of acetic acid, propionic acid, oxalic acid, malonic acid, succinic acid, fumaric acid, maleic acid, tartaric acid, citric acid, methanesulfonic acid, phenolsulfonic acid, p-toluenesulfonic acid and trifluoroacetic acid.

[19]

The purification method according to [17] or [18], wherein the organic solvent optionally immiscible with water is at least one organic solvent selected from the group consisting of toluene, 2-heptanone, cyclohexanone, cyclopentanone, methyl isobutyl ketone, propylene glycol monomethyl ether acetate and ethyl acetate.

[20]

The purification method according to any of [17] to [19], further comprising, after the first extraction step, a second extraction step of further bringing the solution (A) into contact with water, to further extract impurities in the solution (A).

The material for forming an underlayer film for lithography according to the present invention can be applied to a wet process and enables a photoresist underlayer film excellent in heat resistance and etching resistance to be formed.

DESCRIPTION OF EMBODIMENTS

Hereinafter, an embodiment (hereinafter, referred to as "the present embodiment") of the present invention will be described. It is to be noted that the following present embodiments are illustrative for describing the present invention, and the present invention is not limited only to such embodiments.

[Material for Forming Underlayer Film for Lithography]

A material for forming an underlayer film for lithography of the present embodiment contains at least any of a compound represented by the following formula (1) or a resin including a structural unit derived from a compound represented by the following formula (1).

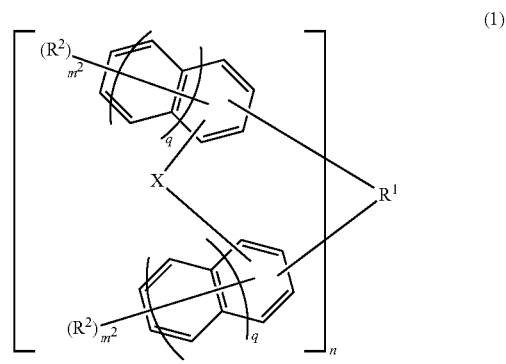

(in formula (1), R¹ represents a 2n-valent group having 1 to 60 carbon atoms, or a single bond, each R² independently represents a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, a thiol group, a hydroxyl group, or a group where a hydrogen atom of a hydroxyl group is substituted with an acid-dissociable group, and may be the same or different in the same naphthalene ring or benzene ring, in which at least one R² represents a group where a hydrogen atom of a hydroxyl group is substituted with an acid-dissociable group, n is an integer of 1 to 4, and structural formulae of n structural units in square brackets [ ] may be the same or different when n is an integer of 2 or more, X represents an oxygen atom, a sulfur atom, or a non-bridging group, each m² is independently an integer of 0 to 7, provided that at least one m² is an integer of 1 to 7, and each q is independently 0 or 1.)

In the formula (1), X represents an oxygen atom, a sulfur atom, or a non-bridging group, and respective aromatic rings are bonded at any position via X.

R¹ represents a 2n-valent group having 1 to 60 carbon atoms, or a single bond, and respective aromatic rings are bonded at any position via R¹. The 2n-valent group means, for example, an alkylene group having 1 to 60 carbon atoms when n=1, an alkanetetrayl group having 1 to 60 carbon atoms when n=2, an alkanehexayl group having 2 to 60 carbon atoms when n=3, and an alkaneoctayl group having 3 to 60 carbon atoms when n=4. In addition, the 2n-valent group is not particularly limited, and examples thereof include those having a straight hydrocarbon group, a branched hydrocarbon group or an alicyclic hydrocarbon group. Herein, the alicyclic hydrocarbon group also includes a bridged alicyclic hydrocarbon group.

The 2n-valent group may also have a double bond, a hetero atom, or an aromatic group having 6 to 30 carbon atoms. Furthermore, the aromatic group may also have a cyano group, a nitro group, a heterocyclic group, a halogen atom, a straight aliphatic hydrocarbon group having 1 to 20 carbon atoms, a branched aliphatic hydrocarbon group having 3 to 20 carbon atoms, a cyclic aliphatic hydrocarbon group having 3 to 20 carbon atoms, an aryl group having 6 to 20 carbon atoms, an alkenyl group having 2 to 10 carbon atoms, an alkoxy group having 1 to 30 carbon atoms, a thiol group or a hydroxyl group.

Each R² independently represents a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, a thiol group, a hydroxyl group, or a group where a hydrogen atom of a hydroxyl group is substituted with an acid-dissociable group, and may be the same or different in the same naphthalene ring or benzene ring, provided that at least one $R^2$ in the formula (1) represents a group where a hydrogen atom of a hydroxyl group is substituted with an acid-dissociable group.

n is an integer of 1 to 4, and structural formulae of n structural units in square brackets [ ] may be the same or different when n is an integer of 2 or more. Each $m^2$ is independently an integer of 0 to 7, provided that at least one $m^2$ is an integer of 1 to 7. Each q is independently 0 or 1.

The compound represented by the formula (1) has a high heat resistance due to rigidity of its structure while having a relatively low molecular weight, and therefore it can be used even under a high-temperature baking condition. In addition, the compound has a relatively low molecular weight and a low viscosity, and therefore, even when being applied to a substrate having a step (in particular, fine space, hole pattern and the like), it can be easily filled uniformly in every part of the step, and as a result, a material for forming an underlayer film for lithography using such a compound can be improved in terms of embedding properties in a relatively advantageous manner. In addition, the compound includes an acid-dissociable group in its structure and has a low glass transition temperature as a substance because of having neither bendability due to a functional group constituting its molecule nor a hydroxyl group constituting a hydrogen bond, therefore, while keeping high embedding properties under a low-temperature baking condition, has a high heat resistance due to leaving of an acid-dissociable group under a high-temperature baking condition, and thus can be used even under a high-temperature baking condition. Furthermore, a high etching resistance is also imparted.

The "acid-dissociable group" herein means a characteristic group that is cleaved in the presence of an acid to generate the change of an alkali-soluble group or the like. The alkali-soluble group is not particularly limited, and examples thereof include a phenolic hydroxyl group, a carboxyl group, a sulfonic acid group, and a hexafluoroisopropanol group, a phenolic hydroxyl group and a carboxyl group are preferable, and a phenolic hydroxyl group is more preferable.

The acid-dissociable group is not particularly limited, and, for example, any group can be appropriately selected and adopted from those proposed with respect to a hydroxystyrene-based resin, a (meth)acrylic resin, and the like for use in a chemically amplified resist composition for KrF or ArF. Specifically, examples thereof include, but are not particularly limited, a substituted methyl group, a 1-substituted ethyl group, a 1-substituted-n-propyl group, a 1-branched alkyl group, a silyl group, an acyl group, a 1-substituted alkoxymethyl group, a cyclic ether group, an alkoxycarbonyl group, and an alkoxycarbonylalkyl group. The acid-dissociable group preferably has no crosslinkable functional group.

The substituted methyl group is not particularly limited, and examples thereof include a substituted methyl group having 2 to 20 carbon atoms, and a substituted methyl group having 4 to 18 carbon atoms is preferable and a substituted methyl group having 6 to 16 carbon atoms is further preferable. Specifically, examples thereof can include, but are not particularly limited, a methoxymethyl group, a methylthiomethyl group, an ethoxymethyl group, a n-propoxymethyl group, an isopropoxymethyl group, a n-butoxymethyl group, a t-butoxymethyl group, a 2-methylpropoxymethyl group, an ethylthiomethyl group, a methoxyethoxymethyl group, a phenyloxymethyl group, a 1-cyclopentyloxymethyl group, a 1-cyclohexyloxymethyl group, a benzylthiomethyl group, a phenacyl group, a 4-bromophenacyl group, a 4-methoxyphenacyl group, a piperonyl group, and a substituent represented by the following formula (13-1). Herein, $R^7$ in the following formula (13-1) is not particularly limited, and examples thereof include a methyl group, an ethyl group, an isopropyl group, a n-propyl group, a t-butyl group, and a n-butyl group.

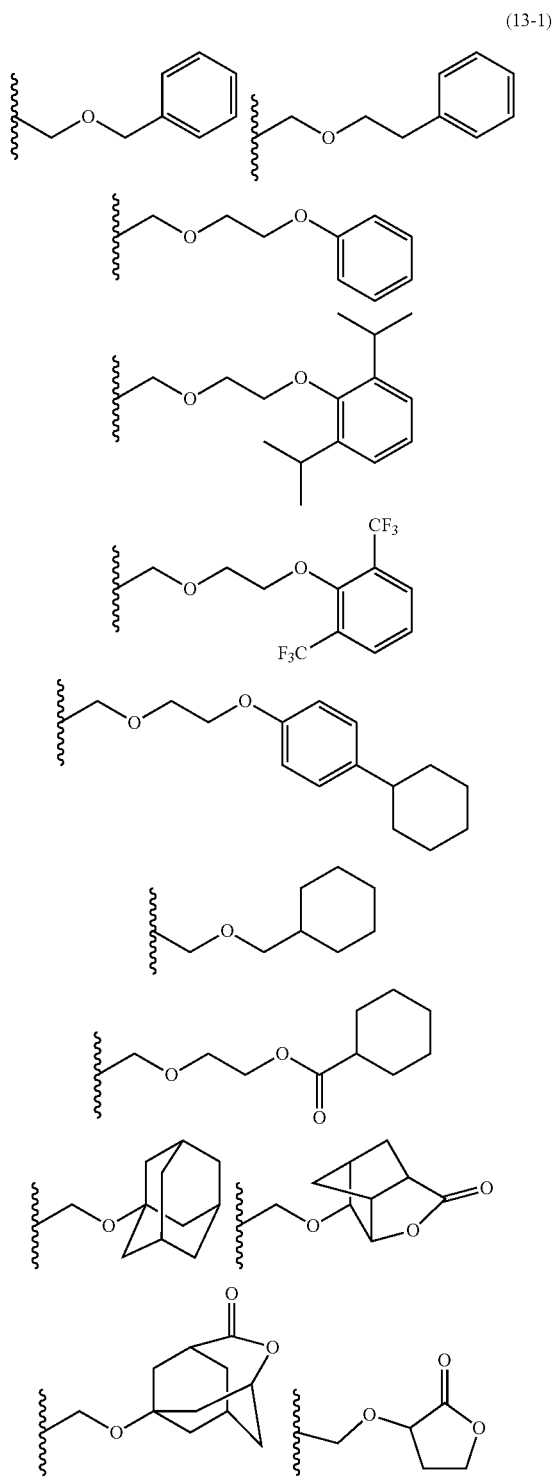

(13-1)

-continued

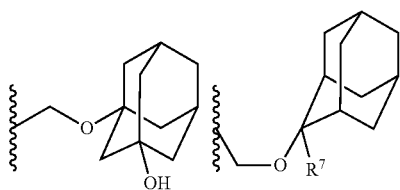

(in formula (13-1), $R^7$ represents an alkyl group having 1 to 4 carbon atoms.)

The 1-substituted ethyl group is not particularly limited, and examples thereof include a 1-substituted ethyl group having 3 to 20 carbon atoms, and a 1-substituted ethyl group having 5 to 18 carbon atoms is preferable and a substituted ethyl group having 7 to 16 carbon atoms is further preferable. Specifically, examples thereof can include, but are not particularly limited, a 1-methoxyethyl group, a 1-methylthioethyl group, a 1,1-dimethoxyethyl group, a 1-ethoxyethyl group, a 1-ethylthioethyl group, a 1,1-diethoxyethyl group, a n-propoxyethyl group, an isopropoxyethyl group, a n-butoxyethyl group, a t-butoxyethyl group, a 2-methylpropoxyethyl group, a 1-phenoxyethyl group, a 1-phenylthioethyl group, a 1,1-diphenoxyethyl group, a 1-cyclopentyloxyethyl group, a 1-cyclohexyloxyethyl group, a 1-phenylethyl group, a 1,1-diphenylethyl group, and a substituent represented by the following formula (13-2).

(13-2)

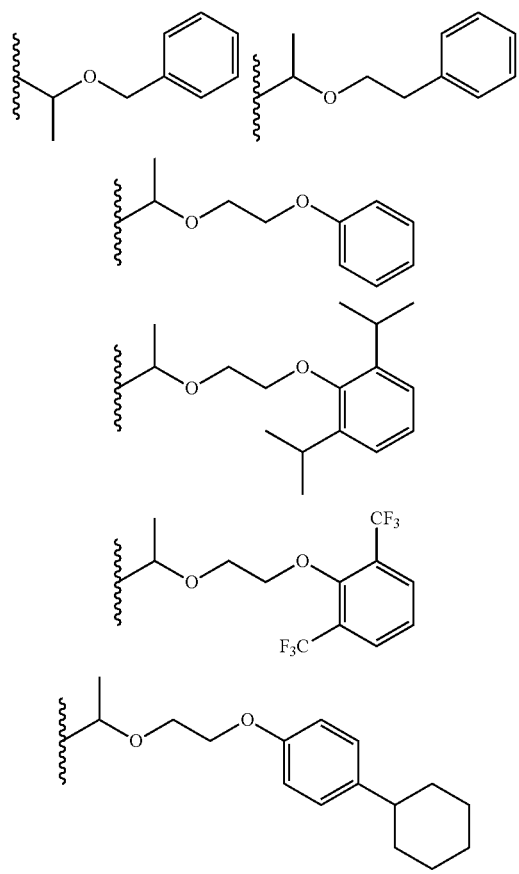

-continued

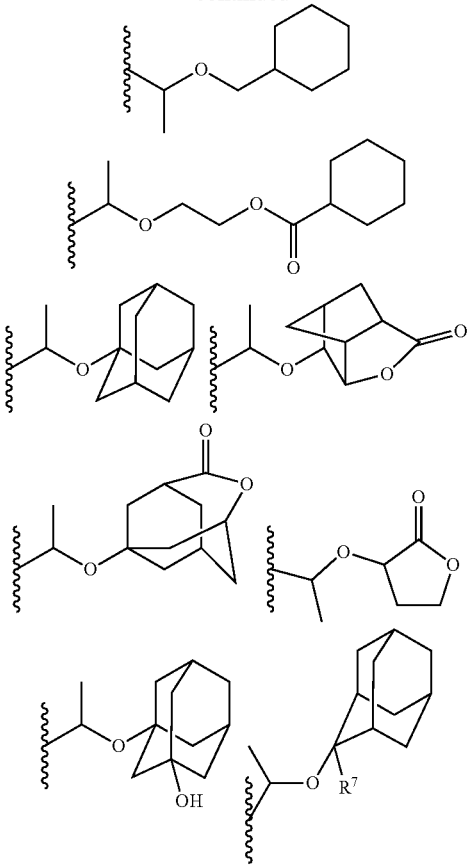

(in formula (13-2), $R^7$ is the same as defined in the formula (13-1).)

The 1-substituted-n-propyl group is not particularly limited, and examples thereof include a 1-substituted-n-propyl group having 4 to 20 carbon atoms, and a 1-substituted-n-propyl group having 6 to 18 carbon atoms is preferable and a 1-substituted-n-propyl group having 8 to 16 carbon atoms is further preferable. Specifically, examples thereof can include, but are not particularly limited, a 1-methoxy-n-propyl group and a 1-ethoxy-n-propyl group.

The 1-branched alkyl group is not particularly limited, and examples thereof include a 1-branched alkyl group having 3 to 20 carbon atoms, and a 1-branched alkyl group having 5 to 18 carbon atoms is preferable and a branched alkyl group having 7 to 16 carbon atoms is further preferable. Specifically, examples thereof can include, but are not particularly limited, an isopropyl group, a sec-butyl group, a tert-butyl group, a 1,1-dimethylpropyl group, a 1-methylbutyl group, a 1,1-dimethylbutyl group, a 2-methyladamantyl group, and a 2-ethyladamantyl group.

The silyl group is not particularly limited, and examples thereof include a silyl group having 1 to 20 carbon atoms, and a silyl group having 3 to 18 carbon atoms is preferable and a silyl group having 5 to 16 carbon atoms is further preferable. Specifically, examples thereof can include, but are not particularly limited, a trimethylsilyl group, an ethyldimethylsilyl group, a methyldiethylsilyl group, a triethylsilyl group, a tert-butyldimethylsilyl group, a tert-butyldiethylsilyl group, a tert-butyldiphenylsilyl group, a tri-tert-butylsilyl group and a triphenylsilyl group.

The acyl group is not particularly limited, and examples thereof include an acyl group having 2 to 20 carbon atoms, and an acyl group having 4 to 18 carbon atoms is preferable and an acyl group having 6 to 16 carbon atoms is further preferable. Specifically, examples thereof can include, but are not particularly limited, an acetyl group, a phenoxyacetyl group, a propionyl group, a butyryl group, a heptanoyl group, a hexanoyl group, a valeryl group, a pivaloyl group, an isovaleryl group, a lauryloyl group, an adamantylcarbonyl group, a benzoyl group, and a naphthoyl group.

The 1-substituted alkoxymethyl group is not particularly limited, and examples thereof include a 1-substituted alkoxymethyl group having 2 to 20 carbon atoms, and a 1-substituted alkoxymethyl group having 4 to 18 carbon atoms is preferable and a 1-substituted alkoxymethyl group having 6 to 16 carbon atoms is further preferable. Specifically, examples thereof can include, but are not particularly limited, a 1-cyclopentylmethoxymethyl group, a 1-cyclopentylethoxymethyl group, a 1-cyclohexylmethoxymethyl group, a 1-cyclohexylethoxymethyl group, a 1-cyclooctylmethoxymethyl group and a 1-adamantylmethoxymethyl group.

The cyclic ether group is not particularly limited, and examples thereof include a cyclic ether group having 2 to 20 carbon atoms, and a cyclic ether group having 4 to 18 carbon atoms is preferable and a cyclic ether group having 6 to 16 carbon atoms is further preferable. Specifically, examples thereof can include, but are not particularly limited, a tetrahydropyranyl group, a tetrahydrofuranyl group, a tetrahydrothiopyranyl group, a tetrahydrothiofuranyl group, a 4-methoxytetrahydropyranyl group and a 4-methoxytetrahydrothiopyranyl group.

The alkoxycarbonyl group is not particularly limited, and examples thereof include an alkoxycarbonyl group having 2 to 20 carbon atoms, and an alkoxycarbonyl group having 4 to 18 carbon atoms is preferable and an alkoxycarbonyl group having 6 to 16 carbon atoms is further preferable. Specifically, examples thereof can include, but are not particularly limited, a methoxycarbonyl group, an ethoxycarbonyl group, a n-propoxycarbonyl group, an isopropoxycarbonyl group, a n-butoxycarbonyl group, a tert-butoxycarbonyl group, or an acid-dissociable group represented by the following formula (13-3) where n=0.

The alkoxycarbonylalkyl group is not particularly limited, and examples thereof include an alkoxycarbonylalkyl group having 2 to 20 carbon atoms, and an alkoxycarbonylalkyl group having 4 to 18 carbon atoms is preferable and an alkoxycarbonylalkyl group having 6 to 16 carbon atoms is further preferable. Specifically, examples thereof can include, but are not particularly limited, a methoxycarbonylmethyl group, an ethoxycarbonylmethyl group, a n-propoxycarbonylmethyl group, an isopropoxycarbonylmethyl group, a n-butoxycarbonylmethyl group, or an acid-dissociable group represented by the following formula (13-3) where n=1 to 4.

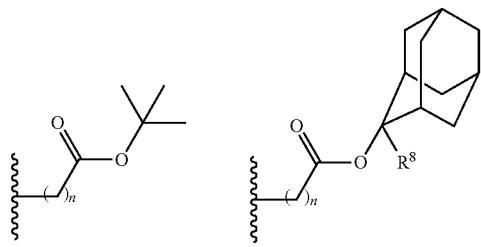

(13-3)

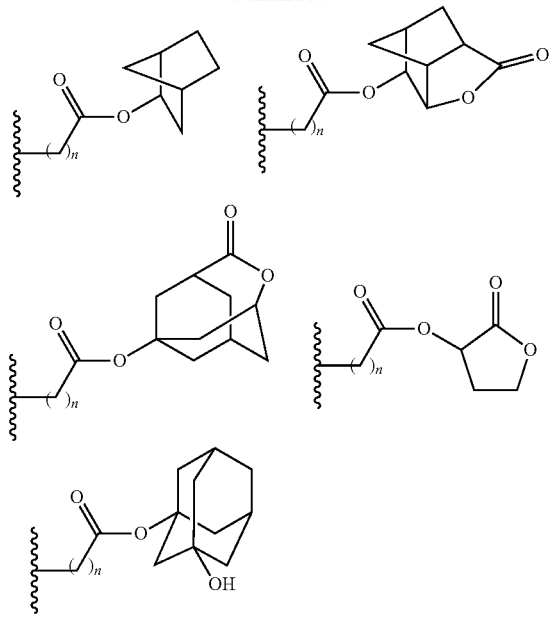

(in formula (13-3), $R^8$ represents a hydrogen atom, or a straight or branched alkyl group having 1 to 4 carbon atoms, and n is an integer of 0 to 4.)

Among such acid-dissociable groups, a substituted methyl group, a 1-substituted ethyl group, a 1-substituted alkoxymethyl group, a cyclic ether group, an alkoxycarbonyl group and an alkoxycarbonylalkyl group are preferable, a substituted methyl group, a 1-substituted ethyl group, an alkoxycarbonyl group and an alkoxycarbonylalkyl group are more preferable, and an acid-dissociable group having a structure selected from a cycloalkane having 3 to 12 carbon atoms, lactone, and a 6- to 12-membered aromatic ring is further preferable. The cycloalkane having 3 to 12 carbon atoms may be monocyclic or polycyclic, and is more preferably polycyclic. Specific examples are not particularly limited and include monocycloalkane, bicycloalkane, tricycloalkane and tetracycloalkane, and more specific examples are not particularly limited and include monocycloalkanes such as cyclopropane, cyclobutane, cyclopentane and cyclohexane, and polycycloalkanes such as adamantane, norbornane, isobornane, tricyclodecene and tetracyclodecane. Among them, adamantane, tricyclodecene and tetracyclodecane are preferable, and adamantane and tricyclodecene are particularly preferable. The cycloalkane having 3 to 12 carbon atoms may have a substituent. The lactone is not particularly limited, and examples thereof include butyrolactone, or a cycloalkane group having a lactone group and having 3 to 12 carbon atoms. The 6- to 12-membered aromatic ring is not particularly limited, and examples thereof include a benzene ring, a naphthalene ring, an anthracene ring, a phenanthrene ring and a pyrene ring, and a benzene ring and a naphthalene ring are preferable and a naphthalene ring is more preferable.

The acid-dissociable group is preferably an acid-dissociable group selected from groups represented by the following formula (13-4).

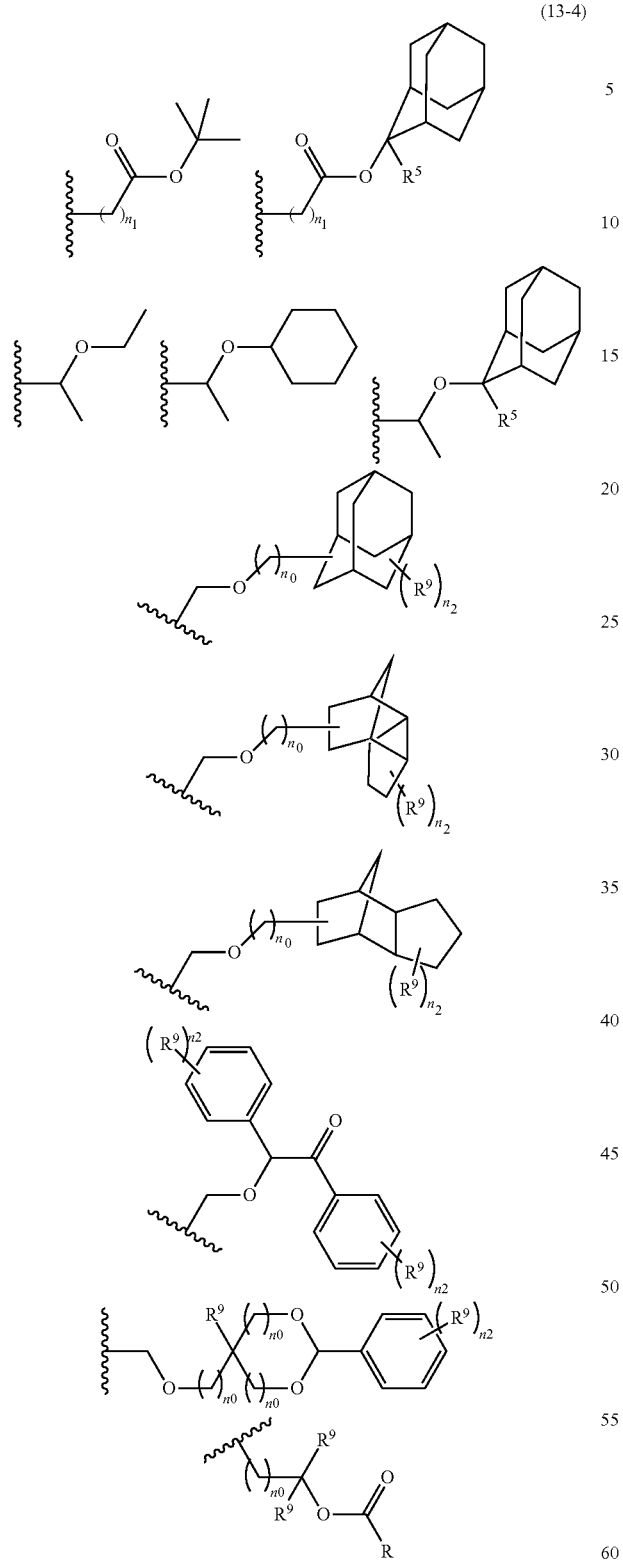

(13-4)

In formula (13-4), $R^5$ represents a hydrogen atom, or a straight or branched alkyl group having 1 to 4 carbon atoms, $R^9$ represents a hydrogen atom, a straight or branched alkyl group having 1 to 4 carbon atoms, a cyano group, a nitro group, a heterocyclic group, a halogen atom or a carboxyl group, n1 is an integer of 0 to 4, n2 is an integer of 1 to 5, and n0 is an integer of 0 to 4.

Hereinafter, specific examples of the compound represented by the formula (1) can be recited, but is not limited to those recited herein.

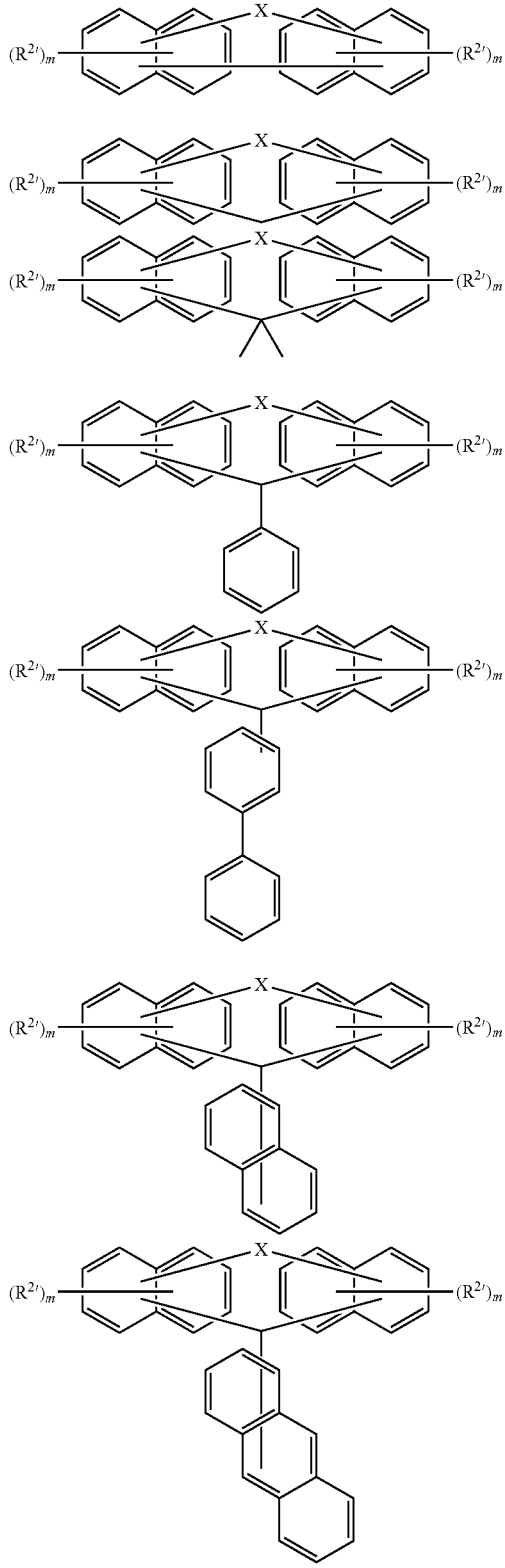

-continued
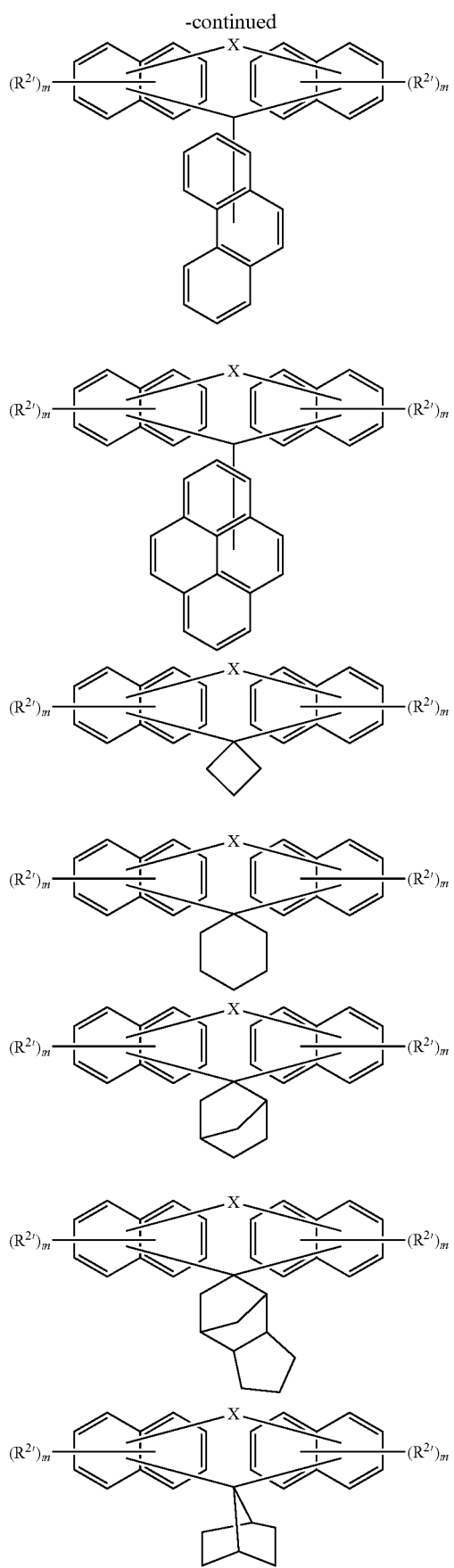
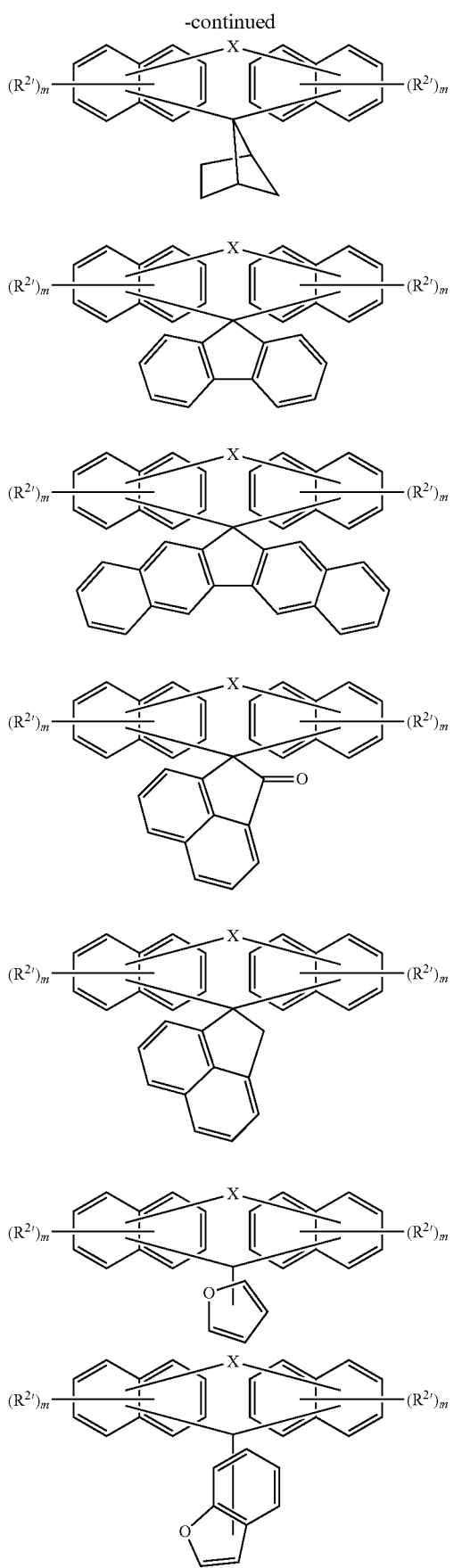

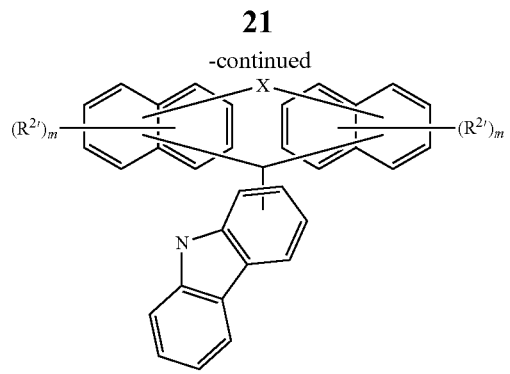
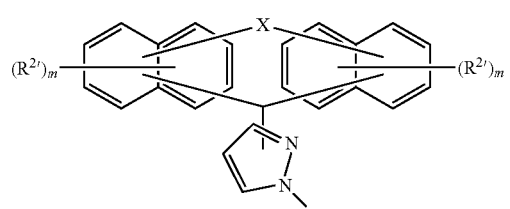
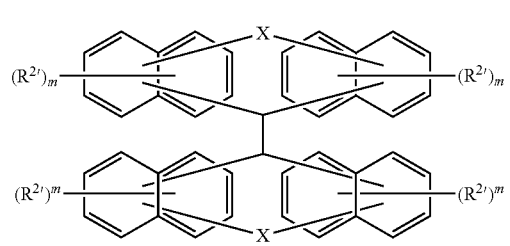
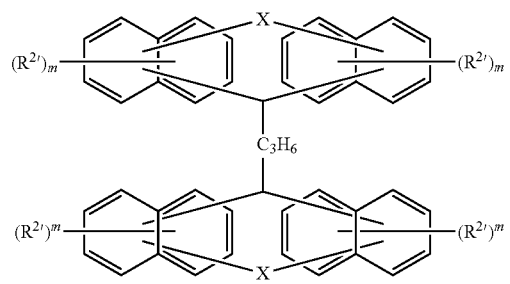
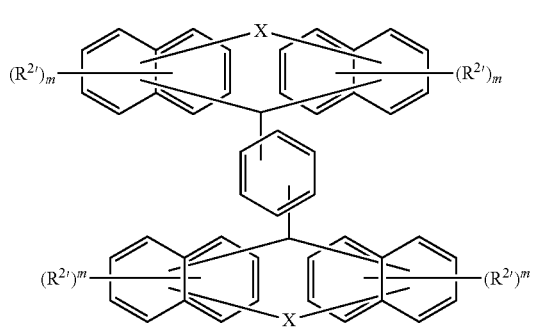
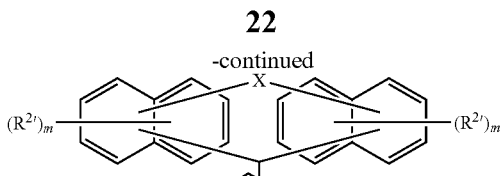
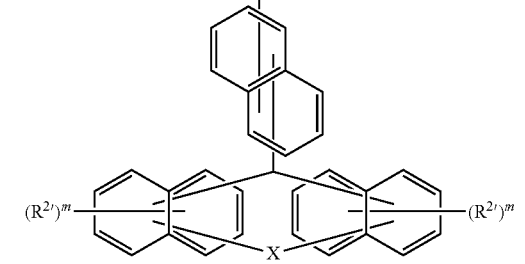
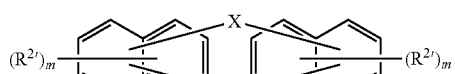
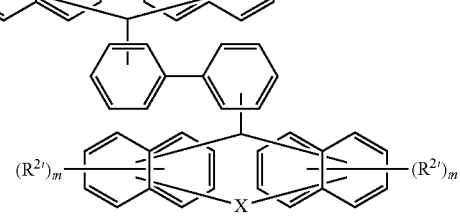
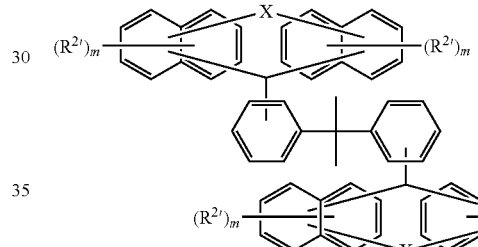
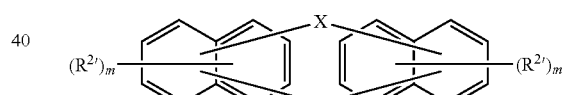
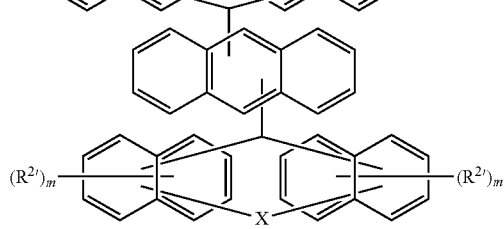
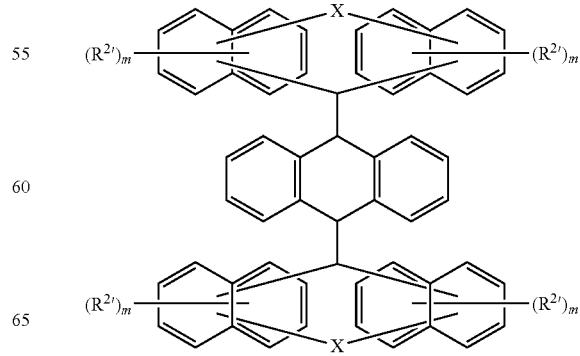

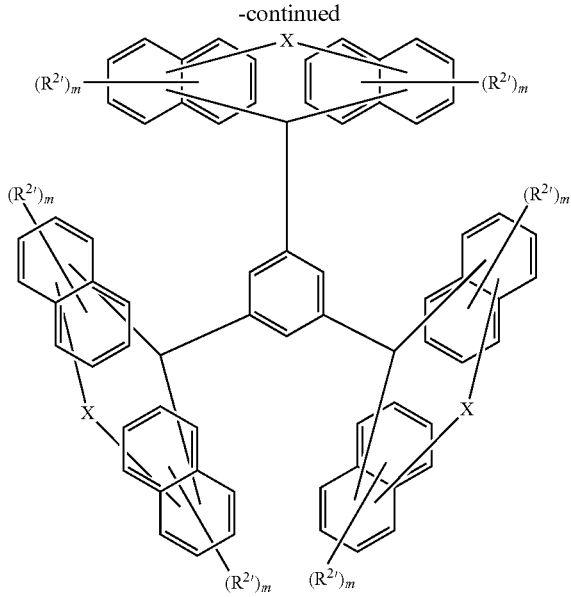
In the formulae, X is the same as defined in the formula (1), $R^{2'}$ is the same as $R^2$ defined in the formula (1), and each m is independently an integer of 0 to 7, provided that at least one m is an integer of 1 to 7 and at least one $R^{2'}$ represents a group where a hydrogen atom of a hydroxyl group is substituted with an acid-dissociable group.
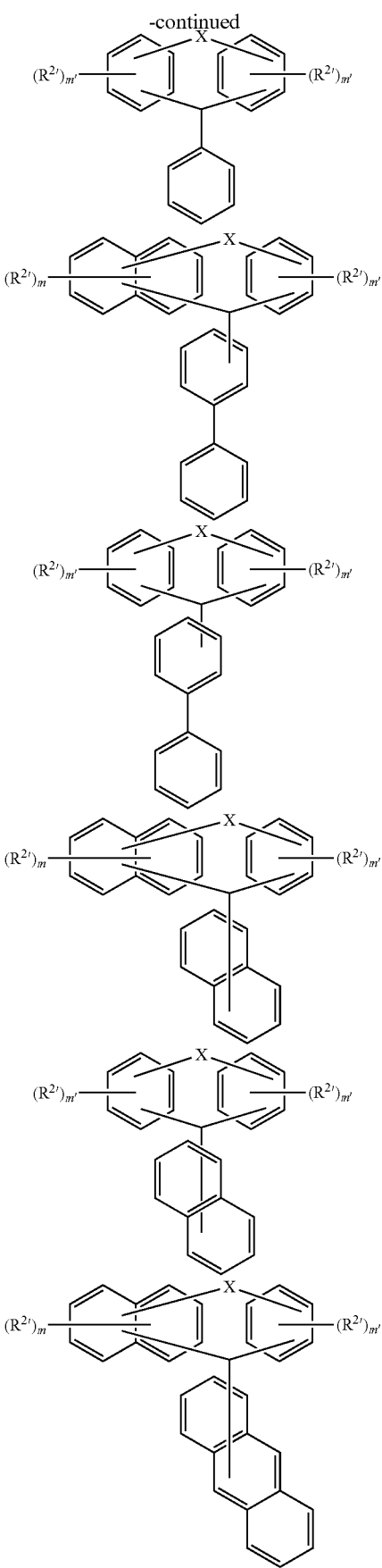

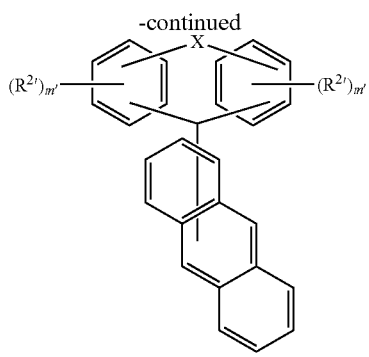

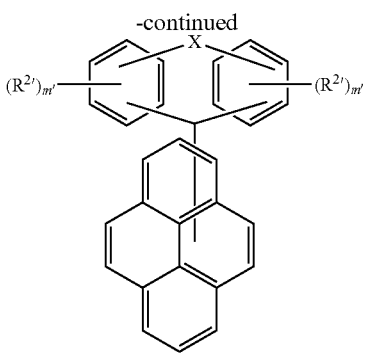

In the formulae, X is the same as defined in the formula (1), $R^{2'}$ is the same as $R^2$ defined in the formula (1), each m is independently an integer of 0 to 7, each m' is independently an integer of 0 to 4, provided that at least one m is an integer of 1 to 7, at least one m' is an integer of 1 to 7, and at least one $R^{2'}$ represents a group where a hydrogen atom of a hydroxyl group is substituted with an acid-dissociable group.

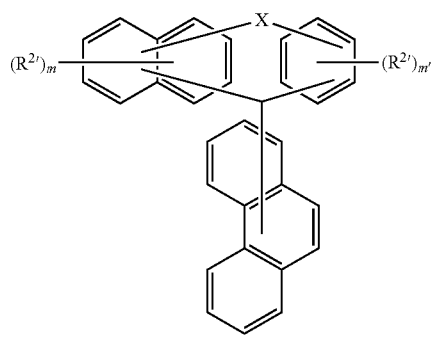

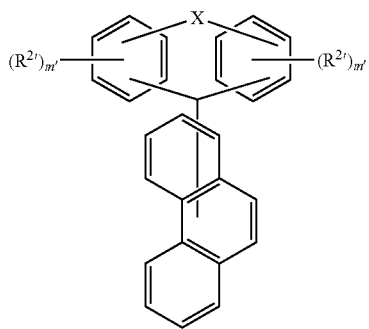

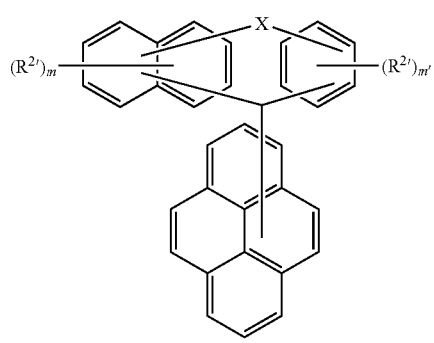

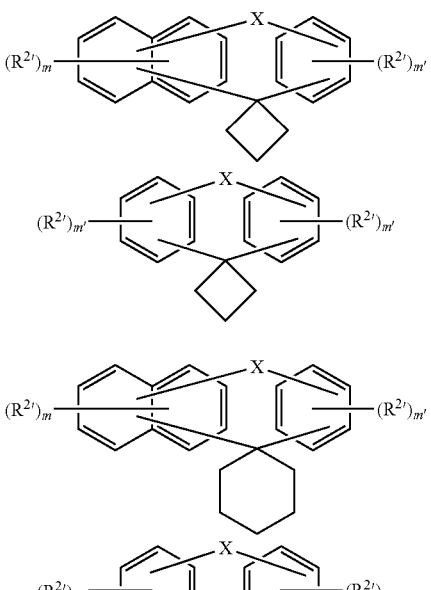

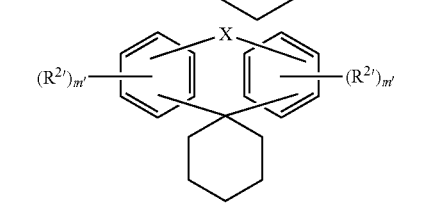

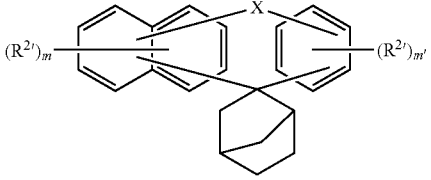

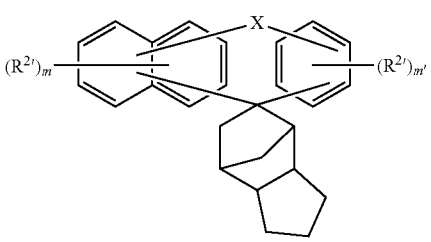

-continued

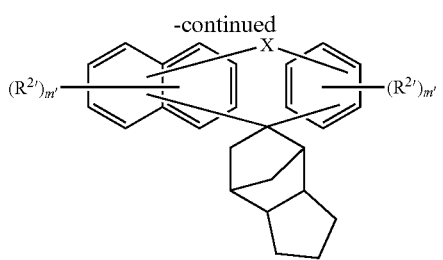

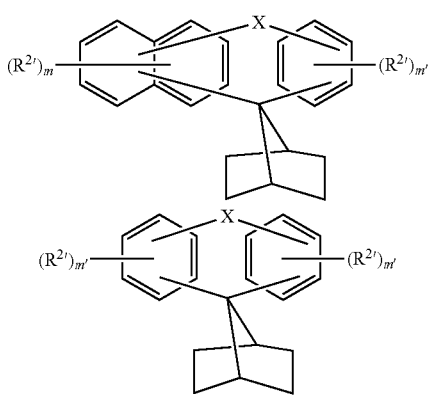

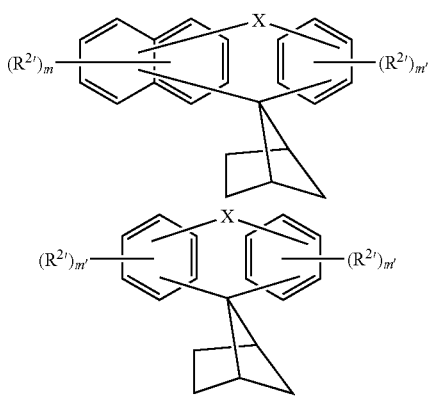

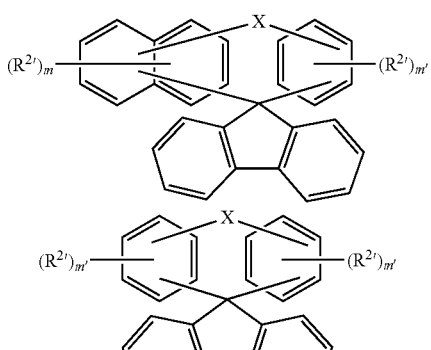

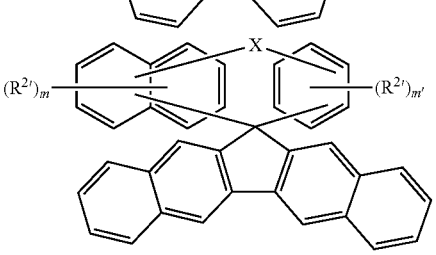

-continued

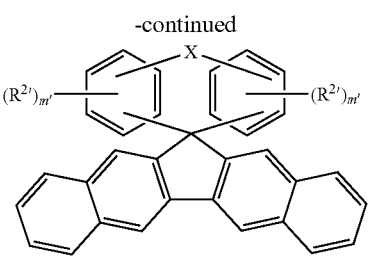

In the formulae, X is the same as defined in the formula (1), R²' is the same as R² defined in the formula (1), each m is independently an integer of 0 to 7, each m' is independently an integer of 0 to 4, provided that at least one m is an integer of 1 to 7, at least one m' is an integer of 1 to 7, and at least one R²' represents a group where a hydrogen atom of a hydroxyl group is substituted with an acid-dissociable group.

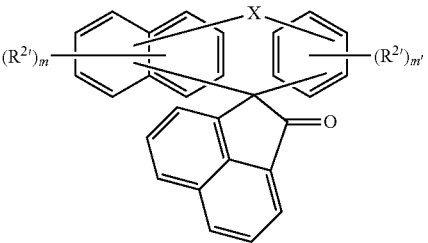

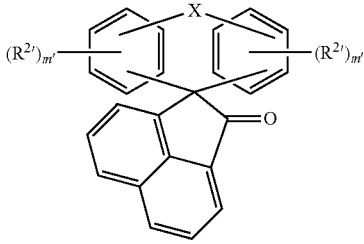

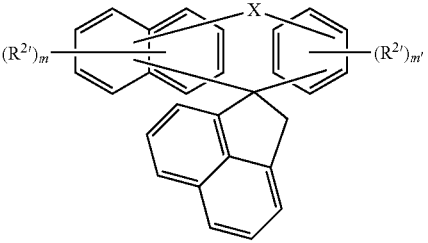

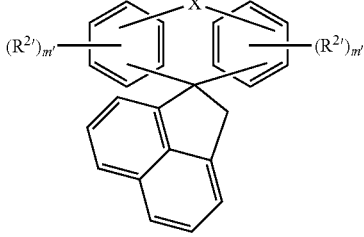

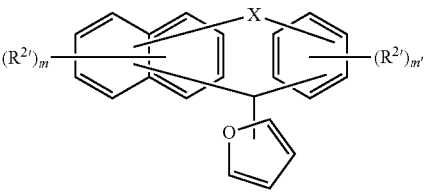

-continued

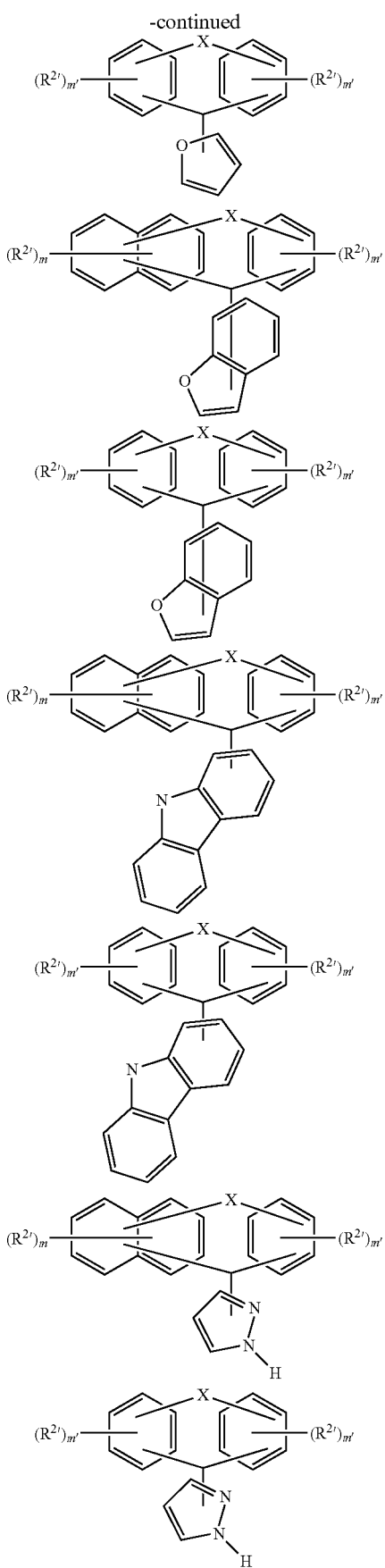

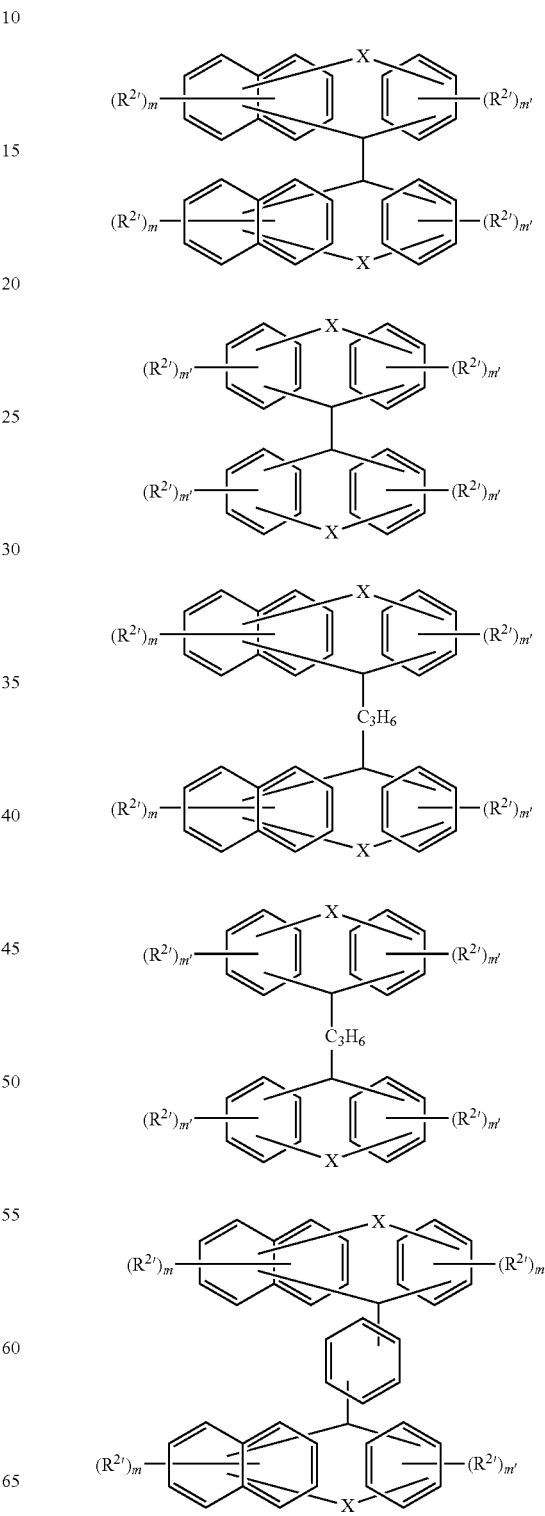

In the formulae, X is the same as defined in the formula (1), $R^{2'}$ is the same as $R^2$ defined in the formula (1), each m is independently an integer of 0 to 7, each m' is independently an integer of 0 to 4, provided that at least one m is an integer of 1 to 7, at least one m' is an integer of 1 to 7, and at least one $R^{2'}$ represents a group where a hydrogen atom of a hydroxyl group is substituted with an acid-dissociable group.

-continued
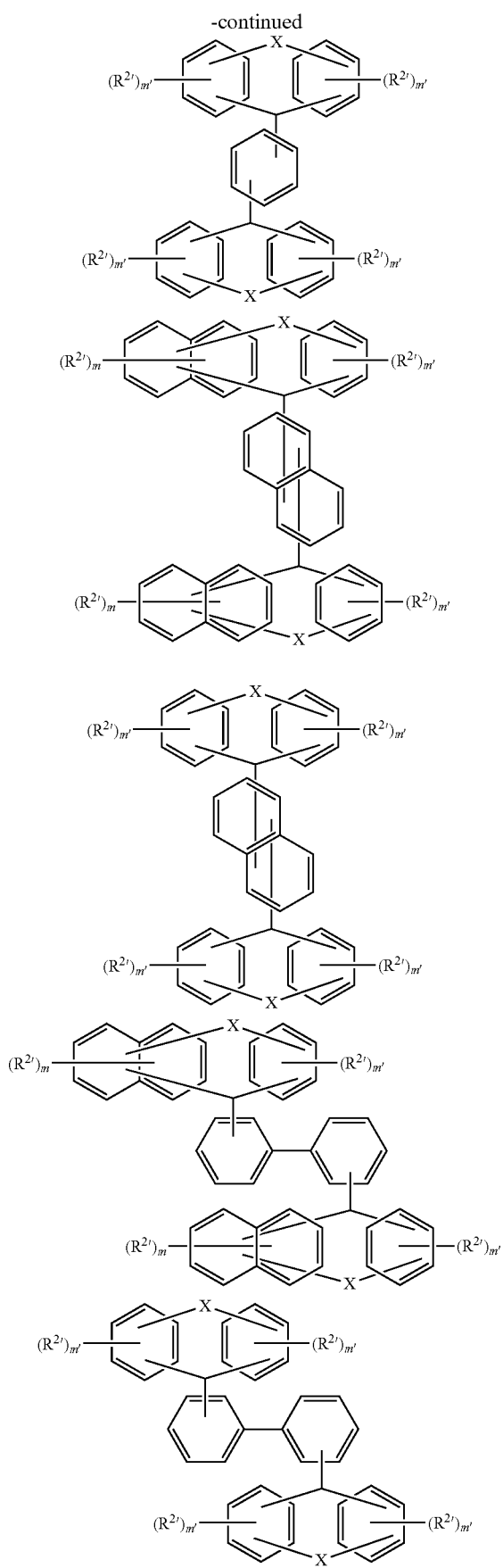
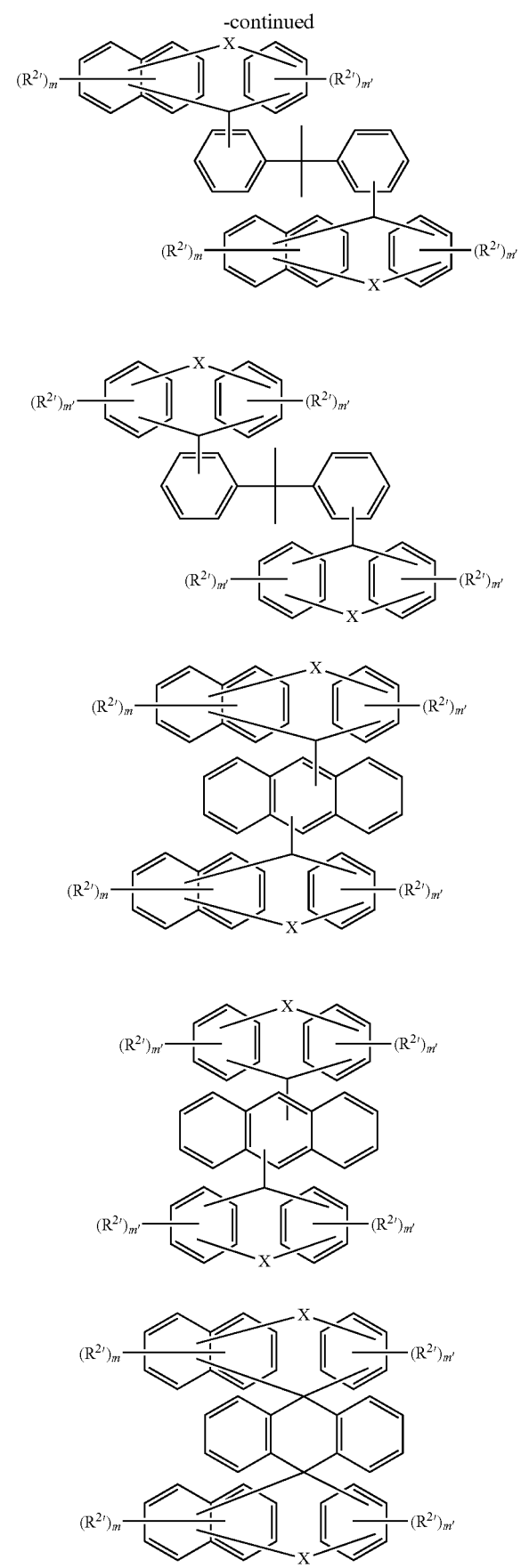

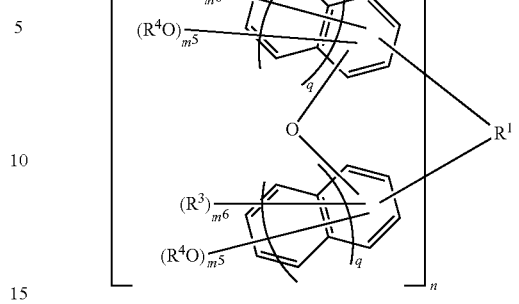

(1-1)

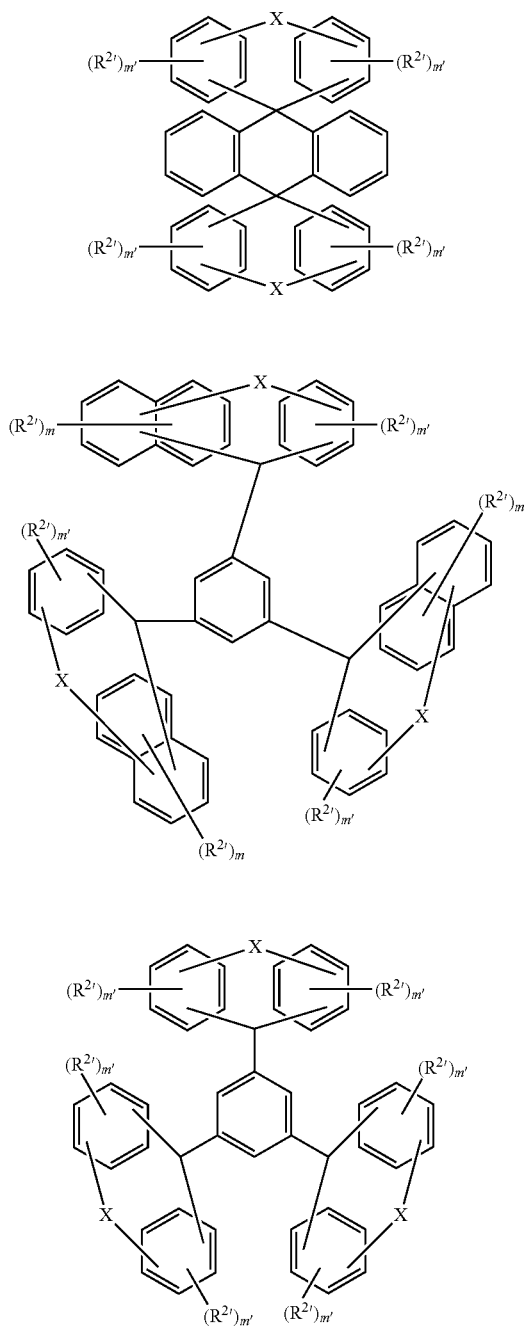

In the formulae, X is the same as defined in the formula (1), $R^{2'}$ is the same as $R^2$ defined in the formula (1), each m is independently an integer of 0 to 7, each m' is independently an integer of 0 to 4, provided that at least one m is an integer of 1 to 7, at least one m' is an integer of 1 to 7, and at least one $R^{2'}$ represents a group where a hydrogen atom of a hydroxyl group is substituted with an acid-dissociable group.

The compound represented by the formula (1) is preferably a compound where X in the formula (1) represents an oxygen atom in terms of feeding property of raw materials, and is preferably a compound represented by the following formula (1-1) in terms of solubility in an organic solvent.

In formula (1-1), $R^1$, n and q are the same as defined in the formula (1), each $R^3$ independently represents a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, or a thiol group, and may be the same or different in the same naphthalene ring or benzene ring. Each $R^4$ independently represents a hydrogen atom or an acid-dissociable group, each $m^5$ is independently an integer of 1 to 6, each $m^6$ is independently an integer of 0 to 5, and $m^3+m^6$ is an integer of 1 to 6, provided that at least one $R^4$ represents an acid-dissociable group.

The compound represented by the formula (1-1) is more preferably a compound represented by the following formula (1-2) in terms of solubility in an organic solvent.

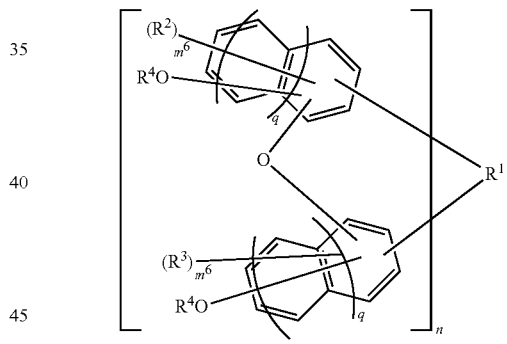

(1-2)

In formula (1-2), $R^1$, $R^3$, $R^4$, $m^6$, n and q are the same as defined in the formula (1-1).

In addition, the compound represented by formula (1-2) is further preferably a compound where n=1 in the formula (1-2) is satisfied, because such a compound has a low molecular weight, and a specific compound where n=1 in the formula (1-2) is satisfied is a compound represented by the following formula (1-3).

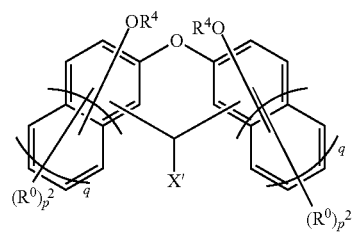

(1-3)

In formula (2), $R^4$ and q are the same as defined above. X' represents a hydrogen atom, a halogen atom, or a monovalent group having 1 to 59 carbon atoms, each $R^0$ independently represents an alkyl group having 1 to 4 carbon atoms, or a halogen atom, and may be the same or different in the same naphthalene ring or benzene ring. Each $p^2$ is independently an integer of 0 to 5, provided that at least one $R^4$ represents an acid-dissociable group.

In addition, the compound represented by the formula (1-3) is more further preferably a mode where q=1 in the formula (1-3) is satisfied, namely, a compound represented by the following formula (1-4), in terms of heat resistance.

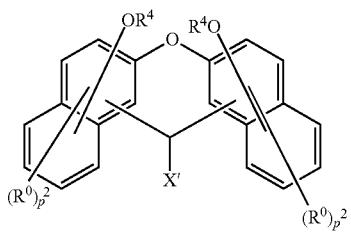

(1-4)

In formula (1-4), $R^0$, $R^4$, $p^2$ and X' are the same as defined above, provided that at least one $R^4$ represents an acid-dissociable group. In addition, in formula (1-4), X' preferably represents a hydrogen atom, a halogen atom, or a monovalent hydrocarbon group having 1 to 59 carbon atoms. Herein, the monovalent hydrocarbon group having 1 to 59 carbon atoms may also have a hetero atom.

Furthermore, the compound represented by the formula (1-4) is further more preferably a compound represented by the following formula (1-5) or the following formula (1-6). Such a xanthene compound can provide a material for forming an underlayer film for lithography, which is higher in the solubility in a high safe solvent and better in preservation stability and thin film formation, and which can impart a good pattern shape.

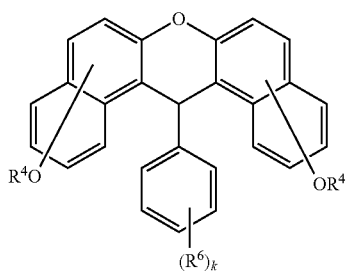

(1-5)

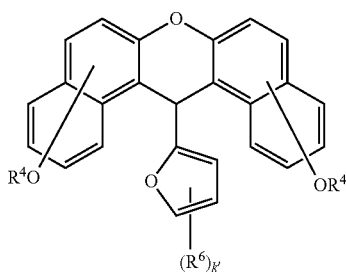

(1-6)

In the formula (1-5) and the formula (1-6), $R^4$ is the same as defined above, provided that at least one $R^4$ represents an acid-dissociable group. $R^6$ represents at least one selected from the group consisting of a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, a thiol group and a hydroxyl group. k is an integer of 1 to 5 and k' is an integer of 1 to 3.

The compound represented by the formula (1) preferably have a group including an iodine atom in terms of sensitivity during exposure, and, for example, in the formula (1), at least one selected from the group consisting of $R^1$ and $R^2$ represents a group including an iodine atom. Herein, the phrase "at least one selected from the group consisting of $R^1$ and $R^2$" means "at least one group selected from the group consisting of $R^1$ and $R^2$", and does not means "at least one kind of a group selected from the group consisting of $R^1$ and $R^2$".

The group including an iodine atom, with respect to $R^1$, is not particularly limited, and examples thereof include a straight hydrocarbon group having 1 to 60 carbon atoms, substituted with an iodine atom, a branched hydrocarbon group having 3 to 60 carbon atoms, substituted with an iodine atom, an alicyclic hydrocarbon group having 3 to 60 carbon atoms, substituted with an iodine atom, an aromatic group having 6 to 60 carbon atoms, substituted with an iodine atom, or a group having an aromatic group having 6 to 60 carbon atoms, substituted with an iodine atom. A branched hydrocarbon group having 3 to 60 carbon atoms, substituted with an iodine atom, an alicyclic hydrocarbon group having 3 to 60 carbon atoms, substituted with an iodine atom, an aromatic group having 6 to 60 carbon atoms, substituted with an iodine atom, or a group having an aromatic group having 6 to 60 carbon atoms, substituted with an iodine atom, is preferable, an alicyclic hydrocarbon group having 3 to 60 carbon atoms, substituted with an iodine atom, an aromatic group having 6 to 60 carbon atoms, substituted with an iodine atom, or a group having an aromatic group having 6 to 60 carbon atoms, substituted with an iodine atom, is more preferable, and a group having an aromatic group having 6 to 60 carbon atoms, substituted with an iodine atom, is further preferable, in terms of heat resistance.

The group including an iodine atom, with respect to $R^2$, is not particularly limited, and examples thereof include an iodine atom, a straight hydrocarbon group having 1 to 6 carbon atoms, substituted with an iodine atom, a branched hydrocarbon group having 3 to 6 carbon atoms, substituted with an iodine atom, a cyclic aliphatic hydrocarbon group having 3 to 6 carbon atoms, substituted with an iodine atom, or an aryl group having 6 carbon atoms, substituted with an iodine atom. The group including an iodine atom is preferably an iodine atom, a straight hydrocarbon group having 1 to 6 carbon atoms, substituted with an iodine atom, or a branched hydrocarbon group having 3 to 6 carbon atoms, substituted with an iodine atom, more preferably an iodine atom, or a straight hydrocarbon group having 1 to 6 carbon atoms, substituted with an iodine atom, in terms of solubility in a safe solvent, and the like. An iodine atom is further preferable.

The compound to be used in the present embodiment has a naphthalene backbone, and therefore exerts effects of being excellent in heat resistance and also excellent in not only heat resistance, but also solubility in a safe solvent. The positions of hydroxyl groups on the naphthalene ring are not particularly limited, and are preferably the 1,5-positions, 1,6-positions, the 1,7-positions, the 2,3-positions, the 2,7-positions, or the 2,6-positions in terms of industrial applicability of raw materials, more preferably the 2,6-positions in terms of a higher solubility in a safe solvent and a low crystallinity.

The compound represented by the formula (1-5) or the formula (1-6) is, in particular, extremely preferably at least one selected from the group consisting of the following compounds from the viewpoint that the effects of the present invention are more certainly exerted.

(A-1-BOC)
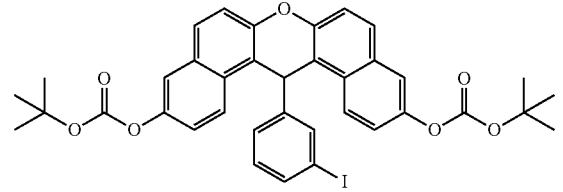

(A-1-MeBOC)
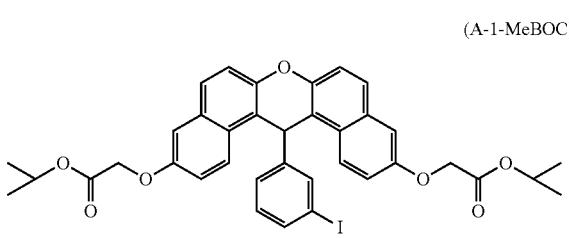

(BisN-1-BOC)
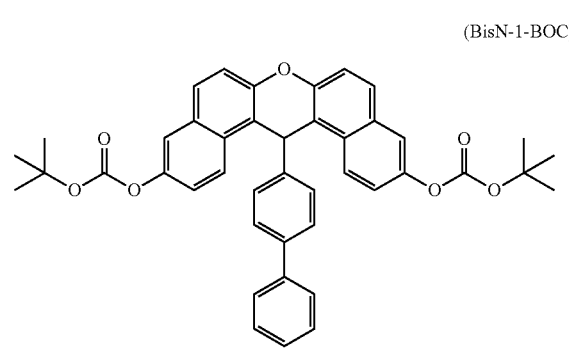

(A-2-BOC)
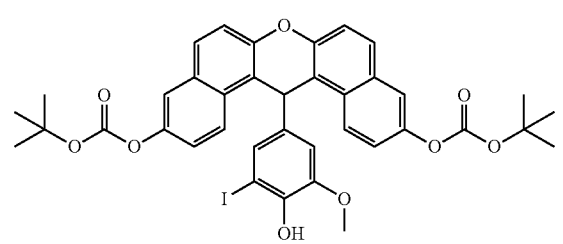

(A-3-BOC)
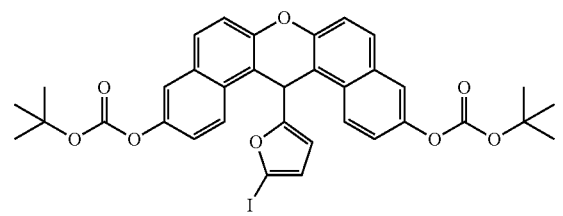

(B-1-BOC)
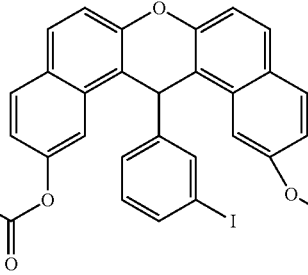

(B-2-BOC)
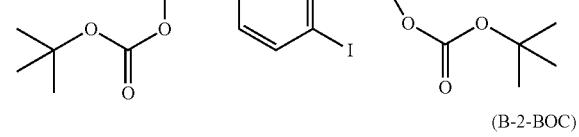

(B-3-BOC)
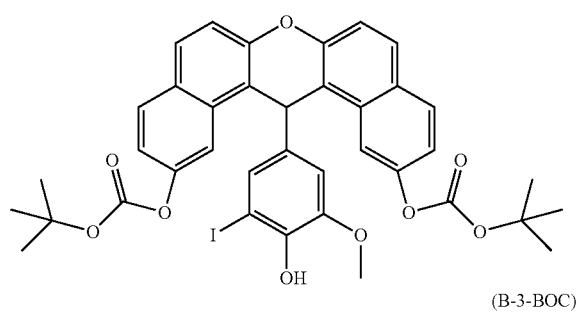

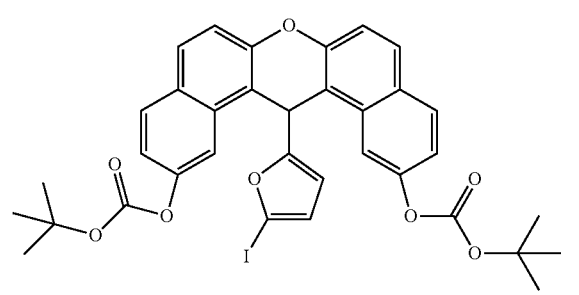

[Resin]

A resin of the present embodiment is a resin obtained with a compound represented by the following formula (1) as a monomer, and includes a structural unit derived from a compound represented by the following formula (1). The resin of the present embodiment is obtained by, for example, reacting a compound represented by the following formula (1) with a compound having crosslinking reactivity.

(1)
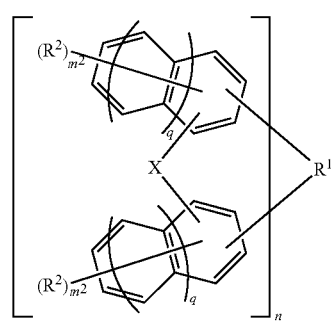

(in formula (1), $R^1$ represents a 2n-valent group having 1 to 60 carbon atoms, or a single bond, each $R^2$ independently represents a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, a thiol group, a hydroxyl group, or a group where a hydrogen atom of a hydroxyl group is substituted with an acid-dissociable group, and may be the same or different in the same naphthalene ring or benzene ring, in which at least one $R^2$ represents a group where a hydrogen atom of a hydroxyl group is substituted with an acid-dissociable group, n is an integer of 1 to 4, and structural formulae of n structural units in square brackets [ ] may be the same or different when n is an integer of 2 or more, X represents an oxygen atom, a sulfur atom, or a non-bridging group, each $m^2$ is independently an integer of 0 to 7, provided that at least one $m^2$ is an integer of 1 to 7, and each q is independently 0 or 1.)

The compound having crosslinking reactivity is not particularly limited as long as it can provide an oligomer or a polymer of the compound represented by the formula (1), and known one can be used therefor. Specific examples thereof include aldehyde, ketone, carboxylic acid, carboxylic halide, a halogen-containing compound, an amino compound, an imino compound, isocyanate, and an unsaturated hydrocarbon group-containing compound, but are not limited thereto.

The material for forming an underlayer film for lithography of the present embodiment contains at least one substance selected from the group consisting of the compound represented by the formula (1) and the resin including the structural unit derived from the compound. In the present embodiment, the content of the substance in the material for forming an underlayer film for lithography is preferably 1 to 100% by mass, more preferably 10 to 100% by mass, further preferably 50 to 100% by mass, more further preferably 100% by mass in terms of coatability and quality stability.

The material for forming an underlayer film for lithography of the present embodiment can be applied to a wet process, and is excellent in heat resistance and etching resistance. Furthermore, since the material for forming an underlayer film for lithography of the present embodiment is formed using the substance, the material can be used to form an underlayer film whose degradation is suppressed at high-temperature baking and which is also excellent in etching resistance to oxygen plasma etching or the like. Furthermore, the material for forming an underlayer film for lithography of the present embodiment is also excellent in adhesiveness with a resist layer, and therefore can form an excellent resist pattern. Herein, the material for forming an underlayer film for lithography of the present embodiment may also include a known material for forming an underlayer film for lithography as long as the effect of the present embodiment is not impaired.

[Composition for Forming Underlayer Film for Lithography]

A composition for forming an underlayer film for lithography of the present embodiment contains the material for forming an underlayer film for lithography, and a solvent.

[Solvent]

A known solvent can be appropriately used as the solvent to be used in the present embodiment as long as it dissolves at least the compound represented by the formula (1) and/or the resin including the compound as a constituent component.

Specific examples of the solvent include ketone-based solvents such as acetone, methyl ethyl ketone, methyl isobutyl ketone and cyclohexanone; cellosolve-based solvents such as propylene glycol monomethyl ether and propylene glycol monomethyl ether acetate; ester-based solvents such as ethyl lactate, methyl acetate, ethyl acetate, butyl acetate, isoamyl acetate, methyl methoxypropionate and methyl hydroxyisobutyrate; alcohol-based solvents such as methanol, ethanol, isopropanol and 1-ethoxy-2-propanol; and aromatic hydrocarbons such as toluene, xylene and anisole, but are not particularly limited thereto. These organic solvents can be used singly or in combinations of two or more thereof.

Among the solvents, particularly preferable are cyclohexanone, propylene glycol monomethyl ether, propylene glycol monomethyl ether acetate, ethyl lactate, methyl hydroxyisobutyrate, and anisole, in terms of safety.

The content of the solvent is not particularly limited, but it is preferably 100 to 10000 parts by mass, more preferably 200 to 5000 parts by mass, further preferably 200 to 1000 parts by mass based on 100 parts by mass of the material for forming an underlayer film, in terms of solubility and film formation.

[Crosslinking Agent]

The composition for forming an underlayer film for lithography of the present embodiment may further contain, if necessary, a crosslinking agent from the viewpoint of suppression of intermixing, and the like. Specific examples of the crosslinking agent usable in the present embodiment include, for example, a melamine compound, a guanamine compound, a glycoluril compound, a urea compound, an epoxy compound, a thioepoxy compound, an isocyanate compound, an azide compound, and a compound including a double bond such as an alkenyl ether group, these compounds being substituted with at least one group selected from a methylol group, an alkoxymethyl group and an acyloxymethyl group, as a substituent (crosslinkable group), but are not particularly limited thereto. Herein, these crosslinking agents can be used singly or in combinations of two or more thereof. Such a crosslinking agent can also be used as an additive. Herein, the crosslinkable group may also be introduced as a pendant group into a polymer side chain of the compound represented by the formula (1) and/or the resin including the compound as a constituent component. A compound including a hydroxy group can also be used as the crosslinking agent.

Specific examples of the melamine compound include, for example, hexamethylolmelamine, hexamethoxymethylmelamine, a compound in which 1 to 6 methylol groups in hexamethylolmelamine are methoxymethylated, or mixtures thereof, and hexamethoxyethylmelamine, hexaacyloxymethylmelamine, a compound in which 1 to 6 methylol groups in hexamethylolmelamine are acyloxymethylated, or mixtures thereof. Specific examples of the epoxy compound include, for example, tris(2,3-epoxypropyl)isocyanurate, trimethylolmethane triglycidyl ether, trimethylolpropane triglycidyl ether, and triethylolethane triglycidyl ether.

Specific examples of the guanamine compound include, for example, tetramethylolguanamine, tetramethoxymethylguanamine, a compound in which 1 to 4 methylol groups in tetramethylolguanamine are methoxymethylated, or mixtures thereof, and tetramethoxyethylguanamine, tetraacyloxyguanamine, a compound in which 1 to 4 methylol groups in tetramethylolguanamine are acyloxymethylated, or mixtures thereof. Specific examples of the glycoluril compound include, for example, tetramethylolglycoluril, tetramethoxyglycoluril, tetramethoxymethylglycoluril, a compound in which 1 to 4 methylol groups in tetramethylolglycoluril are methoxymethylated, or mixtures thereof, and a compound in which 1 to 4 methylol groups in tetramethylolglycoluril are acyloxymethylated, or mixtures thereof. Specific examples of the urea compound include, for example, tetramethylolurea, tetramethoxymethylurea, a compound in which 1 to 4 methylol groups in tetramethylolurea are methoxymethylated, or mixtures thereof, and tetramethoxyethylurea.

Specific examples of the compound including an alkenyl ether group include, for example, ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitol tetravinyl ether, and sorbitol pentavinyl ether.

In the material for forming an underlayer film for lithography according to the present embodiment, the content of the crosslinking agent is not particularly limited, but the content is preferably 5 to 50 parts by mass and more preferably 10 to 40 parts by mass based on 100 parts by mass of the material for forming an underlayer film. The content is set within the above preferable range to result in tendencies to suppress the occurrence of the mixing phenomenon with the resist layer, and to result in tendencies to enhance an antireflective effect and improve film formability after crosslinking.

[Acid Generator]

The composition for forming an underlayer film for lithography of the present embodiment may also further contain, if necessary, an acid generator from the viewpoint of further promoting a crosslinking reaction by heat. As the acid generator, one for generating an acid by pyrolysis and one for generating an acid by light irradiation are known, and any of them can be used.

The acid generator includes, for example:
1) an onium salt of the following general formula (P1a-1), (P1a-2), (P1a-3) or (P1b),
2) a diazomethane derivative of the following general formula (P2),
3) a glyoxime derivative of the following general formula (P3),
4) a bissulfone derivative of the following general formula (P4),
5) a sulfonic acid ester of an N-hydroxyimide compound of the following general formula (P5),
6) a β-ketosulfonic acid derivative,
7) a disulfone derivative,
8) a nitrobenzylsulfonate derivative, and
9) a sulfonic acid ester derivative, but is not particularly limited thereto. Herein, these acid generators can be used alone, or two or more thereof can be used in combination.

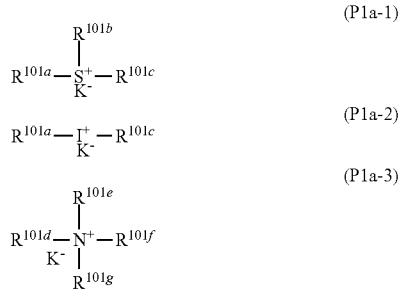

In the above formulae, each of $R^{101a}$, $R^{101b}$ and $R^{101c}$ independently represents a straight, branched or cyclic alkyl group, alkenyl group, oxoalkyl group or oxoalkenyl group having 1 to 12 carbon atoms; an aryl group having 6 to 20 carbon atoms; or an aralkyl group or aryloxoalkyl group having 7 to 12 carbon atoms, and a part or all of hydrogen atoms of these groups may be substituted with an alkoxy group or the like. In addition, $R^{101b}$ and $R^{101c}$ may form a ring, and if forming a ring, each of $R^{101b}$ and $R^{101c}$ independently represents an alkylene group having 1 to 6 carbon atoms. K− represents a non-nucleophilic counter ion. $R^{101d}$, $R^{101e}$, $R^{101f}$ and $R^{101g}$ are represented by each independently adding a hydrogen atom to $R^{101a}$, $R^{101b}$ and $R^{101c}$. $R^{101d}$ and $R^{101e}$, and $R^{101d}$, $R^{101e}$ and $R^{101f}$ may form a ring, and if forming a ring, $R^{101d}$ and $R^{101e}$, and $R^{101d}$, $R^{101e}$ and $R^{101f}$ represent an alkylene group having 3 to 10 carbon atoms, or a heteroaromatic ring having therein the nitrogen atom(s) in the formula.

$R^{101a}$, $R^{101b}$, $R^{101c}$, $R^{101d}$, $R^{101e}$, $R^{101f}$ and $R^{101g}$ described above may be the same or different from one another. Specifically, examples of the alkyl group include, but are not limited to the following, a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cycloheptyl group, a cyclopropylmethyl group, a 4-methyl cyclohexyl group, a cyclohexylmethyl group, a norbornyl group, and an adamantyl group. Examples of the alkenyl group include, but are not limited to the following, a vinyl group, an allyl group, a propenyl group, a butenyl group, a hexenyl group, and a cyclohexenyl group. Examples of the oxoalkyl group can include, but are not limited to the following, a 2-oxocyclopentyl group, a 2-oxocyclohexyl group, a 2-oxopropyl group, a 2-cyclopentyl-2-oxoethyl group, a 2-cyclohexyl-2-oxoethyl group, and a 2-(4-methylcyclohexyl)-2-oxoethyl group. Examples of the oxoalkenyl group include, but are not limited to the following, a 2-oxo-4-cyclohexenyl group and a 2-oxo-4-propenyl group. Examples of the aryl group include, but are not limited to the following, a phenyl group, a naphthyl group, alkoxyphenyl groups such as a p-methoxyphenyl group, a m-methoxyphenyl group, an o-methoxyphenyl group, an ethoxyphenyl group, a p-tert-butoxyphenyl group, and a m-tert-butoxyphenyl group; alkylphenyl groups such as a 2-methylphenyl group, a 3-methylphenyl group, a 4-methylphenyl group, an ethylphenyl group, a 4-tert-butylphenyl group, a 4-butylphenyl group, and a dimethylphenyl group; alkylnaphthyl groups such as a methylnaphthyl group and an ethylnaphthyl group; alkoxynaphthyl groups such as a methoxynaphthyl group and an ethoxynaphthyl group; dialkylnaphthyl groups such as a dimethylnaphthyl group and a diethylnaphthyl group; and dialkoxynaphthyl groups such as a dimethoxynaphthyl group and a diethoxynaphthyl group. Examples of the aralkyl group include, but are not limited to the following, a benzyl group, a phenylethyl group, and a phenethyl group. Examples of the aryloxoalkyl group include, but are not limited to the following, 2-aryl-2-oxoethyl groups such as a 2-phenyl-2-oxoethyl group, a 2-(1-naphthyl)-2-oxoethyl group, and a 2-(2-naphthyl)-2-oxoethyl group. Examples of the non-nucleophilic counter ion, K−, include, but are not limited to the following, halide ions such as a chloride ion and a bromide ion; fluoroalkyl sulfonates such as triflate, 1,1,1-trifluoroethane sulfonate, and nonafluorobutane sulfonate; aryl sulfonates such as tosylate, benzene sulfonate, 4-fluorobenzene sulfonate, and 1,2,3,4,5-pentafluorobenzene sulfonate; and alkyl sulfonates such as mesylate and butane sulfonate.

In the case where $R^{101d}$, $R^{101e}$, $R^{101f}$ and $R^{101g}$ are each a heteroaromatic ring having the nitrogen atom(s) in the formula, examples of the heteroaromatic ring include imidazole derivatives (for example, imidazole, 4-methylimidazole, and 4-methyl-2-phenylimidazole), pyrazole derivatives, furazan derivatives, pyrroline derivatives (for example, pyrroline and 2-methyl-1-pyrroline), pyrrolidine derivatives (for example, pyrrolidine, N-methylpyrrolidine, pyrrolidinone, and N-methylpyrrolidone), imidazoline derivatives, imidazolidine derivatives, pyridine derivatives (for example, pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (for example, quinoline and 3-quinolinecarbonitrile), isoquinoline derivatives, cinnoline derivatives, quinazoline derivatives, quinoxaline derivatives, phthalazine derivatives, purine derivatives, pteridin derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivative, and uridine derivatives.

The onium salts of the formula (P1a-1) and the formula (P1a-2) have functions as a photo acid generator and a thermal acid generator. The onium salt of the formula (P1a-3) has a function as a thermal acid generator.

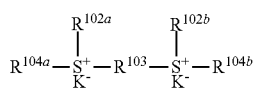

(P1b)

In the formula (P1b), each of $R^{102a}$ and $R^{102b}$ independently represents a straight, branched or cyclic alkyl group having 1 to 8 carbon atoms. $R^{103}$ represents a straight, branched or cyclic alkylene group having 1 to 10 carbon atoms. Each of $R^{104a}$ and $R^{104b}$ independently represents a 2-oxoalkyl group having 3 to 7 carbon atoms. K− represents a non-nucleophilic counter ion.

Specific examples of $R^{102a}$ and $R^{102b}$ include, but are not limited to the following, a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cyclopropylmethyl group, a 4-methyl cyclohexyl group, and a cyclohexylmethyl group. Specific examples of $R^{103}$ include, but are not limited to the following, a methylene group, an ethylene group, a propylene group, a butylene group, a pentylene group, a hexylene group, a heptylene group, an octylene group, a nonylene group, a 1,4-cyclohexylene group, a 1,2-cyclohexylene group, a 1,3-cyclopentylene group, a 1,4-cyclooctylene group, and a 1,4-cyclohexanedimethylene group. Specific examples of $R^{104a}$ and $R^{104b}$ include, but are not limited to the following, a 2-oxopropyl group, a 2-oxocyclopentyl group, a 2-oxocyclohexyl group, and a 2-oxocycloheptyl group. K− includes the same as those described in the formula (P1a-1), (P1a-2) and (P1a-3).

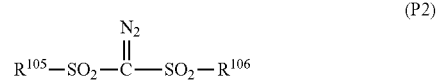

(P2)

In the formula (P2), each of $R^{105}$ and $R^{106}$ independently represents a straight, branched or cyclic alkyl group or halogenated alkyl group having 1 to 12 carbon atoms, an aryl group or halogenated aryl group having 6 to 20 carbon atoms, or an aralkyl group having 7 to 12 carbon atoms.

Examples of the alkyl group in each of $R^{105}$ and $R^{106}$ include, but are not limited to the following, a methyl group, an ethyl group, a propyl group, an isopropyl group, a n-butyl group, a sec-butyl group, a tert-butyl group, a pentyl group, a hexyl group, a heptyl group, an octyl group, an amyl group, a cyclopentyl group, a cyclohexyl group, a cycloheptyl group, a norbornyl group, and an adamantyl group. Examples of the halogenated alkyl group include, but are not limited to the following, a trifluoromethyl group, a 1,1,1-trifluoroethyl group, a 1,1,1-trichloroethyl group, and a nonafluorobutyl group. Examples of the aryl group include, but are not limited to the following, alkoxyphenyl groups such as a phenyl group, a p-methoxyphenyl group, a m-methoxyphenyl group, an o-methoxyphenyl group, an ethoxyphenyl group, a p-tert-butoxyphenyl group, and a m-tert-butoxyphenyl group; and alkylphenyl groups such as a 2-methylphenyl group, a 3-methylphenyl group, a 4-methylphenyl group, an ethylphenyl group, a 4-tert-butylphenyl group, a 4-butylphenyl group, and a dimethylphenyl group. Examples of the halogenated aryl group include, but are not limited to the following, a fluorophenyl group, a chlorophenyl group, and a 1,2,3,4,5-pentafluorophenyl group. Examples of the aralkyl group include, but are not limited to the following, a benzyl group and a phenethyl group.

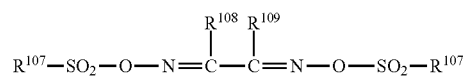

(P3)

In the formula (P3), each of $R^{107}$, $R^{108}$ and $R^{109}$ independently represents a straight, branched or cyclic alkyl group or halogenated alkyl group having 1 to 12 carbon atoms; an aryl group or halogenated aryl group having 6 to 20 carbon atoms; or an aralkyl group having 7 to 12 carbon atoms. $R^{108}$ and $R^{109}$ may be bonded with each other to form a cyclic structure, and if forming a cyclic structure, each of $R^{108}$ and $R^{109}$ represents a straight or branched alkylene group having 1 to 6 carbon atoms.

The alkyl group, halogenated alkyl group, aryl group, halogenated aryl group, and aralkyl group in each of $R^{107}$, $R^{108}$ and $R^{109}$ include the same as those described in $R^{105}$ and $R^{06}$. Herein, examples of the alkylene group in each of $R^{108}$ and $R^{109}$ include, but are not limited to the following, a methylene group, an ethylene group, a propylene group, a butylene group, and a hexylene group.

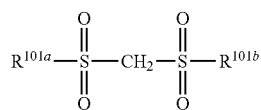

(P4)

In the formula (P4), $R^{101a}$ and $R^{101b}$ are the same as $R^{107}$ in the formula (P3).

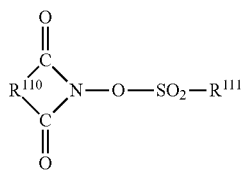
(P5)

In the formula (P5), $R^{110}$ represents an arylene group having 6 to 10 carbon atoms, an alkylene group having 1 to 6 carbon atoms, or an alkenylene group having 2 to 6 carbon atoms, and a part or all of hydrogen atoms of these groups may be further substituted with a straight or branched alkyl group or alkoxy group having 1 to 4 carbon atoms, a nitro group, an acetyl group, or a phenyl group. $R^{111}$ represents a straight, branched or substituted alkyl group, alkenyl group or alkoxyalkyl group having 1 to 8 carbon atoms, a phenyl group, or a naphthyl group, and a part or all of hydrogen atoms of these groups may be further substituted with an alkyl group or alkoxy group having 1 to 4 carbon atoms; a phenyl group that may be substituted with an alkyl group or alkoxy group having 1 to 4 carbon atoms, a nitro group, or an acetyl group; a heteroaromatic group having 3 to 5 carbon atoms; or a chlorine atom or a fluorine atom.

Herein, examples of the arylene group in $R^{110}$ include, but are not limited to the following, a 1,2-phenylene group and a 1,8-naphthylene group. Examples of the alkylene group include, but are not limited to the following, a methylene group, an ethylene group, a trimethylene group, a tetramethylene group, a phenylethylene group, and a norbornane-2,3-diyl group. Examples of the alkenylene group include, but are not limited to the following, a 1,2-vinylene group, a 1-phenyl-1,2-vinylene group, and a 5-norbornene-2,3-diyl group. The alkyl group in R111 includes the same as those in $R^{101a}$ to $R^{101c}$. Examples of the alkenyl group include, but are not limited to the following, a vinyl group, a 1-propenyl group, an allyl group, a 1-butenyl group, a 3-butenyl group, an isoprenyl group, a 1-pentenyl group, a 3-pentenyl group, a 4-pentenyl group, a dimethylallyl group, a 1-hexenyl group, a 3-hexenyl group, a 5-hexenyl group, a 1-heptenyl group, a 3-heptenyl group, a 6-heptenyl group, and a 7-octenyl group. Examples of the alkoxyalkyl group include, but are not limited to the following, a methoxymethyl group, an ethoxymethyl group, a propoxymethyl group, a butoxymethyl group, a pentyloxymethyl group, a hexyloxymethyl group, a heptyloxymethyl group, a methoxyethyl group, an ethoxyethyl group, a propoxyethyl group, a butoxyethyl group, a pentyloxyethyl group, a hexyloxyethyl group, a methoxypropyl group, an ethoxypropyl group, a propoxypropyl group, a butoxypropyl group, a methoxybutyl group, an ethoxybutyl group, a propoxybutyl group, a methoxypentyl group, an ethoxypentyl group, a methoxyhexyl group, and a methoxyheptyl group.

Herein, Examples of the alkyl group having 1 to 4 carbon atoms, which may be further substituted, include, but are not limited to the following, a methyl group, an ethyl group, a propyl group, an isopropyl group, a n-butyl group, a an isobutyl group, and a tert-butyl group. Examples of the alkoxy group having 1 to 4 carbon atoms include, but are not limited to the following, a methoxy group, an ethoxy group, a propoxy group, an isopropoxy group, a n-butoxy group, an isobutoxy group, and tert-butoxy group. Examples of the phenyl group that may be substituted with an alkyl group or alkoxy group having 1 to 4 carbon atoms, a nitro group, or an acetyl group include, but are not limited to the following, a phenyl group, a tolyl group, a p-tert-butoxyphenyl group, a p-acetylphenyl group, and a p-nitrophenyl group. Examples of the heteroaromatic group having 3 to 5 carbon atoms include, but are not limited to the following, a pyridyl group and a furyl group.

Specific examples of the acid generator include, but are not limited to the following, onium salts such as tetramethylammonium trifluoromethanesulfonate, tetramethylammonium nonafluorobutanesulfonate, triethylammonium nonafluorobutanesulfonate, pyridinium nonafluorobutanesulfonate, triethylammonium camphorsulfonate, pyridinium camphorsulfonate, tetra n-butylammonium nonafluorobutanesulfonate, tetraphenylammonium nonafluorobutanesulfonate, tetramethylammonium p-toluenesulfonate, diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, ethylene bis[methyl(2-oxocyclopentyl)sulfonium trifluoromethanesulfonate], and 1,2'-naphthylcarbonylmethyltetrahydrothiophenium triflate; diazomethane derivatives such as bis(benzenesulfonyl)diazomethane, bis(p-toluenesulfonyl)diazomethane, bis(xylenesulfonyl)diazomethane, bis(cyclohexylsulfonyl)diazomethane, bis(cyclopentylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, bis(tert-butylsulfonyl)diazomethane, bis(n-amylsulfonyl)diazomethane, bis(isoamylsulfonyl)diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl)diazomethane, and 1-tert-amylsulfonyl-1-(tert-butylsulfonyl)diazomethane; glyoxime derivatives such as bis-(p-toluenesulfonyl)-α-dimethylglyoxime, bis-(p-toluesulfonyl)-α-diphenylglyoxime, bis-(p-toluenesulfonyl)-α-dicyclohexylglyoxime, bis-(p-toluenesulfonyl)-2,3-pentanedioneglyoxime, bis-(p-toluenesulfonyl)-2-methyl-3,4-pentanedioneglyoxime, bis-(n-butanesulfonyl)-α-dimethylglyoxime, bis-(n-butanesulfonyl)-α-diphenylglyoxime, bis-(n-butanesulfonyl)-α- dicyclohexylglyoxime, bis-(n-butanesulfonyl)-2,3-pentanedioneglyoxime, bis-(n-butanesulfonyl)-2-methyl-3,4-pentanedioneglyoxime, bis-(methanesulfonyl)-α-dimethylglyoxime, bis-(trifluoromethanesulfonyl)-α-dimethylglyoxime, bis-(1,1,1-trifluoroethanesulfonyl)-α-dimethylglyoxime, bis-(tert-butanesulfonyl)-α-dimethylglyoxime, bis-(perfluorooctanesulfonyl)-α-dimethylglyoxime, bis-(cyclohexanesulfonyl)-α-dimethylglyoxime, bis-(benzenesulfonyl)-m-dimethylglyoxime, bis-(p-fluorobenzenesulfonyl)-α-dimethylglyoxime, bis-(p-tert-butylbenzenesulfonyl)-α-dimethylglyoxime, bis-(xylenesulfonyl)-α-dimethylglyoxime, and bis-(camphorsulfonyl)-α-dimethylglyoxime; bissulfone derivatives, such as bisnaphthylsulfonylmethane, bistrifluoromethylsulfonylmethane, bismethylsulfonylmethane, bisethylsulfonylmethane, bispropylsulfonylmethane, bisisopropylsulfonylmethane, bis-p-toluenesulfonylmethane, and bisbenzenesulfonylmethane; β-ketosulfone derivatives such as 2-cyclohexylcarbonyl-2-(p-toluenesulfonyl)propane and 2-isopropylcarbonyl-2-(p-toluenesulfonyl)propane; disulfone derivatives such as a diphenyldisulfone derivative and a dicyclohexyldisulfone derivative, nitrobenzylsulfonate derivatives such as 2,6-dinitrobenzyl p-toluenesulfonate and 2,4-dinitrobenzyl p-toluenesulfonate; sulfonic acid ester derivatives such as 1,2,3-tris(methanesulfonyloxy)benzene, 1,2,3-tris(trifluoromethanesulfonyloxy)benzene, and 1,2,3-tris(p-toluenesulfonyloxy)benzene; and sulfonic acid ester derivatives of a N-hydroxyimide compound, such as N-hydroxysuccinimide methanesulfonic acid ester, N-hydroxysuccinimide trifluoromethanesulfonic acid ester, N-hydroxysuccinimide ethanesulfonic acid ester, N-hydroxysuccinimide 1-propanesulfonic acid ester, N-hydroxysuccinimide 2-propanesulfonic acid ester, N-hydroxysuccinimide 1-pentanesulfonic acid ester, N-hydroxysuccinimide 1-octanesulfonic acid ester, N-hydroxysuccinimide p-toluenesulfonic acid ester, N-hydroxysuccinimide p-methoxybenzenesulfonic acid ester, N-hydroxysuccinimide 2-chloroethanesulfonic acid ester, N-hydroxysuccinimide benzenesulfonic acid ester, N-hydroxysuccinimide-2,4,6-trimethylbenzenesulfonic acid ester, N-hydroxysuccinimide 1-naphthalenesulfonic acid ester, N-hydroxysuccinimide 2-naphthalenesulfonic acid ester, N-hydroxy-2-phenylsuccinimide methanesulfonic acid ester, N-hydroxymaleimide methanesulfonic acid ester, N-hydroxymaleimide ethanesulfonic acid ester, N-hydroxy-2-phenylmaleimide methanesulfonic acid ester, N-hydroxyglutarimide methanesulfonic acid ester, N-hydroxyglutarimide benzenesulfonic acid ester, N-hydroxyphthalimide methanesulfonic acid ester, N-hydroxyphthalimide benzenesulfonic acid ester, N-hydroxyphthalimide trifluoromethanesulfonic acid ester, N-hydroxyphthalimide p-toluenesulfonic acid ester, N-hydroxynaphthalimide methanesulfonic acid ester, N-hydroxynaphthalimide benzenesulfonic acid ester, N-hydroxy-5-norbornene-2,3-dicarboxyimide methanesulfonic acid ester, N-hydroxy-5-norbornene-2,3-dicarboxyimide trifluoromethanesulfonic acid ester, and N-hydroxy-5-norbornene-2,3-dicarboxyimide p-toluenesulfonic acid ester.

Among those described above, onium salts such as triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, and 1,2'-naphthylcarbonylmethyltetrahydrothiophenium triflate; diazomethane derivatives such as bis(benzenesulfonyl)diazomethane, bis(p-toluenesulfonyl)diazomethane, bis(cyclohexylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, and bis(tert-butylsulfonyl)diazomethane; glyoxime derivatives such as bis-(p-toluenesulfonyl)-α-dimethylglyoxime and bis-(n-butanesulfonyl)-α-dimethylglyoxime, bissulfone derivatives such as bisnaphthylsulfonylmethane; and sulfonic acid ester derivatives of an N-hydroxyimide compound, such as N-hydroxysuccinimide methanesulfonic acid ester, N-hydroxysuccinimide trifluoromethanesulfonic acid ester, N-hydroxysuccinimide 1-propanesulfonic acid ester, N-hydroxysuccinimide 2-propanesulfonic acid ester, N-hydroxysuccinimide 1-pentanesulfonic acid ester, N-hydroxysuccinimide p-toluenesulfonic acid ester, N-hydroxynaphthalimide methanesulfonic acid ester, and N-hydroxynaphthalimide benzenesulfonic acid ester, and the like are preferably used.

In the material for forming an underlayer film for lithography according to the present embodiment, the content of the acid generator is not particularly limited, but the content is preferably 0.1 to 50 parts by mass and more preferably 0.5 to 40 parts by mass based on 100 parts by mass of the material for forming an underlayer film. The content is set within the above range to result in a tendency to increase the acid generation amount to promote a crosslinking reaction, and also to result in a tendency to suppress the occurrence of the mixing phenomenon with a resist layer.

[Basic Compound]

Furthermore, the composition for forming an underlayer film for lithography of the present embodiment may further contain a basic compound from the viewpoint of improving preservation stability.

The basic compound serves as a quencher to an acid for preventing a trace amount of the acid generated from the acid generator from promoting a crosslinking reaction. Examples of such a basic compound include primary, secondary, and tertiary aliphatic amines, mixed amines, aromatic amines, heterocyclic amines, a nitrogen-containing compound having a carboxy group, a nitrogen-containing compound having a sulfonyl group, a nitrogen-containing compound having a hydroxyl group, a nitrogen-containing compound having a hydroxyphenyl group, an alcoholic nitrogen-containing compound, an amide derivative, and an imide derivative, but are not particularly limited thereto.

Specific examples of the primary aliphatic amines include, but are not limited to the following, ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Specific examples of the secondary aliphatic amines include, but are not limited to the following, dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Specific examples of the tertiary aliphatic amines include, but are not limited to the following, trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Specific examples of the mixed amines include, but are not limited to the following, dimethylethylamine, methylethylpropylamine, benzylamine, phenethylamine, and benzyldimethylamine. Specific examples of the aromatic amines and heterocyclic amines include, but are not limited to the following, aniline derivatives (for example, aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (for example, pyrrole, 2H-pyrrole, 1-methylpyrrole, 2,4-dimethylpyrrole, 2,5-dimethylpyrrole, and N-methylpyrrole), oxazole derivatives (for example, oxazole and isoxazole), thiazole derivatives (for example, thiazole and isothiazole), imidazole derivatives (for example, imidazole, 4-methylimidazole, and 4-methyl-2-phenylimidazole), pyrazole derivatives, furazan derivatives, pyrroline derivatives (for example, pyrroline and 2-methyl-1-pyrroline), pyrrolidine derivatives (for example, pyrrolidine, N-methylpyrrolidine, pyrrolidinone, and N-methylpyrrolidone), imidazoline derivatives, imidazolidine derivatives, pyridine derivatives (for example, pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (for example, quinoline, 3-quinolinecarbonitrile), isoquinoline derivatives, cinnoline derivatives, quinazoline derivatives, quinoxaline derivatives, phthalazine derivatives, purine derivatives, pteridin derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Furthermore, specific examples of the nitrogen-containing compound having a carboxy group include, but are not limited to the following, aminobenzoic acid, indolecarboxylic acid, and amino acid derivatives (for example, nicotinic acid, alanine, arginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Specific examples of the nitrogen-containing compound having a sulfonyl group include, but are not limited to the following, 3-pyridinesulfonic acid and pyridinium p-toluenesulfonate. Specific examples of the nitrogen-containing compound having a hydroxyl group, the nitrogen-containing compound having a hydroxyphenyl group, and the alcoholic nitrogen-containing compound include, but are not limited to the following, 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Specific examples of the amide derivative include, but are not limited to the following, formamide, N-methylformamide, N,N-dimethylformamide, acetamide, N-methylacetamide, N,N-dimethylacetamide, propionamide, and benzamide. Specific examples of the imide derivative include, but are not limited to the following, phthalimide, succinimide, and maleimide.

In the composition for forming an underlayer film for lithography according to the present embodiment, the content of the basic compound is not particularly limited, but the content is preferably 0.001 to 2 parts by mass and more preferably 0.01 to 1 part by mass based on 100 parts by mass of the material for forming an underlayer film. The content is set within the above preferable range to result in a tendency to improve preservation stability without excessively interrupting a crosslinking reaction.

[Other Additives]

In addition, the composition for forming an underlayer film for lithography of the present embodiment may further contain other resins and/or compounds for the purpose of imparting heat curability and controlling absorbance. Such other resins and/or compounds include naphthol resins, xylene resins, naphthol-modified resins, phenol-modified resins of naphthalene resins, polyhydroxystyrene, dicyclopentadiene resins, (meth)acrylate, dimethacrylate, trimethacrylate, tetramethacrylate, resins having a naphthalene ring such as vinylnaphthalene and polyacenaphthylene, resins having a biphenyl ring such as phenanthrenequinone and fluorene, resins having a heterocyclic ring having a hetero atom such as thiophene and indene, and resins not containing an aromatic ring; rosin-based resins, and resins or compounds including an alicyclic structure, such as cyclodextrin, adamantane(poly)ol, tricyclodecane(poly)ol and derivatives thereof, but are not particularly limited thereto. Furthermore, the material for forming an underlayer film for lithography of the present embodiment can also contain a known additive. Examples of the known additive includes, but not limited to the following, an ultraviolet absorber, a surfactant, a colorant and a non-ionic surfactant.

[Underlayer Film for Lithography and Production Method Thereof]

An underlayer film for lithography of the present embodiment is formed from the composition for forming an underlayer film for lithography of the present embodiment. In addition, a method for producing an underlayer film for lithography of the present embodiment includes a step of forming an underlayer film on a substrate by using the composition for forming an underlayer film for lithography of the present embodiment.

[Multilayer Resist Pattern Forming Method]

In addition, a resist pattern forming method of the present embodiment includes step (A-1) of forming an underlayer film on a substrate by using the composition for forming an underlayer film for lithography of the present embodiment, step (A-2) of forming at least one photoresist layer on the underlayer film, and step (A-3) of irradiating a predetermined region of the photoresist layer with radiation, and developing it.

Furthermore, another pattern forming method (circuit pattern forming method) of the present embodiment includes step (B-1) of forming an underlayer film on a substrate by using the composition for forming an underlayer film for lithography of the present embodiment, step (B-2) of forming an intermediate layer film on the underlayer film by using a silicon atom-containing resist intermediate layer film material, step (B-3) of forming at least one photoresist layer on the intermediate layer film, step (B-4) of irradiating a predetermined region of the photoresist layer with radiation, and developing it to form a resist pattern, step (B-5) of etching the intermediate layer film with the resist pattern as a mask, to form an intermediate layer film pattern, step (B-6) of etching the underlayer film with the intermediate layer film pattern as an etching mask, to form an underlayer film pattern, and step (B-7) of etching the substrate with the underlayer film pattern as an etching mask, to form a pattern on the substrate.

The underlayer film for lithography of the present embodiment is not particularly limited in terms of the forming method thereof as long as it is formed from the composition for forming an underlayer film for lithography of the present embodiment, and a known method can be applied. For example, the underlayer film can be formed by applying the composition for forming an underlayer film for lithography of the present embodiment on the substrate by a known coating method or printing method such as spin coating or screen printing, and removing an organic solvent by volatilization or the like.

The underlayer film is preferably baked upon forming in order to suppress the occurrence of the mixing phenomenon with an upperlayer resist and also promote a crosslinking reaction. In this case, the baking temperature is not particularly limited, but it is preferably within the range of 80 to 450° C., and more preferably 200 to 400° C. In addition, the baking time is not also particularly limited, but is preferably within the range of 10 to 300 seconds. Herein, the thickness of the underlayer film can be appropriately selected depending on the required properties, and is not particularly limited, but is preferably about 30 to 20000 nm, more preferably 50 to 15000 nm.

After the underlayer film is prepared, in the case of a two-layer process, a silicon-containing resist layer or a usual single-layer resist including a hydrocarbon is preferably prepared on the underlayer film, and in the case of a three-layer process, a silicon-containing intermediate layer is preferably prepared on the underlayer film, and a single-layer resist layer not containing silicon is preferably prepared on the silicon-containing intermediate layer. In these cases, a photoresist material for forming the resist layer, which can be used, is a known one.

After the underlayer film is prepared on the substrate, in the case of a two-layer process, a silicon-containing resist layer or a usual single-layer resist including a hydrocarbon can be prepared on the underlayer film. In the case of a three-layer process, a silicon-containing intermediate layer can be prepared on the underlayer film, and a single-layer resist layer not containing silicon can be prepared on the silicon-containing intermediate layer. In these cases, a photoresist material for forming the resist layer, which can be used, is appropriately selected from known ones, and is not particularly limited.

As the silicon-containing resist material for a two-layer process, a positive-type photoresist material is preferably used, which contains a silicon atom-containing polymer such as a polysilsesquioxane derivative or a vinylsilane derivative used as a base polymer in the viewpoint of oxygen gas-etching resistance, and an organic solvent, an acid generator and if necessary a basic compound. Herein, as the silicon atom-containing polymer, a known polymer used in such a resist material can be used.

As the silicon-containing intermediate layer for a three-layer process, a polysilsesquioxane-based intermediate layer is preferably used. The intermediate layer is allowed to have an effect as an antireflective film, and thus tends to make it possible to effectively suppress reflection. For example, if a material including many aromatic groups and having a high substrate-etching resistance is used for the underlayer film in a 193 nm exposure process, a k-value tends to be increased to increase substrate reflection, but the reflection can be suppressed by the intermediate layer to thereby make the substrate reflection 0.5% or less. For the intermediate layer having such an antireflection effect, but not limited to the following, polysilsesquioxane into which a phenyl group or a light-absorbing group having a silicon-silicon bond for 193 nm exposure is introduced and which is to be crosslinked with an acid or heat is preferably used.

An intermediate layer formed by the Chemical Vapour Deposition (CVD) method can also be used. As the intermediate layer having a high effect as an antireflective film, prepared by the CVD method, but not limited to the following, for example, a SiON film is known. In general, the intermediate layer is formed by a wet process such as a spin coating method or screen printing rather than the CVD method in terms of simplicity and cost effectiveness. Herein, the upperlayer resist in a three-layer process may be of positive-type or negative-type, and the same one as a commonly used single-layer resist can be used therefor.

Furthermore, the underlayer film of the present embodiment can also be used as a usual antireflective film for use in a single-layer resist or a usual underlying material for suppressing pattern collapse. The underlayer film of the present embodiment can also be expected to serve as a hard mask for underlying processing because of being excellent in etching resistance for underlying processing.

In the case where a resist layer is formed by the photoresist material, a wet process such as a spin coating method or screen printing is preferably used as in the case of forming the underlayer film. The resist material is coated by a spin coating method or the like and then usually pre-baked, and such pre-baking is preferably performed in the range of 80 to 180° C. for 10 to 300 seconds. Thereafter, in accordance with an ordinary method, the resultant can be subjected to exposure, post-exposure bake (PEB), and development to obtain a resist pattern. Herein, the thickness of the resist film is not particularly limited, but generally, it is preferably 30 to 500 nm and more preferably 50 to 400 nm.

Light for use in exposure may be appropriately selected depending on the photoresist material to be used. Examples of the light for use in exposure include, for example, high energy radiation having a wavelength of 300 nm or less, specifically, excimer lasers of 248 nm, 193 nm, and 157 nm, a soft X-ray of 3 to 20 nm, electron beam, and an X-ray.

The resist pattern formed by the above method is a pattern whose collapse is suppressed by the underlayer film of the present embodiment. Therefore, the underlayer film of the present embodiment can be used to thereby obtain a finer pattern, and an exposure amount necessary for obtaining such a resist pattern can be reduced.

Then, the obtained resist pattern is used as a mask to perform etching. As the etching of the underlayer film in a two-layer process, gas etching is preferably used. As the gas etching, etching using oxygen gas is suitable. In addition to oxygen gas, an inert gas such as He and Ar, and CO, $CO_2$, $NH_3$, $SO_2$, $N_2$, $NO_2$, and $H_2$ gases can also be added. The gas etching can also be performed not using oxygen gas but using only CO, $CO_2$, $NH_3$, $N_2$, $NO_2$, and $H_2$ gases. In particular, the latter gases are preferably used for protecting a side wall for preventing a pattern side wall from being undercut.

On the other hand, also in the etching of the intermediate layer in a three-layer process, gas etching is preferably used. As the gas etching, the same one as the one described in a two-layer process can be applied. In particular, the intermediate layer is preferably processed in a three-layer process using a fluorocarbon gas with the resist pattern as a mask. Thereafter, as described above, the intermediate layer pattern is used as a mask to perform, for example, oxygen gas etching, thereby processing the underlayer film.

Herein, in the case where an inorganic hard mask intermediate layer film is formed as the intermediate layer, a silicon oxide film, a silicon nitride film, and a silicon oxynitride film (SiON film) are formed by the CVD method, the ALD method, and the like. The nitride film forming method that can be used is, but not limited to the following, any method described in, for example, Japanese Patent Laid-Open No. 2002-334869 (Patent Literature 6) and WO2004/066377 (Patent Literature 7). While the photoresist film can be directly formed on such an intermediate layer film, an organic antireflective film (BARC) may also be formed on the intermediate layer film by spin coating, and the photoresist film may also be formed thereon.

As the intermediate layer, a polysilsesquioxane-based intermediate layer is also preferably used. The resist intermediate layer film is allowed to have an effect as an antireflective film, and thus tends to make it possible to effectively suppress reflection. A specific material for the polysilsesquioxane-based intermediate layer that can be used is, but not limited to the following, any material described in, for example, Japanese Patent Laid-Open No. 2007-226170 (Patent Literature 8) and Japanese Patent Laid-Open No. 2007-226204 (Patent Literature 9).

The next etching of the substrate can also be performed by an ordinary method, and, for example, when the substrate is made of SiO2 or SiN, etching with mainly a fluorocarbon gas can be performed, and when the substrate is made of p-Si, Al, or W, etching mainly using a chlorine-based gas or bromine-based gas can be performed. In the case where the substrate is processed by the etching with a fluorocarbon gas, the silicon-containing resist in a two-layer resist process and the silicon-containing intermediate layer in a three-layer process are peeled off at the same time as the processing of the substrate. On the other hand, in the case where the substrate is processed by the etching with a chlorine-based gas or bromine-based gas, the silicon-containing resist layer or the silicon-containing intermediate layer is peeled off separately, and is generally peeled off by dry etching with a fluorocarbon gas after the substrate is processed.

The underlayer film of the present embodiment is characterized by being excellent in etching resistance of such a substrate. Herein, the substrate that can be used is appropriately selected from known ones, and is not particularly limited, but includes Si, α-Si, p-Si, $SiO_2$, SiN, SiON, W, TiN, and Al substrates. In addition, the substrate may also be a laminate having a processed film (processed substrate) on a base material (support). Such a processed film includes various Low-k films of Si, $SiO_2$, SiON, SiN, p-Si, α-Si, W, W—Si, Al, Cu, and Al—Si, and stopper films thereof, and a material different from the base material (support) is preferably used therefor. Herein, the thickness of the substrate to be processed or the processed film is not particularly limited, but it is usually preferably about 50 to 10000 nm, more preferably 75 to 5000 nm.

[Purification Method of Compound or Resin]

A purification method of the compound or the resin of the present embodiment includes a step of providing a solution (A) by dissolving at least any of a compound represented by the following formula (1) or a resin including a structural unit derived from a compound represented by the following formula (1) in a solvent, and a first extraction step of bringing the resulting solution (A) into contact with an acidic aqueous solution, to extract impurities in the solution (A), wherein the solvent to be used in the step of providing the solution (A) includes an organic solvent optionally immiscible with water.

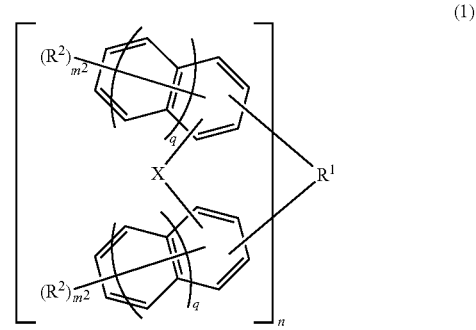

(1)

(in formula (1), $R^1$ represents a 2n-valent group having 1 to 60 carbon atoms, or a single bond, each $R^2$ independently represents a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, a thiol group, a hydroxyl group, or a group where a hydrogen atom of a hydroxyl group is substituted with an acid-dissociable group, and may be the same or different in the same naphthalene ring or benzene ring, in which at least one $R^2$ represents a group where a hydrogen atom of a hydroxyl group is substituted with an acid-dissociable group, n is an integer of 1 to 4, and structural formulae of n structural units in square brackets [ ] may be the same or different when n is an integer of 2 or more, X represents an oxygen atom, a sulfur atom, or a non-bridging group, each $m^2$ is independently an integer of 0 to 7, provided that at least one $m^2$ is an integer of 1 to 7, and each q is independently 0 or 1.)

In the first extraction step, the resin is preferably a resin obtained by reacting the compound represented by the formula (1) with the compound having crosslinking reactivity. The purification method of the present embodiment can allow for reductions in the contents of various metals which can be contained as impurities in the compound or the resin having the specified structure. More specifically, in the purification method of the present embodiment, the compound and/or the resin can be dissolved in an organic solvent optionally immiscible with water to provide a solution (A), and bringing the solution (A) into contact with an acidic aqueous solution for performing an extraction treatment. Thus, a metal content included in the solution (A) including at least any of the compound represented by the formula (1) or a resin including a structural unit derived from a compound represented by the formula (1) can be transferred to an aqueous phase, and thereafter an organic phase and the aqueous phase can be separated to provide the compound represented by the formula (1) and/or the resin including the structural unit derived from the compound, where the metal content is reduced.

The compound represented by the formula (1) and the resin including the structural unit derived from the compound, to be used in the purification method of the present embodiment, may be used singly or as a mixture of two or more thereof. In addition, the compound represented by the formula (1) and the resin including the compound as a constituent component may also contain various surfactants, various crosslinking agents, various acid generators, various stabilizers, and the like.

The organic solvent optionally immiscible with water, to be used in the present embodiment, is not particularly limited, but it is preferably an organic solvent that can be safely applied to a semiconductor manufacturing process, and is specifically an organic solvent whose solubility in water at room temperature is less than 30%, more preferably less than 20%, further preferably less than 10%. The amount of the organic solvent to be used is preferably about 1 to 100 times the amount of the compound represented by the formula (1) and/or the resin including the compound as a constituent component, to be used.

Specific examples of the organic solvent optionally immiscible with water include, but not limited to the following, ethers such as diethyl ether and diisopropyl ether, esters such as ethyl acetate, n-butyl acetate and isoamyl acetate, ketones such as methyl ethyl ketone, methyl isobutyl ketone, ethyl isobutyl ketone, cyclohexanone, cyclopentanone, 2-heptanone and 2-pentanone; glycol ether acetates such as ethylene glycol monoethyl ether acetate, ethylene glycol monobutyl ether acetate, propylene glycol monomethyl ether acetate (PGMEA) and propylene glycol monoethyl ether acetate; aliphatic hydrocarbons such as n-hexane and n-heptane; aromatic hydrocarbons such as toluene and xylene; and halogenated hydrocarbons such as methylene chloride and chloroform. Among them, toluene, 2-heptanone, cyclohexanone, cyclopentanone, methyl isobutyl ketone, propylene glycol monomethyl ether acetate, ethyl acetate, and the like are preferable, methyl isobutyl ketone, ethyl acetate, cyclohexanone and propylene glycol monomethyl ether acetate are more preferable, and methyl isobutyl ketone and ethyl acetate are more further preferable. When methyl isobutyl ketone, ethyl acetate, or the like is adopted, the compound represented by the formula (1) and the resin including the compound as a constituent component can have a relatively high saturation solubility and a relatively low boiling point, thereby allowing loads in a case of industrial distillation off of the solvent and in a step of removal thereof by drying to be reduced. These solvents can be used singly or as a mixture of two or more thereof.

The acidic aqueous solution to be used in the purification method of the present embodiment is appropriately selected from aqueous solutions in which an organic compound or an inorganic compound commonly known is dissolved in water. Examples thereof include, but not limited to the following, an aqueous mineral acid solution in which a mineral acid such as hydrochloric acid, sulfuric acid, nitric acid or phosphoric acid is dissolved in water, or an aqueous organic acid solution in which an organic acid such as acetic acid, propionic acid, oxalic acid, malonic acid, succinic acid, fumaric acid, maleic acid, tartaric acid, citric acid, methanesulfonic acid, phenolsulfonic acid, p-toluenesulfonic acid or trifluoroacetic acid is dissolved in water. These acidic aqueous solutions can be used singly or in combinations of two or more thereof. Among these acidic aqueous solutions, an aqueous solution of at least one mineral acid selected from the group consisting of hydrochloric acid, sulfuric acid, nitric acid and phosphoric acid, or an aqueous solution of at least one organic acid selected from the group consisting of acetic acid, propionic acid, oxalic acid, malonic acid, succinic acid, fumaric acid, maleic acid, tartaric acid, citric acid, methanesulfonic acid, phenolsulfonic acid, p-toluenesulfonic acid and trifluoroacetic acid is preferable, an aqueous solution of sulfuric acid, nitric acid, or a carboxylic acid such as acetic acid, oxalic acid, tartaric acid or citric acid is more preferable, an aqueous solution of sulfuric acid, oxalic acid, tartaric acid or citric acid is further preferable, and an aqueous solution of oxalic acid is more further preferable. It is considered that a polyvalent carboxylic acid such as oxalic acid, tartaric acid and citric acid is coordinated with a metal ion to exert a chelating effect, and therefore tends to allow a metal to be more effectively removed. In addition, the water to be here used is preferably water having a low metal content according to the purpose of the purification method of the present embodiment, such as ion-exchange water.

The pH of the acidic aqueous solution to be used in the purification method of the present embodiment is not particularly limited, but the acidity of the aqueous solution is preferably adjusted in consideration of the effect on the compound represented by the formula (1) and the resin including the compound as a constituent component. The pH is preferably in the range from about 0 to 5, more preferably about 0 to 3.

The amount of the acidic aqueous solution to be used in the purification method of the present embodiment is not particularly limited, but the amount to be used is preferably adjusted from the viewpoint of reducing the number of extractions for metal removal and the viewpoint of ensuring operation property in consideration of the total amount of the liquid. The amount of the acidic aqueous solution to be used is preferably 10 to 200% by mass, more preferably 20 to 100% by mass based on 100% by mass of the solution (A), from the above viewpoints.

In the purification method of the present embodiment, the acidic aqueous solution can be brought into contact with the solution (A) including at least one selected from the compound represented by the formula (1) and the resin including the structural unit derived from the compound, and the organic solvent optionally immiscible with water, to thereby extract the metal content from the compound or the resin in the solution (A).

In the purification method of the present embodiment, the solution (A) preferably further includes an organic solvent optionally miscible with water. When the organic solvent optionally miscible with water is included, the amounts of the compound represented by the formula (1) and the resin including the structural unit derived from the compound to be charged can be increased, and an enhancement in liquid separability can be achieved to result in a tendency to perform purification at a high pot efficiency. The method of adding the organic solvent optionally miscible with water is not particularly limited. For example, there can be adopted any of a method of adding the organic solvent optionally miscible with water to the solution including an organic solvent in advance, a method of adding the organic solvent optionally miscible with water, to water or the acidic aqueous solution in advance, and a method of bringing the solution including an organic solvent into contact with water or the acidic aqueous solution and thereafter adding the organic solvent optionally miscible with water. Among them, a method of adding the organic solvent optionally miscible with water to the solution including an organic solvent in advance is preferable in terms of operational workability and ease of management of the amounts to be charged.

The organic solvent optionally miscible with water, to be used in the purification method of the present embodiment, is not particularly limited, but it is preferably an organic solvent that can be safely applied to a semiconductor manufacturing process. The amount of the organic solvent optionally miscible with water, to be used, is not particularly limited as long as a solution phase and the aqueous phase are separated, but it is preferably 0.1 to 100 times, more preferably 0.1 to 50 times, further preferably 0.1 to 20 times relative to the compound represented by the formula (1) and the resin including the structural unit derived from the compound.

Specific examples of the organic solvent optionally miscible with water, to be used in the purification method of the present embodiment, include, but not limited to the following, ethers such as tetrahydrofuran and 1,3-dioxolane; alcohols such as methanol, ethanol and isopropanol; ketones such as acetone and N-methylpyrrolidone; and aliphatic hydrocarbons, for example, glycol ethers such as ethylene glycol monoethyl ether, ethylene glycol monobutyl ether, propylene glycol monomethyl ether (PGME) and propylene glycol monoethyl ether. Among them, N-methylpyrrolidone, propylene glycol monomethyl ether, and the like are preferable, and N-methylpyrrolidone and propylene glycol monomethyl ether are more preferable. These solvents can be used singly or as a mixture of two or more thereof.

The temperature in performing of the extraction treatment is preferably in the range from 20 to 90° C., more preferably 30 to 80° C. The extraction operation is performed by, for example, well mixing with stirring or the like and thereafter standing. Thus, the metal content included in the solution including the compound represented by the formula (1) or the resin including the structural unit derived from the compound and the organic solvent is transferred to the aqueous phase. In addition, the operation can allow the acidity of the solution to be reduced, thereby suppressing the change of the compound represented by the formula (1) or the resin including the structural unit derived from the compound.

The resulting mixed solution is left to stand and thus separated to the solution phase including at least one selected from the group consisting of the compound represented by the formula (1) and the resin including the compound as a constituent component and the organic solvent, and the aqueous phase, and therefore the solution phase including at least one selected from the group consisting of the compound represented by the formula (1) and the resin including the compound as a constituent component and the organic solvent is recovered by decantation or the like. The standing time is not particularly limited, but the standing time is preferably adjusted from the viewpoint of providing better separation to the solution phase including the organic solvent, and the aqueous phase. The standing time is usually 1 minute or more, preferably 10 minutes or more, more preferably 30 minutes or more. In addition, the extraction treatment may be performed only once, but is also effectively performed with operations such as mixing, standing and separation being repeatedly performed multiple times.

The purification method of the present embodiment preferably further includes, after the first extraction step, a second extraction step (second extraction step) of further bringing the solution phase including the compound and/or the resin into contact with water, to further extract impurities in the solution (A). Specifically, for example, the extraction treatment is performed by using the acidic aqueous solution, thereafter the solution phase including at least one selected from the compound represented by the formula (1) and the resin including the structural unit derived from the compound, extracted and recovered from the aqueous solution, and the organic solvent is preferably further subjected to an extraction treatment with water. The extraction treatment with water is not particularly limited, and, can be performed by, for example, well mixing of the solution phase and water with stirring or the like and thereafter standing of the resulting mixed solution. The mixed solution after standing is separated to the solution phase including at least one selected from the compound represented by the formula (1) and the resin including the structural unit derived from the compound, and the organic solvent, and the aqueous phase, and therefore the solution phase including at least one selected from the compound represented by the formula (1) and the resin including the structural unit derived from the compound, and the organic solvent can be recovered by decantation or the like. In addition, the water to be here used is preferably water having a low metal content according to the purpose of the present embodiment, such as ion-exchange water. The extraction treatment may be performed only once, but is also effectively performed with operations such as mixing, standing and separation being repeatedly performed multiple times. In addition, conditions in the extraction treatment, such as the ratio of both to be used, the temperature and the time, are not particularly limited, but may be the same as in the case of the contact treatment with the acidic aqueous solution above.

The water content that can be incorporated in the solution thus obtained, including at least one selected from the compound represented by the formula (1) and the resin including the structural unit derived from the compound, and the organic solvent, can be easily removed by performing an operation such as distillation under reduced pressure. In addition, an organic solvent can be if necessary added to adjust the concentration of the compound represented by the formula (1) or the resin including the structural unit derived from the compound to any concentration.

The method of isolating at least one selected from the compound represented by the formula (1) and the resin including the structural unit derived from the compound from the resulting solution including at least one selected from the compound represented by the formula (1) and the resin including the structural unit derived from the compound and the solvent is not particularly limited, and can be performed according to a known method such as removal under reduced pressure, separation by reprecipitation and a combination thereof. If necessary, a known treatment such as a concentration operation, a filtration operation, a centrifugation operation and a drying operation can be performed.

EXAMPLES

Hereinafter, the present embodiment will be described by Synthesis Experimental Examples, Synthesis Comparative Examples, Examples and Comparative Examples in more detail, but the present embodiment is not limited thereto at all.

(Structure of Compound)

The structure of each compound was confirmed by performing 1H-NMR measurement with an "Advance 60011 spectrometer" manufactured by Bruker Corporation under the following conditions.

Frequency: 400 MHz
Solvent: d6-DMSO
Internal standard: TMS
Measurement temperature: 23° C.

(Carbon Concentration and Oxygen Concentration)

The carbon concentration and the oxygen concentration (% by mass) were measured by organic element analysis with the following apparatus.

Apparatus: CHN CORDER MT-6 (manufactured by Yanaco Bunseki Kogyo Co.)

(Molecular Weight)

The molecular weight of each compound was measured by FD-MS analysis with JMS-T100GCV manufactured by JEOL Ltd.

(Molecular Weight in Terms of Polystyrene)

With respect to the molecular weight of each resin, gel permeation chromatography (GPC) analysis was used to determine the weight average molecular weight (Mw) and the number average molecular weight (Mn) in terms of polystyrene, and to determine the degree of dispersion (Mw/Mn).

Apparatus: Shodex GPC-101 type (manufactured by Showa Denko K. K.)
Column: KF-80M×3
Eluent: THF 1 mL/min
Temperature: 40° C.

(Pyrolysis Temperature (Tg))

An "EXSTAR 6000 DSC apparatus" manufactured by SII NanoTechnology Inc. was used, and about 5 mg of a sample was placed in an unsealed aluminum container and heated to 500° C. at a rate of temperature rise of 10° C./min in a nitrogen gas (30 mL/min) stream. In this time, a temperature at which a reducing portion appeared on the base line was defined as a pyrolysis temperature (Tg).

The heat resistance was evaluated according to the following criteria.

Evaluation A: the pyrolysis temperature was 150° C. or higher
Evaluation C: the pyrolysis temperature was lower than 150° C.

(Solubility)

The amount of each compound dissolved in 1-methoxy-2-propanol (PGME) and propylene glycol monomethyl ether acetate (PGMEA) was measured at 23° C., and the results were evaluated with respect to the solubility according to the following criteria.

Evaluation A: 20% by mass or more
Evaluation B: 10% by mass or more and less than 20% by mass
Evaluation C: less than 10% by mass (Synthesis Example 1) Synthesis of A-1 (Xanthene Compound)

In a container having an inner volume of 300 mL, equipped with a stirrer, a condenser and a burette, 7.0 g (40 mmol) of 2,6-naphthalenediol (reagent produced by Sigma-Aldrich Co. LLC.) and 4.6 g (20 mmol) of 3-iodobenzaldehyde (reagent produced by Tokyo Chemical Industry Co., Ltd.) were charged to 100 mL of γ-butyrolactone, 0.5 g of p-toluenesulfonic acid was added thereto, and the content was stirred at 90° C. for 23 hours to perform a reaction, thereby providing a reaction liquid. Next, the reaction liquid was added to 1000 g of pure water and thereafter extracted by ethyl acetate and concentrated to provide a solution.

The resulting solution was subjected to separation by column chromatography, and thereafter washed with chloroform to thereby provide 4.2 g of an objective compound (A-1) represented by the following formula (A-1).

The molecular weight of the resulting compound (A-1) was measured by the above method, and as a result, it was 516.

The resulting compound (A-1) was subjected to the NMR measurement under the above measurement conditions, and thus the following peaks were observed and it was confirmed that the compound had a chemical structure of the following formula (A-1).

δ (ppm) 9.7 (2H, O—H), 7.0-8.5 (14H, Ph-H), 6.5 (1H, C—H)

Herein, the resulting compound (A-1) having a substituent of 2,6-naphthalenediol at the 1-position was confirmed from signals of protons at the 3-position and the 4-position being doublets.

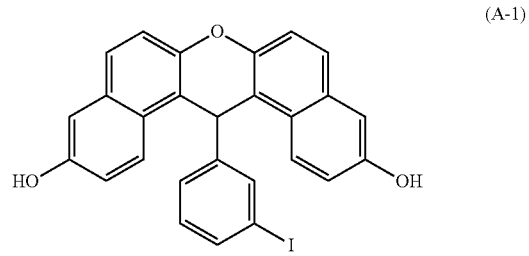 [SMILES: Oc1ccc2c3c(ccc2c1)Oc1ccc2cc(O)ccc2c1C3c1cccc(I)c1]

(A-1)

(Synthesis Example 2) Synthesis of A-2 (Xanthene Compound)

In a container having an inner volume of 300 mL, equipped with a stirrer, a condenser and a burette, 7.0 g (40 mmol) of 2,6-naphthalenediol (reagent produced by Sigma-Aldrich Co. LLC.) and 5.6 g (20 mmol) of 5-iodovanillin (reagent produced by Tokyo Chemical Industry Co., Ltd.) were charged to 100 mL of γ-butyrolactone, and 0.5 g of p-toluenesulfonic acid was added thereto and stirred at 90° C. for 87 hours to perform a reaction, thereby providing a reaction liquid. Next, the reaction liquid was added to 1000 g of pure water and thereafter extracted by ethyl acetate and concentrated to provide a solution.

The resulting solution was subjected to separation by column chromatography, and thereafter washed with chloroform to thereby provide 2.0 g of an objective compound (A-2) represented by the following formula (A-2).

The molecular weight of the resulting compound (A-2) was measured by the above method, and as a result, it was 562.

The resulting compound (A-2) was subjected to the NMR measurement under the above measurement conditions, and thus the following peaks were observed and it was confirmed that the compound had a chemical structure of the following formula (A-2).

δ (ppm) 9.7, 9.3 (3H, O—H), 7.2-8.5 (12H, Ph-H), 6.4 (1H, C—H), 3.7 (3H, O—C—H)

Herein, the resulting compound (A-2) having a substituent of 2,6-naphthalenediol at the 1-position was confirmed from signals of protons at the 3-position and the 4-position being doublets.

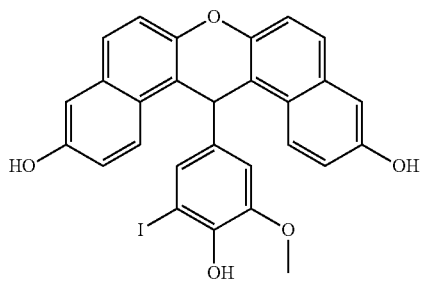

(A-2)

(Synthesis Example 3) Synthesis of A-3 (Xanthene Compound)

In a container having an inner volume of 300 mL, equipped with a stirrer, a condenser and a burette, 14.0 g (80 mmol) of 2,6-naphthalenediol (reagent produced by Sigma-Aldrich Co. LLC.) and 9.0 g (40 mmol) of 5-iodo-2-furancarbaldehyde (reagent produced by Tokyo Chemical Industry Co., Ltd.) were charged to 100 mL of γ-butyrolactone, and 0.5 g of p-toluenesulfonic acid was added thereto and stirred at 90° C. for 24 hours to perform a reaction, thereby providing a reaction liquid. Next, the reaction liquid was added to 300 g of pure water and thereafter extracted by ethyl acetate and concentrated to provide a solution.

The resulting solution was subjected to separation by column chromatography, and thereafter washed with chloroform to thereby provide 4.5 g of an objective compound represented by the following formula (A-3).

The molecular weight of the resulting compound (A-3) was measured by the above method, and as a result, it was 506.

The resulting compound (A-3) was subjected to the NMR measurement under the above measurement conditions, and thus the following peaks were observed and it was confirmed that the compound had a chemical structure of the following formula (A-3).

δ (ppm) 9.5 (2H, O—H), 7.1-8.3 (12H, Ph-H), 6.2 (1H, C—H)

Herein, the resulting compound (A-3) having a substituent of 2,6-naphthalenediol at the 1-position was confirmed from signals of protons at the 3-position and the 4-position being doublets.

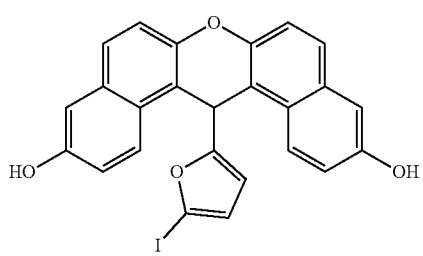

(A-3)

(Synthesis Example 4) Synthesis of B-1 (Xanthene Compound)

In a container having an inner volume of 100 mL, equipped with a stirrer, a condenser and a burette, 3.5 g (20 mmol) of 2,7-naphthalenediol (reagent produced by Sigma-Aldrich Co. LLC.) and 2.3 g (20 mmol) of 3-iodobenzaldehyde (reagent produced by Tokyo Chemical Industry Co., Ltd.) were charged to 50 mL of γ-butyrolactone, and 0.3 g of p-toluenesulfonic acid was added thereto and stirred at 90° C. for 8 hours to perform a reaction, thereby providing a reaction liquid. Next, the reaction liquid was added to 500 g of pure water and thereafter extracted by ethyl acetate and concentrated to provide a solution.

The resulting solution was subjected to separation by column chromatography, and thereafter washed with chloroform to thereby provide 1.8 g of an objective compound represented by the following formula (B-1).

The molecular weight of the resulting compound (B-1) was measured by the above method, and as a result, it was 516.

The resulting compound (B-1) was subjected to the NMR measurement under the above measurement conditions, and thus the following peaks were observed and it was confirmed that the compound had a chemical structure of the following formula (B-1).

δ (ppm) 9.9 (2H, O—H), 7.0-8.3 (14H, Ph-H), 6.1 (1H, C—H)

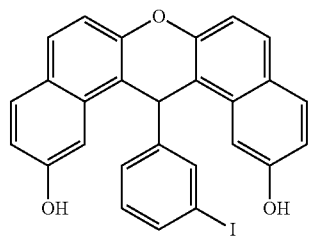

(B-1)

(Synthesis Example 5) Synthesis of B-3 (Xanthene Compound)

In a container having an inner volume of 300 mL, equipped with a stirrer, a condenser and a burette, 7.0 g (40 mmol) of 2,7-naphthalenediol (reagent produced by Sigma-Aldrich Co. LLC.) and 5.6 g (20 mmol) of 5-iodovanillin (reagent produced by Tokyo Chemical Industry Co., Ltd.) were charged to 100 mL of γ-butyrolactone, and 0.5 g of p-toluenesulfonic acid was added thereto and stirred at 90° C. for 10 hours to perform a reaction, thereby providing a reaction liquid. Next, the reaction liquid was added to 1000 g of pure water and thereafter extracted by ethyl acetate and concentrated to provide a solution.

The resulting solution was subjected to separation by column chromatography, and thereafter washed with chloroform to thereby provide 2.0 g of an objective compound represented by the following formula (B-3). The molecular weight of the resulting compound (B-3) was measured by the above method, and as a result, it was 562.

The resulting compound (B-3) was subjected to the NMR measurement under the above measurement conditions, and thus the following peaks were observed and it was confirmed that the compound had a chemical structure of the following formula (B-3).

δ (ppm) 9.9, 9.4 (3H, O—H), 7.0-8.3 (12H, Ph-H), 6.0 (1H, C—H), 3.8 (3H, O—C—H)

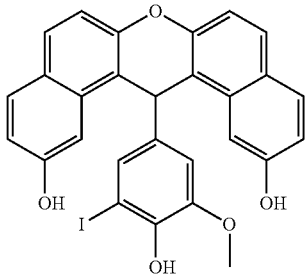

(B-3)

(Synthesis Example 6) Synthesis of B-4 (Xanthene Compound)

In a container having an inner volume of 300 mL, equipped with a stirrer, a condenser and a burette, 7.0 g (40 mmol) of 2,7-naphthalenediol (reagent produced by Sigma-Aldrich Co. LLC.) and 4.5 g (20 mmol) of 5-iodo-2-furancarbaldehyde (reagent produced by Tokyo Chemical Industry Co., Ltd.) were charged to 100 mL of γ-butyrolactone, and 0.5 g of p-toluenesulfonic acid was added thereto and stirred at 90° C. for 12 hours to perform a reaction, thereby providing a reaction liquid. Next, the reaction liquid was added to 300 g of pure water and thereafter extracted by ethyl acetate and concentrated to provide a solution.

The resulting solution was subjected to separation by column chromatography, and thereafter washed with chloroform to thereby provide 3.7 g of an objective compound represented by the following formula (B-4).

The molecular weight of the resulting compound (B-4) was measured by the above method, and as a result, it was 506.

The resulting compound (B-4) was subjected to the NMR measurement under the above measurement conditions, and thus the following peaks were observed and it was confirmed that the compound had a chemical structure of the following formula (B-4).

δ (ppm) 9.4 (2H, O—H), 7.1-8.2 (12H, Ph-H), 6.2 (1H, C—H)

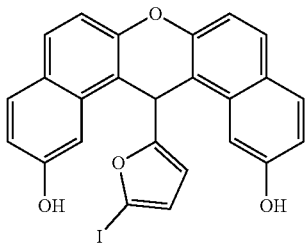

(B-4)

(Synthesis Experimental Example 1) Synthesis of A-1-BOC

In a container having an inner volume of 200 mL, equipped with a stirrer, a condenser and a burette, 6.5 g (12.5 mmol) of the compound (A-1) and 5.5 g (25 mmol) of di-t-butyl dicarbonate (produced by Sigma-Aldrich Co. LLC.) were charged to 100 mL of acetone, 3.45 g (25 mmol) of potassium carbonate (produced by Sigma-Aldrich Co. LLC.) was added thereto, and the content was stirred at 20° C. for 6 hours to perform a reaction, thereby providing a reaction liquid. Next, the reaction liquid was concentrated, 100 g of pure water was added to a concentrated liquid to precipitate a reaction product, and the resultant was cooled to room temperature and thereafter filtered to separate a solid.

The resulting solid was subjected to filtration, dried, and thereafter separated and purified by column chromatography to thereby provide 2.0 g of an objective compound (A-1-BOC) represented by the following formula (A-1-BOC).

The molecular weight of the resulting compound (A-1-BOC) was measured by the above method, and as a result, it was 716.

The resulting compound (A-1-BOC) was subjected to the NMR measurement under the above measurement conditions, and thus the following peaks were observed and it was confirmed that the compound had a chemical structure of the following formula (A-1-BOC).

δ (ppm) 7.2-8.7 (14H, Ph-H), 6.8 (1H, C—H), 1.6 (18H, C—CH$_3$)

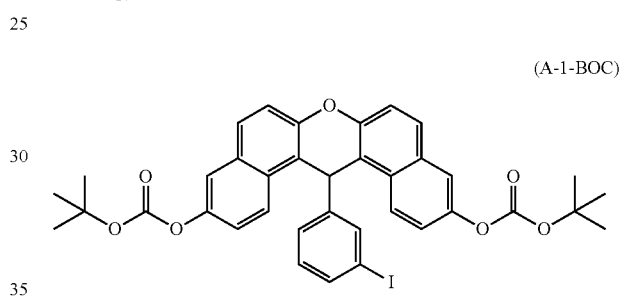

(A-1-BOC)

As a result of organic element analysis, the carbon concentration and the oxygen concentration of the resulting compound (A-1-BOC) were 62.0% and 15.6%, respectively.

As a result of thermogravimetric measurement (TG), the pyrolysis temperature of the resulting compound (A-1-BOC) was 150° C. or higher (Evaluation A).

As a result of evaluation of the solubility in PGME and PGMEA, each solubility was 20% by mass or more (Evaluation A), and compound (A-1-BOC) was evaluated to have an excellent solubility. Therefore, compound (A-1-BOC) was evaluated to have a high preservation stability in a solution state and also be sufficiently applicable to an edge bead rinse liquid (mixed liquid of PGME/PGMEA) widely used in a semiconductor microfabrication process.

(Synthesis Experimental Example 2) Synthesis of A-1-MeBOC

In a container having an inner volume of 200 mL, equipped with a stirrer, a condenser and a burette, 6.4 g (12.4 mmol) of the resulting compound (A-1) and 5.4 g (27 mmol) of t-butyl bromoacetate (produced by Sigma-Aldrich Co. LLC.) were charged to 100 mL of acetone, 3.8 g (27 mmol) of potassium carbonate (produced by Sigma-Aldrich Co. LLC.) and 0.8 g of 18-crown-6 were added thereto, and the content was stirred under reflux for 3 hours to perform a reaction, thereby providing a reaction liquid. Next, the reaction liquid was concentrated, 100 g of pure water was added to a concentrated liquid to precipitate a reaction product, and the resultant was cooled to room temperature and thereafter filtered to separate a solid.

The resulting solid was subjected to filtration, dried, and thereafter separated and purified by column chromatography to thereby provide 1.8 g of an objective compound (A-1-MeBOC) represented by the following formula (A-1-MeBOC).

The molecular weight of the resulting compound (A-1-MeBOC) was measured by the above method, and as a result, it was 744.

The resulting compound (A-1-MeBOC) was subjected to the NMR measurement under the above measurement conditions, and thus the following peaks were observed and it was confirmed that the compound had a chemical structure of the following formula (A-1-MeBOC).

δ (ppm) 7.2-8.7 (14H, Ph-H), 6.7 (1H, C—H), 4.7-4.8 (4H, C—CH$_2$—C), 1.3-1.4 (18H, C—CH$_3$)

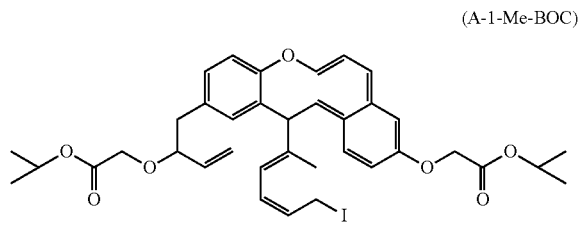 [SMILES: C=CC(Cc1ccc2c(c1)C(/C(C)=C/C=C\CI)\C=c1/ccc(OCC(=O)OC(C)C)c/c1=C/C=C/O2)OCC(=O)OC(C)C]

(A-1-Me-BOC)

As a result of organic element analysis, the carbon concentration and the oxygen concentration of the resulting compound (A-1-MeBOC) were 62.9% and 15.0%, respectively.

As a result of thermogravimetric measurement (TG), the pyrolysis temperature of the resulting compound (A-1-MeBOC) was 150° C. or higher (Evaluation A).

As a result of evaluation of the solubility in PGME and PGMEA, each solubility was 20% by mass or more (Evaluation A), and compound (A-1-MeBOC) was evaluated to have an excellent solubility. Therefore, compound (A-1-MeBOC) was evaluated to have a high preservation stability in a solution state and also be sufficiently applicable to an edge bead rinse liquid (mixed liquid of PGME/PGMEA) widely used in a semiconductor microfabrication process.

(Synthesis Experimental Example 3) Synthesis of A-2-BOC

In a container having an inner volume of 200 mL, equipped with a stirrer, a condenser and a burette, 6.5 g (12.5 mmol) of the compound (A-2) and 5.5 g (25 mmol) of di-t-butyl dicarbonate (produced by Sigma-Aldrich Co. LLC.) were charged to 100 mL of acetone, 3.45 g (25 mmol) of potassium carbonate (produced by Sigma-Aldrich Co. LLC.) was added thereto, and the content was stirred at 40° C. for 10 hours to perform a reaction, thereby providing a reaction liquid. Next, the reaction liquid was concentrated, 100 g of pure water was added to a concentrated liquid to precipitate a reaction product, and the resultant was cooled to room temperature and thereafter filtered to separate a solid.

The resulting solid was subjected to filtration, dried, and thereafter separated and purified by column chromatography to thereby provide 1.7 g of an objective compound (A-2-BOC) represented by the following formula (A-2-BOC).

The molecular weight of the resulting compound (A-2-BOC) was measured by the above method, and as a result, it was 762.

The resulting compound (A-2-BOC) was subjected to the NMR measurement under the above measurement conditions, and thus the following peaks were observed and it was confirmed that the compound had a chemical structure of the following formula (A-2-BOC).

δ (ppm) 7.2-8.5 (12H, Ph-H), 6.4 (1H, C—H), 3.6 (3H, O—C—H), 1.6 (18H, C—CH$_3$)

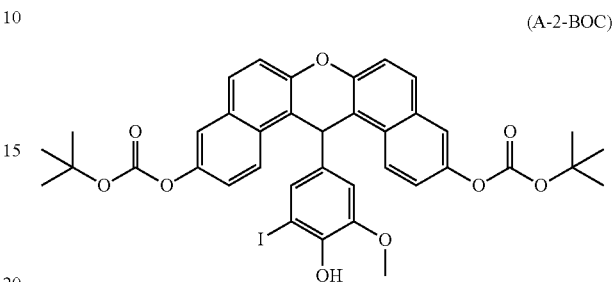

(A-2-BOC)

As a result of organic element analysis, the carbon concentration and the oxygen concentration of the resulting compound (A-2-BOC) were 59.9% and 18.9%, respectively.

As a result of thermogravimetric measurement (TG), the pyrolysis temperature of the resulting compound (A-2-BOC) was 150° C. or higher (Evaluation A).

As a result of evaluation of the solubility in PGME and PGMEA, each solubility was 20% by mass or more (Evaluation A), and compound (A-2-BOC) was evaluated to have an excellent solubility. Therefore, compound (A-2-BOC) was evaluated to have a high preservation stability in a solution state and also be sufficiently applicable to an edge bead rinse liquid (mixed liquid of PGME/PGMEA) widely used in a semiconductor microfabrication process.

(Synthesis Experimental Example 4) Synthesis of A-3-BOC

In a container having an inner volume of 200 mL, equipped with a stirrer, a condenser and a burette, 6.3 g (12.5 mmol) of the compound (A-3) and 5.5 g (25 mmol) of di-t-butyl dicarbonate (produced by Sigma-Aldrich Co. LLC.) were charged to 100 mL of acetone, 3.45 g (25 mmol) of potassium carbonate (produced by Sigma-Aldrich Co. LLC.) was added thereto, and the content was stirred at 20° C. for 10 hours to perform a reaction, thereby providing a reaction liquid. Next, the reaction liquid was concentrated, 100 g of pure water was added to a concentrated liquid to precipitate a reaction product, and the resultant was cooled to room temperature and thereafter filtered to separate a solid.

The resulting solid was subjected to filtration, dried, and thereafter separated and purified by column chromatography to thereby provide 2.2 g of an objective compound (A-3-BOC) represented by the following formula (A-3-BOC).

The molecular weight of the resulting compound (A-3-BOC) was measured by the above method, and as a result, it was 762.

The resulting compound (A-3-BOC) was subjected to the NMR measurement under the above measurement conditions, and thus the following peaks were observed and it was confirmed that the compound had a chemical structure of the following formula (A-3-BOC).

δ (ppm) 7.0-8.1 (12H, Ph-H), 6.1 (1H, C—H), 1.6 (18H, C—CH$_3$)

(A-3-BOC)

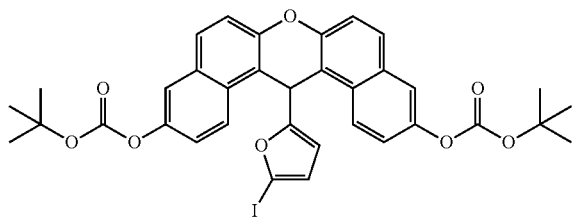

As a result of organic element analysis, the carbon concentration and the oxygen concentration of the resulting compound (A-3-BOC) were 59.5% and 18.0%, respectively.

As a result of thermogravimetric measurement (TG), the pyrolysis temperature of the resulting compound (A-3-BOC) was 150° C. or higher (Evaluation A).

As a result of evaluation of the solubility in PGME and PGMEA, each solubility was 20% by mass or more (Evaluation A), and compound (A-3-BOC) was evaluated to have an excellent solubility. Therefore, compound (A-3-BOC) was evaluated to have a high preservation stability in a solution state and also be sufficiently applicable to an edge bead rinse liquid (mixed liquid of PGME/PGMEA) widely used in a semiconductor microfabrication process.

(Synthesis Experimental Example 5) Synthesis of B-1-BOC

In a container having an inner volume of 200 mL, equipped with a stirrer, a condenser and a burette, 6.5 g (12.5 mmol) of the compound (B-1) and 5.5 g (25 mmol) of di-t-butyl dicarbonate (produced by Sigma-Aldrich Co. LLC.) were charged to 100 mL of acetone, 3.45 g (25 mmol) of potassium carbonate (produced by Sigma-Aldrich Co. LLC.) was added thereto, and the content was stirred at 40° C. for 12 hours to perform a reaction, thereby providing a reaction liquid. Next, the reaction liquid was concentrated, 100 g of pure water was added to a concentrated liquid to precipitate a reaction product, and the resultant was cooled to room temperature and thereafter filtered to separate a solid.

The resulting solid was subjected to filtration, dried, and thereafter separated and purified by column chromatography to thereby provide 2.4 g of an objective compound (B-1-BOC) represented by the following formula (B-1-BOC).

The molecular weight of the resulting compound (B-1-BOC) was measured by the above method, and as a result, it was 716.

The resulting compound (B-1-BOC) was subjected to the NMR measurement under the above measurement conditions, and thus the following peaks were observed and it was confirmed that the compound had a chemical structure of the following formula (B-1-BOC).

δ (ppm) 7.2-8.6 (14H, Ph-H), 6.7 (1H, C—H), 1.6 (18H, C—CH$_3$)

(B-1-BOC)

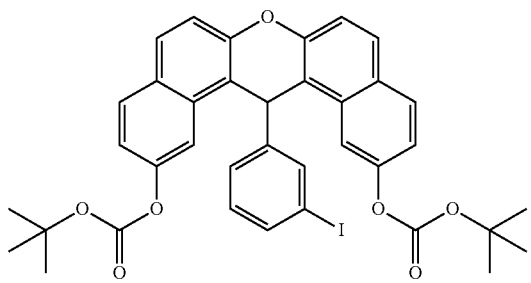

As a result of organic element analysis, the carbon concentration and the oxygen concentration of the resulting compound (B-1-BOC) were 62.0% and 15.6%, respectively.

As a result of thermogravimetric measurement (TG), the pyrolysis temperature of the resulting compound (B-1-BOC) was 150° C. or higher (Evaluation A).

As a result of evaluation of the solubility in PGME and PGMEA, each solubility was 20% by mass or more (Evaluation A), and compound (B-1-BOC) was evaluated to have an excellent solubility. Therefore, compound (B-1-BOC) was evaluated to have a high preservation stability in a solution state and also be sufficiently applicable to an edge bead rinse liquid (mixed liquid of PGME/PGMEA) widely used in a semiconductor microfabrication process.

(Synthesis Experimental Example 6) Synthesis of B-2-BOC

In a container having an inner volume of 200 mL, equipped with a stirrer, a condenser and a burette, 6.7 g (12.5 mmol) of the compound (B-2) and 5.5 g (25 mmol) of di-t-butyl dicarbonate (produced by Sigma-Aldrich Co. LLC.) were charged to 100 mL of acetone, 3.45 g (25 mmol) of potassium carbonate (produced by Sigma-Aldrich Co. LLC.) was added thereto, and the content was stirred at 40° C. for 10 hours to perform a reaction, thereby providing a reaction liquid. Next, the reaction liquid was concentrated, 100 g of pure water was added to a concentrated liquid to precipitate a reaction product, and the resultant was cooled to room temperature and thereafter filtered to separate a solid.

The resulting solid was subjected to filtration, dried, and thereafter separated and purified by column chromatography to thereby provide 1.7 g of an objective compound (B-2-BOC) represented by the following formula (B-2-BOC).

The molecular weight of the resulting compound (B-2-BOC) was measured by the above method, and as a result, it was 762.

The resulting compound (B-2-BOC) was subjected to the NMR measurement under the above measurement conditions, and thus the following peaks were observed and it was confirmed that the compound had a chemical structure of the following formula (B-2-BOC).

δ (ppm) 7.4-8.6 (12H, Ph-H), 6.5 (1H, C—H), 3.8 (3H, O—C—H), 1.8 (18H, C—CH$_3$)

(B-2-BOC)

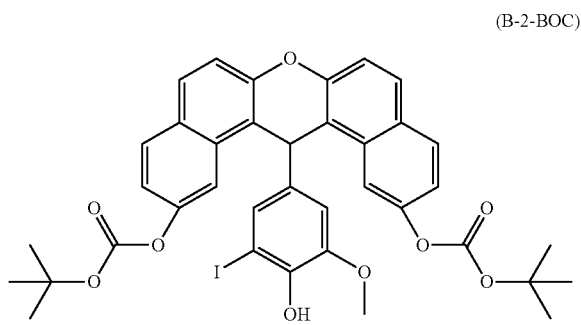 [SMILES: COc1cc(C2c3c(ccc4ccc(OC(=O)OC(C)(C)C)cc34)Oc3ccc4ccc(OC(=O)OC(C)(C)C)cc4c32)cc(I)c1O]

(B-3-BOC)

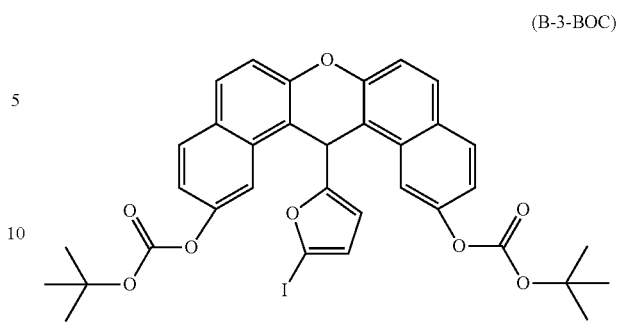

As a result of organic element analysis, the carbon concentration and the oxygen concentration of the resulting compound (B-2-BOC) were 59.9% and 18.9%, respectively.

As a result of thermogravimetric measurement (TG), the pyrolysis temperature of the resulting compound (B-2-BOC) was 150° C. or higher (Evaluation A).

As a result of evaluation of the solubility in PGME and PGMEA, each solubility was 20% by mass or more (Evaluation A), and compound (B-2-BOC) was evaluated to have an excellent solubility. Therefore, compound (B-2-BOC) was evaluated to have a high preservation stability in a solution state and also be sufficiently applicable to an edge bead rinse liquid (mixed liquid of PGME/PGMEA) widely used in a semiconductor microfabrication process.

(Synthesis Experimental Example 7) Synthesis of B-3-BOC

In a container having an inner volume of 200 mL, equipped with a stirrer, a condenser and a burette, 6.3 g (12.5 mmol) of the compound (B-3) and 5.5 g (25 mmol) of di-t-butyl dicarbonate (produced by Sigma-Aldrich Co. LLC.) were charged to 100 mL of acetone, 3.45 g (25 mmol) of potassium carbonate (produced by Sigma-Aldrich Co. LLC.) was added thereto, and the content was stirred at 40° C. for 12 hours to perform a reaction, thereby providing a reaction liquid. Next, the reaction liquid was concentrated, 100 g of pure water was added to a concentrated liquid to precipitate a reaction product, and the resultant was cooled to room temperature and thereafter filtered to separate a solid.

The resulting solid was subjected to filtration, dried, and thereafter separated and purified by column chromatography to thereby provide 2.2 g of an objective compound (B-3-BOC) represented by the following formula (B-3-BOC).

The molecular weight of the resulting compound (B-3-BOC) was measured by the above method, and as a result, it was 706.

The resulting compound (B-3-BOC) was subjected to the NMR measurement under the above measurement conditions, and thus the following peaks were observed and it was confirmed that the compound had a chemical structure of the following formula (B-3-BOC).

δ (ppm) 6.9-8.0 (12H, Ph-H), 6.3 (1H, C—H), 1.5 (18H, C—CH$_3$)

As a result of organic element analysis, the carbon concentration and the oxygen concentration of the resulting compound (B-3-BOC) were 59.5% and 18.1%, respectively.

As a result of thermogravimetric measurement (TG), the pyrolysis temperature of the resulting compound (B-3-BOC) was 150° C. or higher (Evaluation A).

As a result of evaluation of the solubility in PGME and PGMEA, each solubility was 20% by mass or more (Evaluation A), and compound (B-3-BOC) was evaluated to have an excellent solubility. Therefore, compound (B-3-BOC) was evaluated to have a high preservation stability in a solution state and also be sufficiently applicable to an edge bead rinse liquid (mixed liquid of PGME/PGMEA) widely used in a semiconductor microfabrication process.

(Synthesis Experimental Example 8) Synthesis of Resin (IR-1-BOC)

A four-neck flask having a bottom outlet and an inner volume of 1 L, equipped with a Dimroth condenser, a thermometer and a stirring blade, was prepared. To this four-neck flask were charged 50.1 g of A-1-BOC obtained in Synthesis Experimental Example 1 (70 mmol, produced by Mitsubishi Gas Chemical Company, Inc.), 21.0 g of a 40% by mass aqueous formalin solution (280 mmol as formaldehyde, produced by Mitsubishi Gas Chemical Company, Inc.) and 0.97 mL of 98% by mass sulfuric acid (produced by Kanto Chemical Co., Inc.) under a nitrogen stream, and the reaction was allowed to run under ordinary pressure for 7 hours with refluxing at 100° C. Thereafter, 180.0 g of o-xylene (special grade chemical, produced by Wako Pure Chemical Industries, Ltd.) as a dilution solvent was added to the reaction liquid and left to stand, and then an aqueous phase being a bottom phase was removed. Furthermore, the resultant was neutralized and washed with water, and o-xylene was distilled off under reduced pressure, thereby providing 54.2 g of a resin (IR-1-BOC) as a brown solid.

In the resulting resin (IR-1-BOC), Mn was 1975, Mw was 4150, and Mw/Mn was 2.10. In addition, the carbon concentration was 71.6% by mass, and the oxygen concentration was 16.5% by mass.

As a result of thermogravimetric measurement (TG), the 10% thermal weight loss temperature of the resulting resin (IR-1-BOC) was 150° C. or higher (Evaluation A). Therefore, the resin was evaluated to be applicable to high-temperature baking.

As a result of evaluation of the solubility in PGME and PGMEA, the solubility was 20% by mass or more (Evaluation A), and resin (IR-1-BOC) was evaluated to have a high preservation stability in a solution state and also be sufficiently applicable to an edge bead rinse liquid (mixed liquid of PGME/PGMEA) widely used in a semiconductor microfabrication process.

(Synthesis Experimental Example 9) Synthesis of Resin (IR-2-BOC)

A four-neck flask having a bottom outlet and an inner volume of 1 L, equipped with a Dimroth condenser, a thermometer and a stirring blade, was prepared. To this four-neck flask were charged 50.1 g of A-1-BOC obtained in Synthesis Experimental Example 1 (70 mmol, produced by Mitsubishi Gas Chemical Company, Inc.), 50.9 g of 4-biphenylaldehyde (280 mmol, produced by Mitsubishi Gas Chemical Company, Inc.), 100 mL of anisole (produced by Kanto Chemical Co., Inc.) and 10 mL of oxalic acid dihydrade (produced by Kanto Chemical Co., Inc.) under a nitrogen stream, and the reaction was allowed to run under ordinary pressure for 7 hours with refluxing at 100° C. Thereafter, 180.0 g of o-xylene (special grade chemical, produced by Wako Pure Chemical Industries, Ltd.) as a dilution solvent was added to the reaction liquid and left to stand, and then an aqueous phase being a bottom phase was removed. Furthermore, the resultant was neutralized and washed with water, and the solvent and the unreacted 4-biphenylaldehyde in the organic phase were distilled off under reduced pressure, thereby providing 84.7 g of a resin (IR-2-BOC) as a brown solid.

In the resulting resin (IR-2-BOC), Mn was 2182, Mw was 3910, and Mw/Mn was 1.79. In addition, the carbon concentration was 73.2% by mass, and the oxygen concentration was 15.5% by mass.

As a result of thermogravimetric measurement (TG), the 10% thermal weight loss temperature of the resulting resin (IR-2-BOC) was 150° C. or higher (Evaluation A). Therefore, the resin was evaluated to be applicable to high-temperature baking.

As a result of evaluation of the solubility in PGME and PGMEA, the solubility was 20% by mass or more (Evaluation A), and resin (IR-2-BOC) was evaluated to have an excellent solubility.

(Synthesis Example 7) Synthesis of BisN-1

In a container having an inner volume of 100 mL, equipped with a stirrer, a condenser and a burette, 3.20 g (20 mmol) of 2,6-naphthalenediol (reagent produced by Sigma-Aldrich Co. LLC.) and 1.82 g (10 mmol) of 4-biphenylcarbaldehyde (produced by Mitsubishi Gas Chemical Company, Inc.) were charged to 30 mL of methyl isobutyl ketone, 5 mL of 95% sulfuric acid was added thereto, and the content was stirred at 30° C. for 6 hours to perform a reaction, thereby providing a reaction liquid. Next, the reaction liquid was concentrated, 50 g of pure water was added to a concentrated liquid to precipitate a reaction product, and the resultant was cooled to room temperature and thereafter filtered to separate a solid.

The resulting solid was subjected to filtration, dried, and thereafter separated and purified by column chromatography to thereby provide 0.2 g of an objective compound (BisN-1) represented by the following formula (BisN-1).

The molecular weight of the resulting compound (BisN-1) was measured by the above method, and as a result, it was 466.

The resulting compound (BisN-1) was subjected to the NMR measurement under the above measurement conditions, and thus the following peaks were observed and it was confirmed that the compound had a chemical structure of the following formula (BisN-1).

δ (ppm) 9.3-9.4 (4H, O—H), 7.0-8.5 (19H, Ph-H), 6.8 (1H, C—H)

Herein, the resulting compound (BisN-1) having a substituent of 2,6-naphthalenediol at the 1-position was confirmed from signals of protons at the 3-position and the 4-position being doublets.

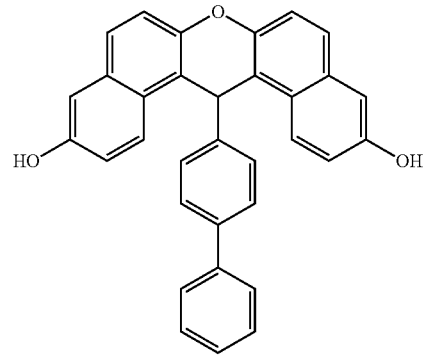

(BisN-1)

As a result of evaluation of the solubility in PGME and PGMEA, each solubility was 10% by mass or more and less than 20% by mass (Evaluation B).

(Synthesis Experimental Example 10) Synthesis of BisN-1-BOC

In a container having an inner volume of 200 mL, equipped with a stirrer, a condenser and a burette, 5.8 g (12.5 mmol) of the compound (BisN-1) and 5.5 g (25 mmol) of di-t-butyl dicarbonate (produced by Sigma-Aldrich Co. LLC.) were charged to 100 mL of acetone, 3.45 g (25 mmol) of potassium carbonate (produced by Sigma-Aldrich Co. LLC.) was added thereto, and the content was stirred at 20° C. for 6 hours to perform a reaction, thereby providing a reaction liquid. Next, the reaction liquid was concentrated, 100 g of pure water was added to a concentrated liquid to precipitate a reaction product, and the resultant was cooled to room temperature and thereafter filtered to separate a solid.

The resulting solid was subjected to filtration, dried, and thereafter separated and purified by column chromatography to thereby provide 2 g of an objective compound (BisN-1-BOC) represented by the following formula (BisN-1-BOC).

The molecular weight of the resulting compound (BisN-1-BOC) was measured by the above method, and as a result, it was 666.

The resulting compound (BisN-1-BOC) was subjected to the NMR measurement under the above measurement conditions, and thus the following peaks were observed and it was confirmed that the compound had a chemical structure of the following formula (BisN-1-BOC).

δ (ppm) 7.2-8.7 (19H, Ph-H), 6.8 (1H, C—H), 1.6 (18H, C—CH₃)

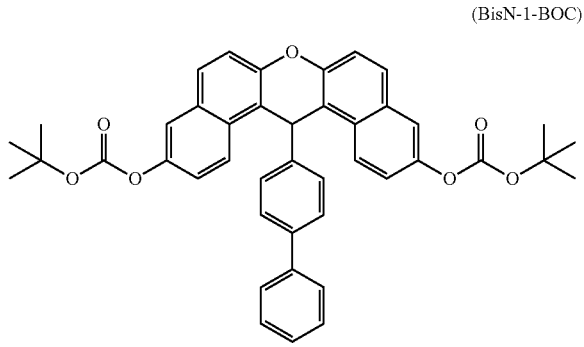 [SMILES: CC(C)(C)OC(=O)Oc1ccc2c3c(ccc2c1)Oc1ccc2cc(OC(=O)OC(C)(C)C)ccc2c1C3c1ccc(-c2ccccc2)cc1]
(BisN-1-BOC)

As a result of organic element analysis, the carbon concentration and the oxygen concentration of the resulting compound (BisN-1-BOC) were 77.5% and 16.8%, respectively.

As a result of thermogravimetric measurement (TG), the pyrolysis temperature of the resulting compound (BisN-1-BOC) was 150° C. or higher (Evaluation A).

As a result of evaluation of the solubility in PGME and PGMEA, each solubility was 20% by mass or more (Evaluation A), and compound (BisN-1-BOC) was evaluated to have an excellent solubility. Therefore, compound (BisN-1-BOC) was evaluated to have a high preservation stability in a solution state and also be sufficiently applicable to an edge bead rinse liquid (mixed liquid of PGME/PGMEA) widely used in a semiconductor microfabrication process.

Each of the compounds and the resins obtained in Synthesis Experimental Example 1 to 10 had a relatively low molecular weight and a low viscosity, and also had a low glass transition temperature of 100° C. or lower. Therefore, a material for forming an underlayer film for lithography using such a compound or resin can be improved in terms of embedding properties in a relatively advantageous manner. In addition, each of the compounds and the resins had a pyrolysis temperature of 150° C. or higher (Evaluation A), and had a high heat resistance due to rigidity of its structure, after leaving of an acid-dissociable group. Therefore, such a compound or resin can be used even under a high-temperature baking condition.

(Synthesis Comparative Example 1) Synthesis of Resin for Comparative Examples

A four-neck flask having a bottom outlet and an inner volume of 10 L, equipped with a Dimroth condenser, a thermometer and a stirring blade was prepared. To this four-neck flask were charged 1.09 kg (7 mol, produced by Mitsubishi Gas Chemical Company, Inc.) of 1,5-dimethylnaphthalene, 2.1 kg (28 mol as formaldehyde, produced by Mitsubishi Gas Chemical Company, Inc.) of a 40% by mass aqueous formalin solution and 0.97 mL of 98% by mass sulfuric acid (produced by Kanto Chemical Co., Inc.) under a nitrogen stream, and allowed the reaction to run under ordinary pressure for 7 hours with refluxing at 100° C. Thereafter, ethylbenzene (special grade chemical, produced by Wako Pure Chemical Industries, Ltd.) (1.8 kg) as a dilution solvent was added to the reaction solution and left to stand, and then an aqueous phase being a bottom phase was removed. Furthermore, the resultant was neutralized and washed with water, and ethylbenzene and the unreacted 1,5-dimethylnaphthalene were distilled off under reduced pressure, thereby providing 1.25 kg of a dimethylnaphthalene formaldehyde resin as a light-brown solid.

With respect to the molecular weight of the resulting dimethylnaphthalene formaldehyde, Mn was 562, Mw was 1168 and Mw/Mn was 2.08. In addition, the carbon concentration was 84.2% by mass, and the oxygen concentration was 8.3% by mass.

Subsequently, a four-neck flask having an inner volume of 0.5 L, equipped with a Dimroth condenser, a thermometer and a stirring blade, was prepared. To this four-neck flask were charged 100 g (0.51 mol) of the dimethylnaphthalene formaldehyde resin obtained as described above and 0.05 g of paratoluenesulfonic acid under a nitrogen stream, heated for 2 hours with the temperature being raised to 190° C., and then stirred. Thereafter, 52.0 g (0.36 mol) of 1-naphthol was further added thereto, and further heated to 220° C. to allow the reaction to run for 2 hours. After being diluted with a solvent, the resultant was neutralized and washed with water, and the solvent was removed under reduced pressure to thereby provide 126.1 g of a modified resin (CR-1) as a blackish brown solid.

With respect to the resulting resin (CR-1), Mn was 885, Mw was 2220 and Mw/Mn was 4.17. In addition, the carbon concentration was 89.1% by mass and the oxygen concentration was 4.5% by mass.

Examples 1 to 10 and Comparative Example 1

Each composition for forming an underlayer film for lithography was prepared so that each composition shown in Table 1 was achieved. The following materials were used as materials shown in Table 1.

Acid generator: di-tert-butyldiphenyliodonium nonafluoromethanesulfonate (DTDPI) produced by Midori Kagaku Co., Ltd.

Crosslinking agent: Nikalac MX270 (Nikalac) produced by Sanwa Chemical Co., Ltd.

Organic solvent: propylene glycol monomethyl ether acetate (PGMEA)

Novolac: PSM4357 produced by Gun Ei Chemical Industry Co., Ltd.

[Etching Resistance]

Then, an etching test was performed under conditions shown below to evaluate etching resistance. The evaluation results are shown in Table 1.

[Etching Test]

Etching apparatus: RIE-10NR manufactured by Samco Inc.

Output: 50 W
Pressure: 20 Pa
Time: 2 min
Etching gas
Ar gas flow rate:$CF_4$ gas flow rate:$O_2$ gas flow rate=50:5:5 (sccm)

The evaluation of etching resistance was performed according to the following procedure.

First, an underlayer film of novolac was prepared under the same conditions as those in Example 1 except that novolac (PSM4357 produced by Gunei Chemical Industry Co., Ltd.) was used instead of the compound (A-1-BOC) used in Example 1. Then, the etching test was performed with respect to the underlayer film of novolac as a subject, and the etching rate in that time was measured.

Then, the etching test was performed with respect to each underlayer film of Examples 1 to 10 and Comparative Example 1 as a subject, and the etching rate in that time was measured.

Then, the etching resistances were evaluated according to the following criteria based on the etching rate of the underlayer film using novolac.

<Evaluation Criteria>

A; etching rate of less than −10% compared with the etching rate of underlayer film of novolac B; etching rate of −10% to +5% compared with the etching rate of underlayer film of novolac C; etching rate of more than +5% compared with the etching rate of underlayer film of novolac

TABLE 1

| | Material for forming underlayer film (parts by mass) | Solvent (parts by mass) | Acid generator (parts by mass) | Cross-linking agent (parts by mass) | Evaluation of etching resistance |
|---|---|---|---|---|---|
| Example 1 | A-1-BOC (10) | PGMEA (90) | DTDPI (0.5) | Nikalac (0.5) | A |
| Example 2 | A-1 MeBOC (10) | PGMEA (90) | DTDPI (0.5) | Nikalac (0.5) | A |
| Example 3 | A-2-BOC (10) | PGMEA (90) | DTDPI (0.5) | Nikalac (0.5) | A |
| Example 4 | A-3-BOC (10) | PGMEA (90) | DTDPI (0.5) | Nikalac (0.5) | A |
| Example 5 | B-1-BOC (10) | PGMEA (90) | DTDPI (0.5) | Nikalac (0.5) | A |
| Example 6 | B-2-BOC (10) | PGMEA (90) | DTDPI (0.5) | Nikalac (0.5) | A |
| Example 7 | B-3-BOC (10) | PGMEA (90) | DTDPI (0.5) | Nikalac (0.5) | A |
| Example 8 | IR-1-BOC (10) | PGMEA (90) | DTDPI (0.5) | Nikalac (0.5) | B |
| Example 9 | IR-2-BOC (10) | PGMEA (90) | DTDPI (0.5) | Nikalac (0.5) | A |
| Example 10 | BisN-1-BOC (10) | PGMEA (90) | DTDPI (0.5) | Nikalac (0.5) | A |
| Comparative Example 1 | CR-1 (10) | PGMEA (90) | DTDPI (0.5) | Nikalac (0.5) | C |

Example 11

Then, the composition for forming an underlayer film for lithography in Example 1 was coated on a $SiO_2$ substrate having a film thickness of 300 nm, and baked at 240° C. for 60 seconds and further at 400° C. for 120 seconds to thereby form an underlayer film having a film thickness of 85 nm. A resist solution for ArF was coated on the underlayer film, and baked at 130° C. for 60 seconds to thereby form a photoresist layer having a film thickness of 140 nm. Herein, as the resist solution for ArF, one prepared by blending 5 parts by mass of the compound of the following formula (5), 1 part by mass of triphenylsulfonium nonafluoromethanesulfonate, 2 parts by mass of tributylamine, and 92 parts by mass of PGMEA was used.

A compound of formula (5) was prepared as follows. That is, 4.15 g of 2-methyl-2-methacryloyloxyadamantane, 3.00 g of methacryloyloxy-γ-butyrolactone, 2.08 g of 3-hydroxy-1-adamantyl methacrylate and 0.38 g of azobisisobutyronitrile were dissolved in 80 mL of tetrahydrofuran to provide a reaction solution. This reaction solution was subjected to polymerization under a nitrogen atmosphere for 22 hours with the reaction temperature being kept at 63° C., and thereafter the reaction solution was dropped in 400 mL of n-hexane. A product resin thus obtained was solidified and purified, and a white powder produced was taken by filtration and dried under reduced pressure at 40° C. overnight to provide a compound represented by the following formula.

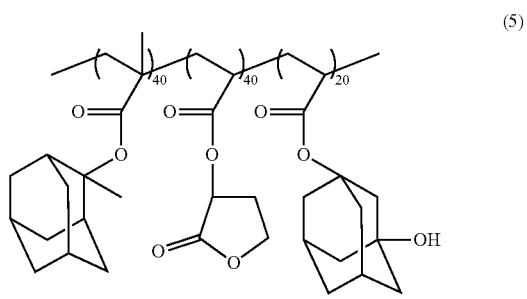

In the formula (5), the numerals 40, 40, and 20 indicate the proportions of the respective constituent units, and do not mean a block copolymer.

Then, the photoresist layer was exposed by using an electron beam lithography apparatus (ELS-7500, produced by Elionix, Inc., 50 keV), baked at 115° C. for 90 seconds (PEB), and developed with a 2.38% by mass aqueous tetramethylammonium hydroxide (TMAH) solution for 60 seconds, thereby providing a positive-type resist pattern.

Comparative Example 2

Except that no underlayer film was formed, the same manner as in Example 11 was performed to form a photoresist layer directly on a $SiO_2$ substrate to provide a positive-type resist pattern.

[Evaluation]

The shapes of the resist patterns of 45 nm L/S (1:1) and 80 nm L/S (1:1) provided in each of Example 11 and Comparative Example 2 were observed by using an electron microscope (S-4800) manufactured by Hitachi Ltd. A case where the shape of the resist pattern after development had no pattern collapse and had good rectangularity was evaluated to be good and a case the shape had pattern collapse and did not have good rectangularity was evaluated to be poor. In the observation results, the minimum line width where there was no pattern collapse and rectangularity was good was defined as the resolution and used as an evaluation index. Furthermore, the minimum amount of electron beam energy, where a good pattern shape could be drawn, was defined as the sensitivity and used as an evaluation index. The results are shown in Table 2.

TABLE 2

| | Material for forming underlayer film | Resolution (nmL/S) | Sensitivity (μC/cm²) | Resist pattern formation after development |
|---|---|---|---|---|
| Example 11 | Material described in Example 1 | 45 | 10 | Good |
| Comparative Example 2 | Not used | 80 | 26 | Not good |

As can be seen from Table 2, it was at least confirmed that Example 11 was significantly excellent in both of resolution and sensitivity as compared with Comparative Example 2. It was also confirmed that the resist pattern shape after development had no pattern collapse and had good rectangularity. Furthermore, it was also confirmed from the difference in the resist pattern shape after development that the material for forming an underlayer film for lithography in Example 11 had good adhesiveness with a resist material.

Example 12

The composition for forming an underlayer film for lithography used in Example 1 was coated on a $SiO_2$ substrate having a thickness of 300 nm, and baked at 240° C. for 60 seconds and further at 400° C. for 120 seconds to thereby form an underlayer film having a thickness of 90 nm. A silicon-containing intermediate layer material was coated on the underlayer film, and baked at 200° C. for 60 seconds to thereby form an intermediate layer film having a thickness of 35 nm. Furthermore, the resist solution for ArF was coated on the intermediate layer film, and baked at 130° C. for 60 seconds to thereby form a photoresist layer having a thickness of 150 nm. Herein, as the silicon-containing intermediate layer material, a silicon atom-containing polymer obtained below was used.

In 200 g of tetrahydrofuran (THF) and 100 g of pure water were dissolved 16.6 g of 3-carboxypropyltrimethoxysilane, 7.9 g of phenyltrimethoxysilane and 14.4 g of 3-hydroxypropyltrimethoxysilane, the liquid temperature was set at 35° C., 5 g of oxalic acid was dropped, and thereafter the resultant was heated to 80° C. to perform a condensation reaction of silanol. Next, 200 g of diethyl ether was added to separate an aqueous layer, an organic liquid layer was washed with ultrapure water twice, 200 g of propylene glycol monomethyl ether acetate (PGMEA) was added, and THF, diethyl ether, and water were removed under reduced pressure with the liquid temperature being raised to 60° C., to provide a silicon atom-containing polymer.

Then, the photoresist layer was mask-exposed by using an electron beam lithography apparatus (ELS-7500, produced by Elionix Inc., 50 keV), baked at 115° C. for 90 seconds (PEB), and developed with a 2.38% by mass aqueous tetramethylammonium hydroxide (TMAH) solution for 60 seconds, thereby providing a positive-type resist pattern of 45 nmL/S (1:1). Thereafter, a silicon-containing intermediate layer film (SOG) was subjected to dry etching processing with the resulting resist pattern as a mask, and subsequently dry etching processing of the underlayer film with the resulting silicon-containing intermediate layer film pattern as a mask and dry etching processing of the $SiO_2$ film with the resulting underlayer film pattern as a mask were sequentially performed by use of RIE-10NR manufactured by Samco Inc.

The respective etching conditions are as shown below.
Etching conditions of resist intermediate layer film with resist pattern
Output: 50 W
Pressure: 20 Pa
Time: 1 min
Etching gas
Ar gas flow rate:$CF_4$ gas flow rate:$O_2$ gas flow rate=50:8:2 (sccm)
Etching conditions of resist underlayer film with resist intermediate film pattern
Output: 50 W
Pressure: 20 Pa
Time: 2 min
Etching gas
Ar gas flow rate:$CF_4$ gas flow rate:$O_2$ gas flow rate=50:5:5 (sccm)
Etching conditions of $SiO_2$ film with resist underlayer film pattern
Output: 50 W
Pressure: 20 Pa
Time: 2 min
Etching gas
Ar gas flow rate:$C_5F_{12}$ gas flow rate:$C_2F_6$ gas flow rate:$O_2$ gas flow rate=50:4:3:1 (sccm)

[Evaluation]

The pattern cross section (shape of $SiO_2$ film after etching) in Example 12, obtained as above, was observed by using an electron microscope (S-4800) manufactured by Hitachi Ltd., and it was thus at least confirmed that the underlayer film in Example 12 was favorable because the shape of the $SiO_2$ film after etching in multilayer resist processing was rectangular and no defect was observed.

As described above, the present embodiment is not intended to be limited to the above Examples, and can be appropriately modified without departing the gist thereof.

The present application is based on Japanese Patent Application (Japanese Patent Application No. 2015-170191) filed with JPO on Aug. 31, 2015, the content of which is herein incorporated as reference.

The compound and the resin according to the present invention have a relatively high heat resistance and also a relatively high solvent solubility, and can be applied to a wet process. Therefore, a material for forming an underlayer film for lithography, containing the compound or the resin according to the present invention, and a composition including the material can be widely and effectively utilized in various applications in which these properties are required. Therefore, the present invention can be widely and effectively utilized for, for example, an electric insulating material; a resist resin; a sealing resin for a semiconductor; an adhesive for a printed wiring board; an electric laminated board mounted on electrical equipment, electronic equipment, industrial equipment and the like; a matrix resin for a prepreg mounted on electrical equipment, electronic equipment, industrial equipment and the like; a material for a build-up laminated board; a resin for fiber-reinforced plastics; a sealing resin for a liquid crystal display panel; a paint; various coating agents; an adhesive; a coating agent for a semiconductor; a resist resin for a semiconductor; and a resin for forming an underlayer film. The present invention can be particularly effectively utilized in the field of an underlayer film for lithography and an underlayer film for a multilayer resist.

The invention claimed is:
1. A method for forming an underlayer film for lithography, comprising:
    forming an underlayer film on a substrate using a composition for forming an underlayer film, the composition including a solvent and a material for forming an underlayer film; and
    forming at least one photoresist layer on the underlayer film,
    the material for forming an underlayer film including at least any of a compound represented by following formula (1-1) or a resin including a structural unit derived from a compound represented by the following formula (1-1),

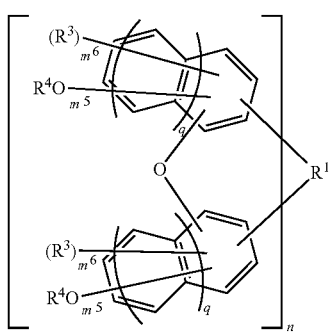
(1-1)

wherein, $R^1$ represents a 2n-valent group having 1 to 60 carbon atoms, or a single bond, each $R^3$ independently represents a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, or a thiol group, and may be the same or different in the same naphthalene ring or benzene ring, each $R^4$ independently represents a hydrogen atom or an acid-dissociable group, in which at least one $R^4$ represents an acid-dissociable group, n is an integer of 1 to 4, and structural formulae of n structural units in square brackets [ ] may be the same or different when n is an integer of 2 or more, each $m^5$ is independently an integer of 1 to 6, each $m^6$ is independently an integer of 0 to 5, $m^5+m^6$ is an integer of 1 to 6, and each q is independently 0 or 1.

2. The method according to claim 1, wherein the compound represented by the formula (1-1) is a compound represented by following formula (1-2),

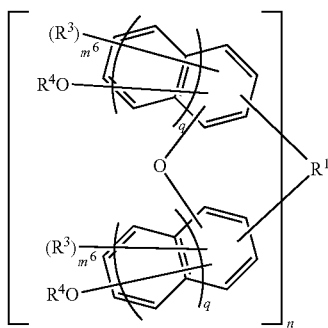
(1-2)

wherein $R^1$, $R^3$, $R^4$, $m^6$, n and q are the same as defined above, provided that at least one $R^4$ represents an acid-dissociable group.

3. The method according to claim 2, wherein the compound represented by the formula (1-2) is a compound represented by following formula (1-3),

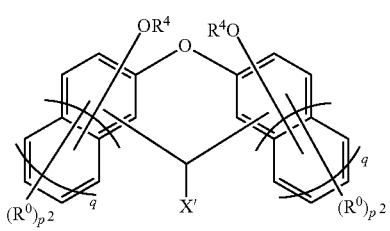
(1-3)

wherein $R^4$ and q are the same as defined above, X' represents a hydrogen atom, a halogen atom, or a monovalent group having 1 to 59 carbon atoms, each $R^0$ independently represents an alkyl group having 1 to 4 carbon atoms, or a halogen atom, and may be the same or different in the same naphthalene ring or benzene ring, and each $p^2$ is independently an integer of 0 to 5, provided that at least one $R^4$ represents an acid-dissociable group.

4. The method according to claim 3, wherein q in the formula (1-3) is 1.

5. The method according to claim 4, wherein the compound is represented by following formula (1-5) or following formula (1-6),

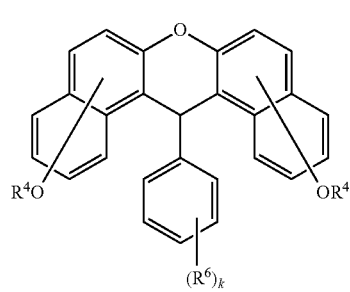
(1-5)

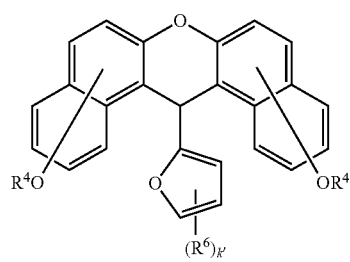
(1-6)

wherein $R^4$ is the same as defined above, $R^6$ represents at least one selected from the group consisting of a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, a thiol group and a hydroxyl group, k is an integer of 1 to 5, and k' is an integer of 1 to 3, provided that at least one $R^4$ represents an acid-dissociable group.

6. A method for forming an underlayer film for lithography, comprising:

forming an underlayer film on a substrate using a composition for forming an underlayer film, the composition including a solvent and a material for forming an underlayer film; and forming at least one photoresist layer on the underlayer film, the material for forming an underlayer film including at least any of a compound represented by following formula (1) or a resin including a structural unit derived from a compound represented by the following formula (1),

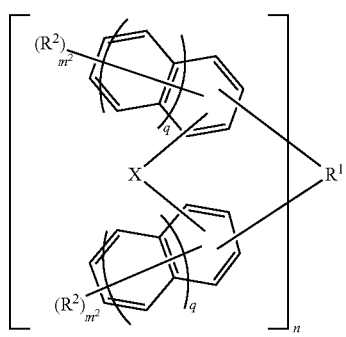

(1)

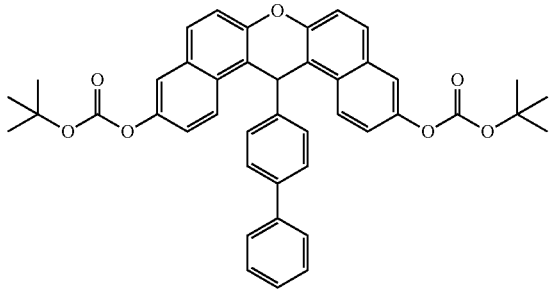

(BisN-1-BOC)

wherein $R^1$ represents a 2n-valent group having 1 to 60 carbon atoms, or a single bond, each $R^2$ independently represents a halogen atom, a straigh, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, a thiol group, a hydroxyl group, or a group where a hydrogen atom of a hydroxyl group is substituted with an acid-dissociable group, and may be the same or different in the same naphthalene ring or benzene ring, in which at least one $R^2$ represents a group where a hydrogen atom of a hydroxyl group is substituted with an acid-dissociable group, n is an integer of 1 to 4, and structural formulae of n structural units in square brackets [ ] may be the same or different when n is an integer of 2 or more, X represents an oxygen atom, a sulfur atom, or a non-bridging group, each $m^2$ is independently an integer of 0 to 7, provided that at least one $m^2$ is an integer of 1 to 7, and each q is independently 0 or 1, wherein the compound has a group including an iodine atom.

7. The method according to claim 5, wherein the compound represented by the formula (1-5) or the formula (1-6) is at least one selected from the group consisting of following compounds.

(A-2-BOC)

(A-3-BOC)

(B-1-BOC)

(A-1-BOC)

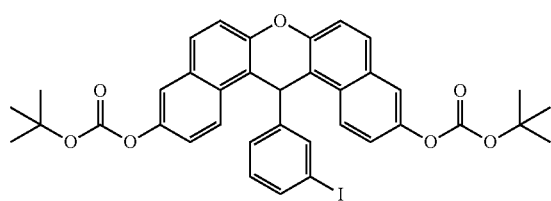

(B-2-BOC)

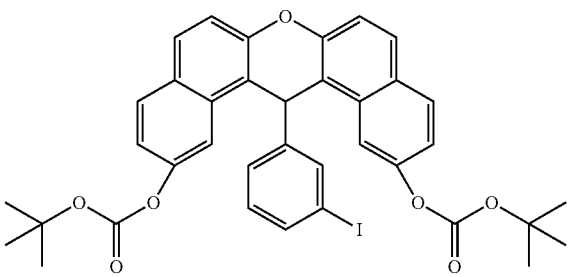

(A-1-MeBOC)

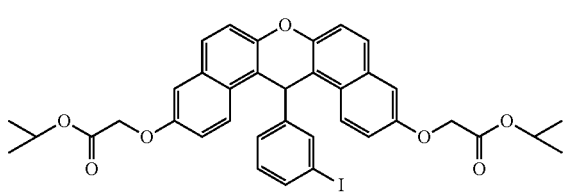

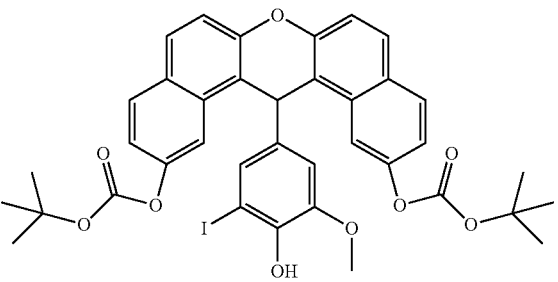

-continued (B-3-BOC)

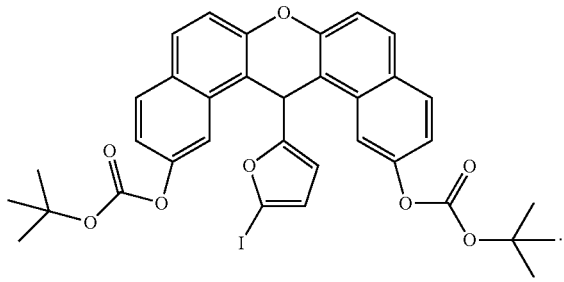

8. The method according to claim 1, wherein the composition further includes an acid generator.

9. The method according to claim 1, wherein the composition further includes a crosslinking agent.

10. An underlayer film for lithography, formed according to the method of claim 1.

11. A resist pattern forming method comprising:
a step of forming an underlayer film on a substrate using a composition for forming an underlayer film, the composition including a solvent and a material for forming an underlayer film, the material for forming an underlayer film including at least any of a compound represented by following formula (1-1) or a resin including a structural unit derived from a compound represented by the following formula (1-1),

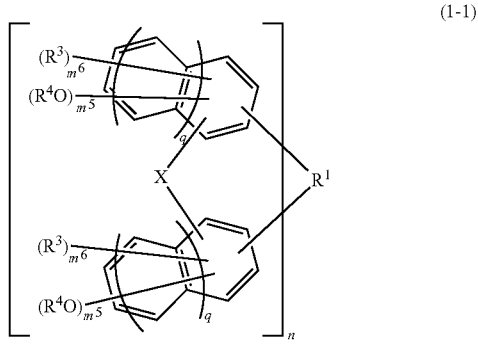

(1-1)

wherein $R^1$ represents a 2n-valent group having 1 to 60 carbon atoms, or a single bond, each $R^3$ independently represents a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, or a thiol group, and may be the same or different in the same naphthalene ring or benzene ring, each $R^4$ independently represents a hydrogen atom or an acid-dissociable group, in which at least one $R^4$ represents an acid-dissociable group, n is an integer of 1 to 4, and structural formulae of n structural units in square brackets [ ] may be the same or different when n is an integer of 2 or more, each $m^5$ is independently an integer of 1 to 6, each $m^6$ is independently an integer of 0 to 5, $m^5 + m^6$ is an integer of 1 to 6, and each q is independently 0 or 1 a step of forming at least one photoresist layer on the underlayer film, and a step of irradiating a predetermined region of the photoresist layer with radiation, and developing it.

12. A circuit pattern forming method comprising:
a step of forming an underlayer film on a substrate using a composition for forming an underlayer film, the composition including a solvent and a material for forming an underlayer film, the material for forming an underlayer film including at least any of a compound represented by following formula (1-1) or a resin including a structural unit derived from a compound represented by the following formula (1-1),

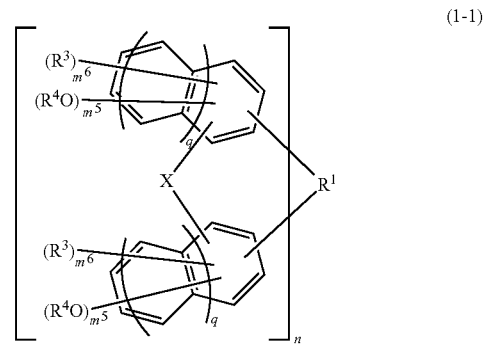

(1-1)

wherein $R^1$ represents a 2n-valent group having 1 to 60 carbon atoms, or a single bond, each $R^3$ independently represents a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, or a thiol group, and may be the same or different in the same napthalene ring of benzene ring, each $R^4$ independently represents a hydrogen atom or an acid-dissociable group, in which at least one $R^4$ represents an acid-dissociable group, n is an integer of 1 to 4, and structural formulae of n structural units in square brackets [ ] may be the same or different when n is an integer of 2 or more, each $m^5$ is independently an integer of 1 to 6, each $m^6$ is independently an integer of 0 to 5, $m^5 + m^6$ is an integer of 0 to 6, and each q is independently 0 or 1 a step of forming an intermediate layer film on the underlayer film by using a silicon atom-containing resist intermediate layer film material, a step of forming at least one photoresist layer on an intermediate layer film, a step of irradiating a predetermined region of the photoresist layer with radiation, and developing it to form a resist pattern, a step of etching the intermediate layer film with the resist pattern as a mask, to form an intermediate layer film pattern, a step of etching the underlayer film with the intermediate layer film pattern as an etching mask, to form an underlayer film pattern, and a step of etching the substrate with the underlayer film pattern as an etching mask, to form a pattern on the substrate.

13. A resin comprising a structural unit derived from a compound represented by following formula (1-1),

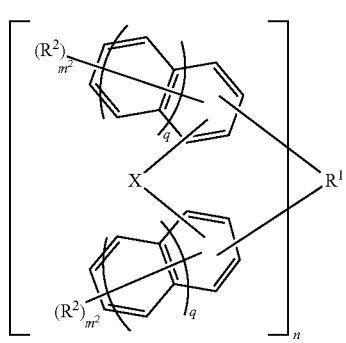

(1)

wherein $R^1$ represents a 2n-valent group having 1 to 60 carbon atoms, or a single bond, each $R^3$ independently represents a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, or a thiol group, and may be the same or different in the same naphthalene ring or benzene ring, each $R^4$ independently represents a hydrogen atom or an acid-dissociable group, in which at least one $R^4$ represents an acid-dissociable group, n is an integer of 1 to 4, and structural formulae of n structural units in square brackets [ ] may be the same or different when n is an integer of 2 or more, each $m^5$ is independently an integer of 1 to 6, each $m^6$ is independently an integer of 0 to 5, $m^5 + m^6$ is an integer of 1 to 6, and each q is independently 0 or 1.

14. A purification method comprising:

a step of providing a solution (A) by dissolving a compound represented by following formula (1-1) or a resin including a structural unit derived from a compound represented by the following formula (1-1) in a solvent, and a first extraction step of bringing the resulting solution (A) into contact with an acidic aqueous solution, to extract impurities in the solution (A), wherein the solvent to be used in the step of providing the solution (A) comprises an organic solvent optionally immiscible with water,

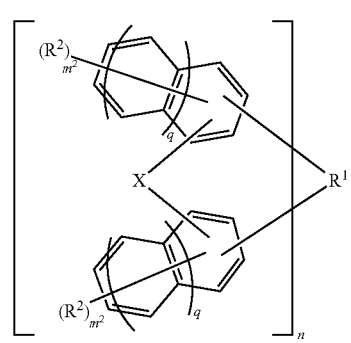

(1)

wherein $R^1$ represents a 2n-valent group having 1 to 60 carbon atoms, or a single bond, each $R^2$ independently represents a halogen atom, a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, or a thiol group, and may be the same or different in the same napthalene ring or benzene ring, each $R^4$ independently represents a hydrogen atom or an acid-dissociable group, in which at least one $R^4$ represents an acid-dissociable group, n is an integer of 1 to 4, and structural formulae of n structural units in square brackets [ ] may be the same or different when n is an integer of 2 or more, each $m^5$ is independently an integer of 1 to 6, each $m^6$ is independently an integer of 0 to 5, $m^5 + m^6$ is an integer of 1 to 6, and each q is independently 0 or 1.

15. The purification method according to claim 14, wherein the acidic aqueous solution is an aqueous mineral acid solution or an aqueous organic acid solution, the aqueous mineral acid solution is an aqueous solution of at least one mineral acid selected from the group consisting of hydrochloric acid, sulfuric acid, nitric acid and phosphoric acid, and the aqueous organic acid solution is an aqueous solution of at least one organic acid selected from the group consisting of acetic acid, propionic acid, oxalic acid, malonic acid, succinic acid, fumaric acid, maleic acid, tartaric acid, citric acid, methanesulfonic acid, phenolsulfonic acid, p-toluenesulfonic acid and trifluoroacetic acid.

16. The purification method according to claim 14, wherein the organic solvent optionally immiscible with water is at least one organic solvent selected from the group consisting of toluene, 2-heptanone, cyclohexanone, cyclopentanone, methyl isobutyl ketone, propylene glycol monomethyl ether acetate and ethyl acetate.

17. The purification method according to claim 14, further comprising, after the first extraction step, a second extraction step of further bringing the solution (A) into contact with water, to further extract impurities in the solution (A).

* * * * *

UNITED STATES PATENT AND TRADEMARK OFFICE
CERTIFICATE OF CORRECTION

PATENT NO. : 11,143,962 B2
APPLICATION NO. : 15/755972
DATED : October 12, 2021
INVENTOR(S) : Takumi Toida et al.

It is certified that error appears in the above-identified patent and that said Letters Patent is hereby corrected as shown below:

In the Claims

Column 81, Line (20):
In Claim 6, delete "straigh," and insert -- straight, --, therefor.

Column 81, Line (44):
In Claim 7, delete "compounds." and insert -- compounds, --, therefor.

Column 84, Line (35):
In Claim 12, delete "napthalene ring of" and insert -- naphthalene ring or --, therefor.

Column 84, Line (44):
In Claim 12, delete "0 to 6," and insert -- 1 to 6, --, therefor.

Signed and Sealed this
Twenty-fourth Day of May, 2022

*Katherine Kelly Vidal*

Katherine Kelly Vidal
*Director of the United States Patent and Trademark Office*